US011780889B2

(12) United States Patent
Hause

(10) Patent No.: US 11,780,889 B2
(45) Date of Patent: *Oct. 10, 2023

(54) PORCINE CIRCOVIRUS TYPE 3 IMMUNOGENIC COMPOSITIONS AND METHODS OF MAKING AND USING THE SAME

(71) Applicant: Kansas State University Research Foundation, Manhattan, KS (US)

(72) Inventor: Ben Hause, Slayton, MN (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/658,519

(22) Filed: Apr. 8, 2022

(65) Prior Publication Data

US 2022/0251144 A1    Aug. 11, 2022

Related U.S. Application Data

(62) Division of application No. 17/249,100, filed on Feb. 19, 2021, which is a division of application No. 16/600,067, filed on Oct. 11, 2019, now Pat. No. 10,954,274, which is a division of application No. 15/768,356, filed as application No. PCT/US2016/057369 on Oct. 17, 2016, now Pat. No. 10,450,351.

(60) Provisional application No. 62/242,866, filed on Oct. 16, 2015.

(51) Int. Cl.
| | |
|---|---|
| *C07K 14/005* | (2006.01) |
| *C12N 7/00* | (2006.01) |
| *C07K 16/08* | (2006.01) |
| *A61P 31/20* | (2006.01) |
| *A61K 39/12* | (2006.01) |
| *A61K 39/39* | (2006.01) |
| *A61K 39/00* | (2006.01) |

(52) U.S. Cl.
CPC ............ *C07K 14/005* (2013.01); *A61K 39/12* (2013.01); *A61K 39/39* (2013.01); *A61P 31/20* (2018.01); *C07K 16/081* (2013.01); *C12N 7/00* (2013.01); *A61K 2039/53* (2013.01); *A61K 2039/70* (2013.01); *C12N 2750/10021* (2013.01); *C12N 2750/10022* (2013.01); *C12N 2750/10034* (2013.01)

(58) Field of Classification Search
None
See application file for complete search history.

(56) References Cited

U.S. PATENT DOCUMENTS

| | | | |
|---|---|---|---|
| 7,829,101 B2 | 11/2010 | Eichmeyer et al. | |
| 10,450,351 B2 | 10/2019 | Hause | |
| 10,954,274 B2* | 3/2021 | Hause | ...................... C12N 7/00 |
| 2008/0181910 A1* | 7/2008 | Roof | ...................... A61P 15/00 |
| | | | 424/204.1 |

FOREIGN PATENT DOCUMENTS

| | | |
|---|---|---|
| EP | 0784685 B1 | 4/2003 |
| JP | 2009297029 A | 12/2009 |
| WO | 2009049351 A1 | 4/2009 |
| WO | 2010027828 A2 | 3/2010 |
| WO | 2010037041 A2 | 4/2010 |
| WO | 2011091389 A2 | 7/2011 |

OTHER PUBLICATIONS

Petitioner's Power of Attorney for Post-Grant Review of U.S. Pat. No. 10,954,274, Case: PGR2022-00021, Dec. 22, 2021 (4 pages).
Notice of Filing Date Accorded To Petition and Time for Filing Patent Owner Preliminary Response, Case: PGR2022-00021, U.S. Pat. No. 10,954,274, Jan. 19, 2023 (6 pages).
Patent Owner's Mandatory Notices Under 37 C.F.R. § 42.8; Case: PGR2022-0002, U.S. Pat. No. 10,954,274 B2, entered Jan. 11, 2022 (5 pages).
Patent Owner's Power of Attorney; Case: PGR2022-00021, U.S. Pat. No. 10,954,274 B2, Jan. 11, 2022 (4 pages).
Petition for Post-Grant Review Under 35 U.S.C. §322 and 37 C.F.R. 37 C.F.R. §§42.200 et seq, Case: PGR2022-00021, U.S. Pat. No. 10,954,274 B2, Dec. 22, 2021 (98 pages).
Allan, et al., "Porcine circoviruses: a review," J Vet Diagn Invest 12:3-14 (2000).
Zhang, et al., "What is for dinner? Viral metagenomics of US store bought beef, pork, and chicken," Virology 468-470 (2014) 303-310.
Fenaux, et al., "A Chimeric Porcine Circovirus (PCV) with the Immunogenic Capsid Gene of the Pathogenic PCV Type 2 (PCV2) Cloned into the Genomic Backbone of the Nonpathogenic PCV1 Induces Protective Immunity Against PCV2 Infection in Pigs," Journal of Virology, Jun. 2004, p. 6297-6303, doi: 10.1128/JVI.78.12.6297-6303.2004.
Palinski, et al., "A Novel Porcine Circovirus Distantly Related to Known Circoviruses Is Associated with Porcine Dermatitis and Nephropathy Syndrome and Reproductive Failure," Journal of Virology, vol. 91, Issue 1, e011879-16, pp. 1-13.

(Continued)

*Primary Examiner* — Shanon A. Foley
(74) *Attorney, Agent, or Firm* — Tracey S. Truitt; Sandberg Phoenix & von Gontard P.C.

(57) ABSTRACT

A new species of circovirus, porcine circovirus type 3 (PCV3), was identified from sows with clinical symptoms normally associated with porcine circovirus type 2 (PCV2) infection and in aborted fetuses. Molecular and serological analyses suggest PCV3 commonly circulates in U.S. swine. The present disclosure provides immunological compositions and methods related to the production and administration of such compositions.

45 Claims, 2 Drawing Sheets

Specification includes a Sequence Listing.

(56) References Cited

OTHER PUBLICATIONS

Fux, et al., "Full genome characterization of porcine circovirus type 3 isolates reveals the existence of two distinct groups of virus strains," Virology Journal (2018) 15:25; DOI 0.1186/S12985-018-0929-3, pp. 1-9.
Knight-Jones, et al., "Veterinary and human vaccine evaluation methods," Proc R. Soc. B 281: 20132839, https://dx.doi.org/10.1098/rspb.2013.2839, pp. 1-10.
Sakharkar, et al, "Post-genomic Approaches in Drug and Vaccine Development," vol. 5; River Publishers, ISBN 978-87-93102-84-2 (Hardback), 978-87-93102-85-9 (Ebook), 2015 (21 pages).
Thomas, Sunil, "Vaccine Design Methods and Protocols vol. 2: Vaccines for Veterinary Diseases," Humana Press, ISSN 1064-3745, ISSN 1940-6029 (electronic), Methods in Molecular Biology, ISBN 978-1-4939-8039-0, ISBN 978-1-4939-3389-1 (eBook), DOI 10.1007/978-1-4939-3389-1, Publisher: Springer, 2016 (26 pages).
Plotikin, Stanley, "Vaccines, 6th Edition," Elsevier Saunders, ISBN-13: 9781455700905, Ebook: 9781455737987, expertconsult.com (34 pages).
Dutton, et al., "Porcine Circovirus 3," Swine Health Information Center By the Center for Food Security and Public Health, College of Veterinary Medicine, Iowa State University, Sep. 2016, http://www.cfsph.iastate.edu/pdf/shic-factsheet-porcine-circovirus-3 (16 pages).
Franzo, et al., "Genotyping Porcine Circovirus 3 (PCV-3) Nowadays: Does It Make Sense?", Viruses 2020, 12, 265, doi:10.3390/v12030265; www.mdpi.com/journal/viruses, pp. 1-13.
Zhai, et al., "Comparative epidemiology of porcine circovirus type 3 in pigs with different clinical presentations," Virology Journal (2017) 14:222, DOI 10.1186/s12985 017 0892 4, pp. 1-6.
Montgomery, "Discovery of novel virus in swine could prevent history from repeating," K-State News; https://www.k-state.edu/media/newsreleases/2016-11/porcine11416.html, pp. 1-3.
Mora-Diaz, "Isolation of PCV3 from Perinatal and Reproductive Cases of PCV3-Associated Disease and In Vivo Characterization of PCV3 Replication in CD/CD Growing Pigs," Viruses 2020, 12, 219, doi:10.3390/v12020219, www.mdpi.com/journal/viruses, pp. 1-21.
Prinz, et al, "Detection of PCV3 in German wild boars," Virology Journal (2019) 16:25, https://doi.org/10.1186/S12985-019-1133-9, pp. 1-7.
Xing, et al., "Complete Genomic Sequence of a Novel Porcine Circovirus 2 Strain CC12," Genome A Journals, Mar./Apr. 2014, vol. 2, Issue 2, e00318-14, doi: 10.1128/genomeA.00318-14, pp. 1-2.
Zhang, et al., "Development and application of a baculovirus-expressed capsid protein-based indirect ELISA for detection of porcine circovirus 3 IgG antibodies," BMC Veterinary Research (2019) 15:79, https://doi.org/10.1186/s12917-019-1810-3, pp. 1-10.
Klaumann, et al. "Current Knowledge on Porcine circovirus 3 (PCV-3): A Novel Virus With a Yet Unknown Impact on the Swine Industry," Front. Vet. Sci., Dec. 12, 2018, 5:315, doi: 10.3389/fvets.2018.00315, pp. 1-13.
Ellis, J., "Porcine Circovirus: A Historical Perspective," Veterinary Pathology 2014, vol. 51 2) 315-327; 2014, sagepub.com/journalsPermissions.nav; DOI: 10.1177/0300985814521245, pp. 315-327.
Arruda, et al., "PCV3-associated disease in the United States swine herd," Emerging Microbes Infections, 2019, vol. 8, https://doi10.1080/22221751.2019.1613176, pp. 684-698.
Printout of NCBI entry for GenBank Accession No. AIR09408.1, https://www.ncbi.nlm.nih.gov/protein/689594715 (1 page).
Printout of NCBI entry for GenBank Accession No. KM111537.1, https://www.ncbi.nlm.nih.gov/nuccore/KM111537 (1 page).
Printout of Combin function in Microsoft Excel (8 pages).
Li, et al., "Possible Cross-Species transmission of circoviruses and cycloviruses among farm animals," J Gen Virol. (2011), 92, 768-772, DOI 10.1099/vir.0.028704-0.
Printout of NCBI entry for GenBank Accession No. KX458235.1, https://www.ncbi.nlm.nih.gov/nuccore/ KX458235 (2 pages).
Printout of NCBI entry for GenBank Accession No. KT869077.1, https://www.ncbi.nlm.nih.gov/nuccore/ KT869077 (2 pages).
Xia, et al., "The prevalence and genetic diversity of porcine circovirus types 2 and 3 in Northeast China from 2015 to 2018," Springer, Archives of Virology (2019) 164:2435-2449, https://doi.org:10.1007/s00705-019-04336-4.
Van Oers, "Opportunities and challenges for the baculovirus expression system," Journal of Invertebrate Pathology, 107 (2011) S3-S15, doi:10.1016/j.jip.2011.05.001.
Liu, et al., "High repetitive arginine in the anterior of PCV3 capsid protein is a severe obstacle for its expression in $E.\ coli$," AMB Express (2020), 10:214, https://doi.org/10.1186/s13568-020-01163-8, pp. 1-7.
Declaration of Robert M. Nordgren, Case: PGR2022-00021, U.S. Pat. No. 10,954,274 B2, Dec. 21, 2021, pp. 1-95.
Curriculum Vitae of Robert M. Nordgren (6 pages).
Errata Sheet to Videotaped Deposition of Harm HogenEsch, D.V. M., Ph.D., Jul. 9, 2021, Executed Jul. 15, 2021 (4 pages).
Videotaped Deposition of Harm HogenEsch, D.V.M., Ph.D., Case: PGR2020-00076, U.S. Pat. No. 10,450,351 B2, dated Jul. 9, 2021, pp. 1-417.
Order Conduct of the Proceeding 37 C.F.R. § 42.5, Case: PGR2022-00021, U.S. Pat. No. 10,954,274 B2, Mar. 16, 2022 (4 pages).
Petitioner's Amended Mandatory Notices Under 37 C.F.R. § 42.8, Case: PGR2022-00021, U.S. Pat. No. 10,954,274 B2, Mar. 23, 2022 (5 pages).
Patent Owner's Updated Mandatory Notices Under 37 C.F.R. § 42.8, Case: PGR2022-00021, U.S. Pat. No. 10,954,274, May 10, 2022 (4 pages).
Decision Denying Institution of Post Grant Review 35 U.S.C. § 324, 37 C.F.R. § 42.4, Case: PGR2022-00021 U.S. Pat. No. 10,954,274 B2, Jul. 15, 2022 (26 pages).
Declaration of Jacob T. Whitt in Response To Petitioner's Sep. 14, 2021 Objections To Patent Owner's Evidence, Case: PGR2020-00076, U.S. Pat. No. 10,450,351 B2, served Sep. 28, 2021 (4 pages).
Petitioner's Response To Patent Owner's Second Objections To Petitioner's Evidence, Case: PGR2020-00076, U.S. Pat. No. 10,450,351 B2, dated Aug. 16, 2021 (13 pages).
Declaration of Jacob T. Whitt in Response To Petitioner's Objections To Patent Owner's Evidence, Case: PGR2020-00076, U.S. Pat. No. 10,450,351 B2, served May 19, 2021 (4 pages).
Patent Owner's Updated Exhibit List, Case: PGR2020-00076, U.S. Pat. No. 10,450,351 B2, served May 19, 2021 (10 pages).
Petitioner's Response To Patent Owner's Objections To Petitioner's Evidence, Case: PGR2020-00076, U.S. Pat. No. 10,450,351 B2, dated Mar. 3, 2021 (18 pages).
Declaration of Max E Rubinson, Case: PGR2020-00076, U.S. Pat. No. 10,450,351 B2, dated Mar. 3, 2021 (95 pages).
Expert Declaration of Dr. Sylvia D. Hall-Ellis, Case: PGR2020-00076, U.S. Pat. No. 10,450,351 B2, dated Mar. 3, 2021 (81 pages).
Patent Owner's Request for Oral Argument, Case: PGR2020-00076, U.S. Pat. No. 10,450,351 B2, dated Sep. 22, 2021 (5 pages).
Petitioner's Objections To Patent Owner's Evidence, Case: PGR2020-00076, U.S. Pat. No. 10,450,351 B2, dated Sep. 14, 2021 (7 pages).
Patent Owner's Sur-Reply, Case: PGR2020-00076, U.S. Pat. No. 10,450,351 B2, dated Sep. 7, 2021 (38 pages).
Notice of Filing Updated Petitioner's List of Exhibits and Ex. 1043, Case: PGR2020-00076, U.S. Pat. No. 10,450,351 B2, dated Aug. 13, 2021 (8 pages).
Judgment Final Written Decision Determining All Challenged Claims Unpatentable Denying Petitioner's Motion to Exclude Denying Patent Owner's Motion to Exclude 35 U.S.C. § 328(a), Case: PGR2020-00076, U.S. Pat. No. 10,450,351 B2, entered Jan. 31, 2022 (48 pages).
Record of Oral Hearing held Nov. 3, 2021, Case: PGR2020-00076, U.S. Pat. No. 10,450,351 B2, entered Dec. 13, 2021 (79 pages).
Petitioner's Demonstratives, Case: PGR2020-00076, U.S. Pat. No. 10,450,351 B2, dated Nov. 3, 2021 (139 pages).
Petitioner's Supplemental Power of Attorney for Post-Grant Review of U.S. Pat. No. 10,450,351, Case: PGR2020-00076, U.S. Pat. No. 10,450,351 B2, dated Oct. 29, 2021 (4 pages).

(56) References Cited

OTHER PUBLICATIONS

Patent Owner's Demonstratives for Oral Argument, Case: PGR2020-00076, U.S. Pat. No. 10,450,351, dated Nov. 3, 2021 (108 pages).
Petitioner's Reply in Support of Its Motion To Exclude Evidence, Case: PGR2020-00076, U.S. Pat. No. 10,450,351 B2, dated Oct. 27, 2021 (15 pages).
Patent Owner's Reply in Support of Motion To Exclude Petitioner's Evidence, Case: PGR2020-00076, U.S. Pat. No. 10,450,351 B2, dated Oct. 27, 2021 (17 pages).
Patent Owner's Opposition To Petitioner's Motion To Exclude, Case: PGR2020-00076, U.S. Pat. No. 10,450,351 B2, dated Oct. 20, 2021 (25 pages).
Petitioner's Opposition To Patent Owner's Motion To Exclude Evidence, Case: PGR2020-00076, U.S. Pat. No. 10,450,351 B2, entered Oct. 20, 2021 (16 pages).
Petitioner's Motion To Exclude Evidence, Case: PGR2020-00076, U.S. Pat. No. 10,450,351 B2, dated Oct. 13, 2021 (22 pages).
Patent Owner's Motion To Exclude Petitioner's Evidence, Case: PGR2020-00076, U.S. Pat. No. 10,450,351 B2, dated Oct. 13, 2021 (20 pages).
Order Setting Oral Argument 37 C.F.R. § 42.70, Case: PGR2020-00076, U.S. Pat. No. 10,450,351 B2, dated Sep. 29, 2021 (10 pages).
Decision Granting Petitioner's Motion to Withdraw and Substitute Counsel 37 C.F.R. § 42.10, Case: PGR2020-00076, U.S. Pat. No. 10,450,351 B2, dated Sep. 29, 2021 (3 pages).
Petitioner's Request for Oral Argument, Case: PGR2020-00076, U.S. Pat. No. 10,450,351 B2, dated Sep. 22, 2021 (5 pages).
Petitioner's Motion for Additional Discovery, Case: PGR2020-00076, U.S. Pat. No. 10,450,351 B2, dated Mar. 19, 2021 (24 pages).
Petitioner's Unopposed Motion To Withdraw Counsel, Case: PGR2020-00076, U.S. Pat. No. 10,450,351 B2, dated Mar. 19, 2021 (4 pages).
Order Conduct of Proceeding 35 U.S.C. § 42.5, Case: PGR2020-00076, U.S. Pat. No. 10,450,351 B2, dated Mar. 12, 2021 (5 pages).
Patent Owner's Objections To Petitioner's Evidence, Case: PGR2020-00076, U.S. Pat. No. 10,450,351 B2, entered Feb. 17, 2021 (7 pages).
Patent Owner's Notice of Deposition of Robert M. Nordgren, Case: PGR2020-00076, U.S. Pat. No. 10,450,351 B2, entered Aug. 11, 2021 (4 pages).
Patent Owner's Objections To Petitioner's Reply Evidence, Case: PGR2020-00076, U.S. Pat. No. 10,450,351 B2, entered: Aug. 2, 2021 (7 pages).
Petitioner's Updated Mandatory Notices Under 37 C.F.R. § 42.8, Case: PGR2020-00076, U.S. Pat. No. 10,450,351 B2, dated Jul. 26, 2021 (4 pages).
Petitioner's Reply To Patent Owner's Response, Case: PGR2020-00076, U.S. Pat. No. 10,450,351 B2, dated Jul. 26, 2021 (35 pages).
Notice of Stipulation To Extend Due Dates 2 and 3, Case: PGR2020-00076, U.S. Pat. No. 10,450,351 B2, dated Jul. 19, 2021 (4 pages).
Petitioner's Notice of Deposition of Harm Hogenesch, D.V.M., Ph D., Case: PGR2020-00076, U.S. Pat. No. 10,450,351 B2, dated Jun. 23, 2021 (3 pages).
Petitioner's Objections To Patent Owner's Evidence, Case: PGR2020-00076, U.S. Pat. No. 10,450,351 B2, dated May 5, 2021 (13 pages).
Patent Owner's Updated Mandatory Notices Under 37 C.F.R. § 42.8, Case: PGR2020-00076, U.S. Pat. No. 10,450,351, entered May 5, 2021 (5 pages).
Order Denying Petitioner's Motion for Additional Discovery 37 C.F.R. §§ 42.51(b)(2), 42.224, Case: PGR2020-00076, U.S. Pat. No. 10,450,351 B2, dated Apr. 29, 2021 (10 pages).
Patent Owner's Response, Case: PGR2020-00076, U.S. Pat. No. 10,450,351 B2, dated Apr. 28, 2021 (106 pages).
Patent Owner's Opposition To Petitioner's Motion for Additional Discovery, Case: PGR2020-00076, U.S. Pat. No. 10,450,351 B2, Entered: Mar. 26, 2021 (20 pages).
Patent Owner's Notice of Deposition of Robert M. Nordgren, Case: PGR2020-00076, U.S. Pat. No. 10,450,351 B2, Entered: Mar. 23, 2021 (5 pages).
Mandatory Notices of Patent Owner Kansas State University Research Foundation, Case: PGR2020-00076, U.S. Pat. No. 10,450,351 B2, dated Aug. 12, 2020 (4 pages).
Notice of Filing Date Accorded To Petition and Time for Filing Patent Owner Preliminary Response, Case: PGR2020-00076, U.S. Pat. No. 10,450,351, dated Aug. 7, 2020 (5 pages).
Petition for Post-Grant Review Under 35 U.S.C. § 322 and 37 C.F.R. 37 C.F.R. §§ 42.200 et seq, Case: PGR2020-00076, U.S. Pat. No. 10,450,351 B2, dated Jul. 22, 2020 (97 pages).
Petitioner's Power of Attorney for Post-Grant Review of U.S. Pat. No. 10,450,351 Under 35 U.S.C. § 322 and 37 C.F.R. § 42.204, Including the Accompanying Petition Therefor, Case: PGR2020-00076, U.S. Pat. No. 10,450,351 B2, dated Jul. 20, 2020 (4 pages).
Scheduling Order, Case: PGR2020-00076, U.S. Pat. No. 10,450,351 B2, dated Feb. 3, 2021 (11 pages).
Decision Granting Institution of Post-Grant Review 35 U.S.C. § 324, Case: PGR2020-00076, U.S. Pat. No. 10,450,351 B2, dated Feb. 3, 2021 (20 pages).
Patent Owner's Updated Mandatory Notices Under 37 C.F.R. § 42.8, Case: PGR2020-00076, U.S. Pat. No. 10,450,351, entered Sep. 28, 2020 (6 pages).
Patent Owner's Power of Attorney, Case: PGR2020-00076, U.S. Pat. No. 10,450,351, entered Sep. 28, 2020 (5 pages).
Order Granting Request for Director Review, Case: PGR2022-00021, U.S. Pat. No. 10,954,274 B2, dated Aug. 12, 2022 (3 pages).
Decision Vacating the Decision Denying Institution and Remanding to the Patent Trial and Appeal Board for Further Proceedings, Case: PGR2022-00021, U.S. Pat. No. 10,954,274 B2, dated Feb. 24, 2023 (9 pages).

* cited by examiner

PORCINE CIRCOVIRUS TYPE 3 IMMUNOGENIC COMPOSITIONS AND METHODS OF MAKING AND USING THE SAME

This application is a division of U.S. patent application Ser. No. 17/249,100, filed on Feb. 19, 2021, which is a division of U.S. patent application Ser. No. 16/600,067, filed Oct. 11, 2019, which is a division of Ser. No. 15/768,356, filed Apr. 13, 2018, which issued as U.S. Pat. No. 10,450,351 on Oct. 22, 2019, which is a National Phase filing of PCT Application No. PCT/US2016/057369, filed Oct. 17, 2016, which relates to and claims priority to U.S. Provisional Patent Application No. 62/242,866, which was filed on Oct. 16, 2015, all of which are incorporated herein by reference in their entirety.

SEQUENCE LISTING

This application contains a sequence listing in paper format and in computer readable format, the teachings and content of which are hereby incorporated by reference.

BACKGROUND OF THE DISCLOSURE

Porcine circovirus type 2 (PCV2) was first sporadically identified in pigs with postweaning multisystemic wasting syndrome (PMWS) in Canada in the mid 1990's. Epidemics of severe systemic disease associated with PCV2 were subsequently identified in Europe and Asia followed by North America. The widespread use of commercial vaccines has effectively controlled PCV2-associated disease (PCVAD) which includes PMWS, pneumonia, porcine dermatitis and nephropathy syndrome (PDNS) and reproductive failure. Retrospective studies have demonstrated that PCV2 circulated unnoticed in swine for decade's prior widespread clinical disease. A shift in dominant genotype from PCV2a to PCV2b appeared correspond to severe PCVAD. Recently, a new species of circovirus, termed porcine circovirus type 3 (PCV3), was identified from sows with clinical symptoms normally associated with PCV2 infection as well as in aborted fetuses.

SUMMARY OF THE DISCLOSURE

Tissues were collected from four sows from a farm with chronic poor reproductive performance which died acutely with clinical symptoms consistent with PDNS. Pathological examination of sow tissues noted purple skin lesions with acutely necrotic dermis and epidermis associated with hemorrhage and perivascular accumulations of white blood cells. The kidneys showed dilated renal tubules with lymphocyte and macrophage clusters within the interstitium and glomeruli and mild dysplasia in the tubular epithelial cells. Despite macroscopic and microscopic lesions typically found with PCV2 infection, immunohistochemistry and quantitative PCR (qPCR) were negative for PCV2 as well as for porcine reproductive and respiratory syndrome virus (PRRSV) and influenza A virus (IAV). Concurrently, mummified fetuses were collected from aborting sows on the same farm with similar skin lesions. Likewise, qPCR was negative for PCV2 as well as porcine reproductive and respiratory syndrome virus (PRRSV) and porcine parvovirus (PPV).

A tissue homogenate pool was prepared from three mummies and subjected to viral metagenomics sequencing as previously described. Of the 989,478 reads collected, 926,380 mapped to a reference *Sus scrofa* genome. De novo assembly of the unassembled reads yielded 27 contigs. The majority (54%) of the reads mapped to a 1246 bp contig which by BLASTN analysis was 98% similar to a partial circovirus genome detected in commercial pork meat by metagenomics sequencing. The remaining reads showed no similarity to known eukaryotic viruses. Rolling circle amplification was next performed on the mummy pool DNA followed by inverse PCR using primers overlapping an XhoI site contained within the circovirus contig. Agarose gel electrophoresis identified a single band approximately 2 kb. A 2,000 bp genome (SEQ ID NO. 1) was determined by Sanger sequencing of overlapping amplicons spanning the complete genome.

Genetic analysis identified an open reading frame (ORF1; SEQ ID NO. 3) encoding a predicted 296 amino acid (aa) protein (SEQ ID NO. 4) which by BLASTP analysis was 96% identical to the partial replicase (rep) protein of circoviridae PorkNW2/USA/2009 (accession ADU77001, 221 aa) and 54% identical to a 293 aa rep protein determined from a bat circovirus (accession AIF76248) in China. Conserved viral rep and helicase domains were identified from aa 9-93 and 162-251 of SEQ ID NO. 1, respectively. Similar to PorkNW2/USA/2009, no appropriate initiation codon was identified and an alternative GTC start codon or splicing from an upstream ATG is proposed. A second ORF (ORF2; SEQ ID NO. 5) in the opposite orientation encoded a predicted 214 aa protein (SEQ ID NO. 6) with 87% identity to the partial capsid (cap) sequence (110 aa) of PorkNW2/USA/2009 and 36-37% identity to capsids of PCV2 and duck circoviruses (233 and 257 aa, respectively). Similar to other circovirus cap proteins, the N-terminus consisted of a highly arginine-rich region approximately 32 aa in length. A third ORF (ORF3; SEQ ID NO. 7) encoding a predicted 233 aa protein (SEQ ID NO. 8) was 94% identical to one identified in a partial circovirus genome determined from ground beef and 39% identical to a Murid herpesvirus protein with unknown function. The predicted origin of replication contained a stem-loop structure with a loop nonamer identical to PCV1, TAGTATTAC (SEQ ID NO. 15), located between the rep and cap on the rep encoding strand (FIG. 1). Given the overall genetic and structural similarities to members of the genus Circovirus and <70% capsid aa identity to other species, the species is referred to as porcine circovirus 3 (PCV3) in the present application.

Phylogenetic analysis was performed in MEGA with sequences aligned by ClustalW. Phylogeny was inferred using the Maximum Likelihood method using the best fit LG with gamma distribution model with tree topology verified by 500 bootstrap replicates for rep protein sequences (FIG. 2). A scale representing the number of amino acid changes is shown. GenBank accession numbers are shown in parentheses. In FIG. 2, CaCV is canary circovirus; GuCV is gull circovirus; FiCV is finch circovirus; StCV is starling circovirus; PiCV is pigeon circovirus; BFDV, is beak and feather disease virus; DuCV is duck circovirus; GoCV is goose circovirus; SwCV is swan circovirus; BtCV is bat circovirus; PCV1 is porcine circovirus type 1; and, PCV2 is porcine circovirus type 2. As shown in the figure, PCV3 clustered with PorkNW2/USA/2009 and these were most closely related to a bat circovirus from China. Interestingly, PCV1 and PCV2 are also evolutionarily related to a different bat circovirus from Myanmar.

Tissue homogenates from three individual mummies and lung homogenates from the four sows that died with PDNS were analyzed with a qPCR assay targeting the PCV3 rep gene. The mummies were all positive with cycle threshold (Ct) values 16.7-21.3. Three of the four sows were also positive with Ct values 27.7-29.7.

To determine the incidence of PCV3, a total of 271 porcine nasal swab, oral fluids or lung homogenate samples submitted for diagnostic testing were screened with multiplexed Taqman assays targeting the rep and cap genes. Thirty four (12.5%) of samples were positive for both assays with similar Ct values. Two samples were positive only for the assay targeting PCV3 cap. The Ct values for positive samples were 20.3-35.8.

A peptide encompassing cap aa 35-214 of SEQ ID NO. 1 was expressed as a N-terminal 6×-histidine fusion protein in E. coli and purified by affinity chromatography. Denaturing electrophoresis indicated that the protein was expressed as a dimer, similarly observed for PCV2. ELISA was performed as previously described. Eighteen sera samples from 3-week old pigs from a specific pathogen free herd were used as negative controls and gave an average optical density of 0.49. A cutoff for positivity was set at three standard deviations above the average (OD>0.87). Sera from ten multiparous sows from the same farm were all positive with an average OD of 1.27. Twenty seven sera from a gilt farm that feeds replacement animals to the sow farm were also tested; seventeen (63%) were positive. Finally, forty six (55%) of a collection of 83 sera samples (animal ages unknown) submitted for diagnostic testing from multiple states were positive.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

Figure 1:
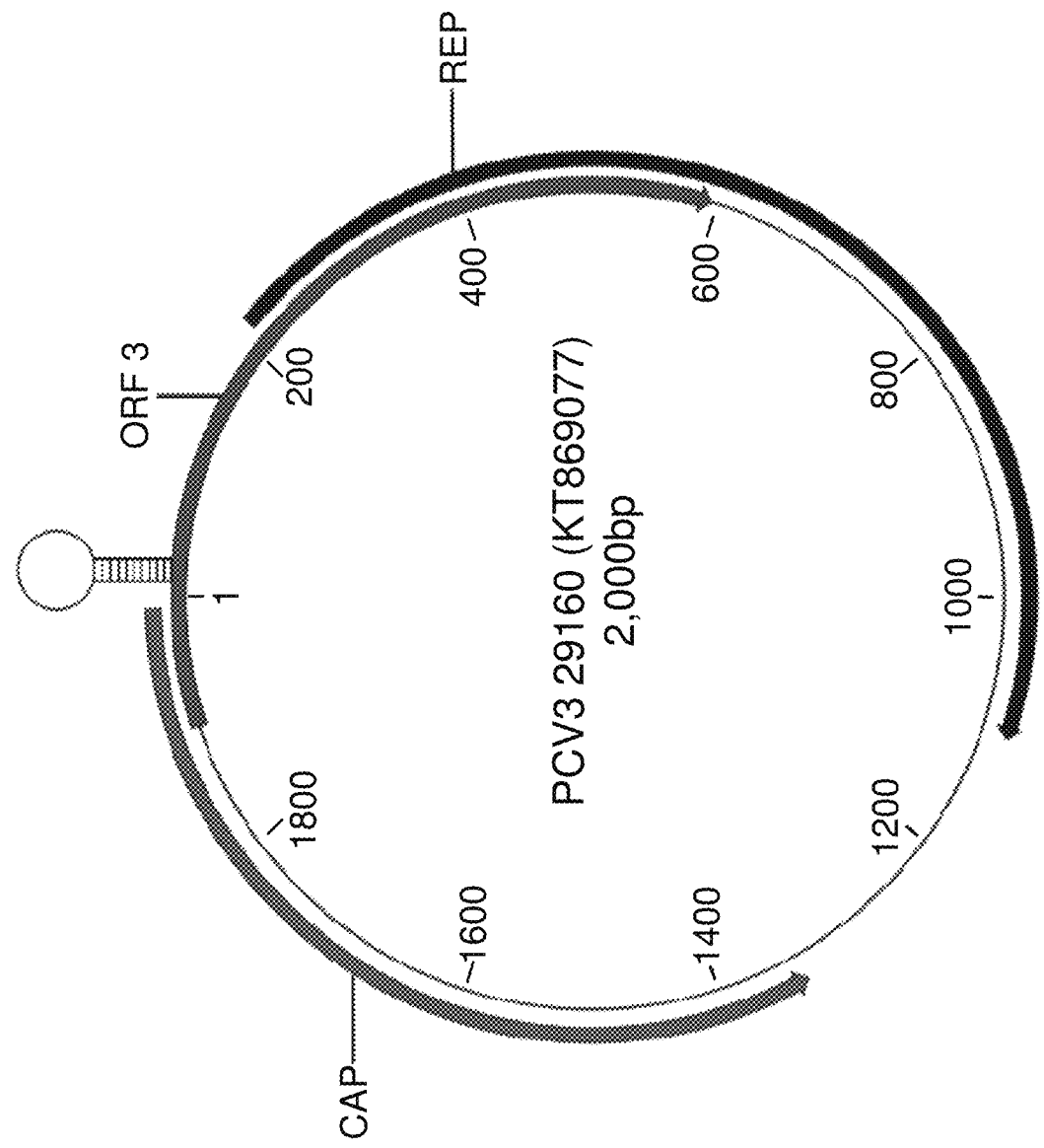
FIG. 1 is a diagram of porcine circovirus 3 genome organization.

In the present application, SEQ ID No. 1 is a nucleotide sequence of PCV3 genome; SEQ ID No. 2 is an amino acid sequence of PCV3 genome; SEQ ID No. 3 is a nucleotide sequence of the replicase (ORF1) of PCV3; SEQ ID No. 4 is an amino acid sequence of the replicase (ORF1) of PCV3; SEQ ID No 5 is a nucleotide sequence of the capsid (ORF2) of PCV3; SEQ ID No. 6 is an amino acid sequence of the capsid (ORF2) of PCV3; SEQ ID No. 7 is a nucleotide sequence of ORF3 of PCV3; SEQ ID No. 8 is an amino acid sequence of ORF3 of PCV3; SEQ ID No. 9 is a nucleotide sequence of Primer 1 PCV3 replicase; SEQ ID No. 10 is a nucleotide sequence of Primer 2 PCV3 replicase; SEQ ID No. 11 is a nucleotide sequence of probe PCV3 replicase; SEQ ID No. 12 is a nucleotide sequence of Primer 1 PCV3 capsid; SEQ ID No. 13 is a nucleotide sequence of Primer 2 PCV3 capsid; SEQ ID No. 14 is a nucleotide sequence of probe PCV3 capsid; SEQ ID No. 15 is an origin of replication contained a stem-loop structure with a loop nonamer; SEQ ID No. 16 is an internal cap gene primer; SEQ ID No. 17 is an internal cap gene primer; SEQ ID No. 18 is a primer for a portion of the PCV3 gene encoding amino acids (aa) 35-214; and SEQ ID No. 19 is a primer for a portion of the PCV3 gene encoding amino acids (aa) 35-214.

DETAILED DESCRIPTION

The following detailed description and examples set forth preferred materials and procedures used in accordance with the present disclosure. It is to be understood, however, that this description and these examples are provided by way of illustration only, and nothing therein shall be deemed to be a limitation upon the overall scope of the present disclosure.

Immunogenic Compositions and Methods of Making and Using Such Compositions

One aspect of the present disclosure provides a method of producing and/or recovering recombinant PCV3 ORF2 protein, by 1) infecting a number of susceptible cells in culture with a recombinant viral vector encoding a PCV3 protein, 2) expressing PCV3 protein by the recombinant viral vector, 3) recovering the PCV3 protein, and, 4) separating cell debris from the expressed PCV3 protein via a separation step.

In another aspect of the present disclosure, the inclusion of an inactivation step is preferred in order to inactivate the viral vector prior to recovery of PCV3 protein that will be used in an immunogenic or immunological composition such as a vaccine. Such a step can be performed as step 5) in addition to steps 1-4 described above.

In some forms, this inactivation is done either just before or just after the filtration or separation step. Any conventional inactivation method can be used for purposes of the present disclosure. Thus, inactivation can be performed by chemical and/or physical treatments. One representative inactivation method includes the addition of cyclized binary ethylenimine (BEI).

Optionally, the method described above may also include a neutralization step after step 5). For example, if the inactivation agent is BEI, addition of sodium thiosulfate to an equivalent amount is preferred. Preferably, the sodium thiosulfate is added in equivalent amount as compared to the BEI added for inactivation.

An "immunogenic or immunological composition" refers to a composition of matter that comprises at least one antigen which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction in the severity or prevalence of, up to and including a lack of symptoms normally displayed by an infected host, a quicker recovery time and/or a lowered viral titer in the infected host.

In preferred forms and especially in forms that will use the recombinant PCV3 protein in an immunogenic composition such as a vaccine, each lot or just selected lots of harvested PCV3 protein can be tested for inactivation. Thus a further aspect of the present disclosure relates to an inactivation test for determining the effectiveness of the inactivation of the recombination viral vector, comprising the steps: 1) contacting at least a portion of the culture fluid containing the recombinant viral vector with an inactivating agent, 2) adding a neutralization agent to neutralize the inactivation agent, and 3) determining the residual infectivity.

In preferred forms the recombinant viral vector containing PCV3 DNA and expressing PCV3 protein used to infect the cells is generated by transfecting a transfer vector that has had a PCV3 gene cloned therein into a viral vector. Preferably, only the portion of the transfer vector that contains the desired PCV3 DNA, such as the DNA encoding ORF1, ORF2, or ORFS, is transfected into the viral vector.

The term "transfected into a viral vector" means, and is used as a synonym for "introducing" or "cloning" a heterologous DNA into a viral vector, such as for example into a baculovirus vector. A "transfer vector" means a DNA molecule, that includes at least one origin of replication, the heterologous gene, in the present case of PCV3, DNA sequences which allow the cloning of said heterologous gene into the viral vector will be included. Preferably the sequences which allow cloning of the heterologous gene into the viral vector are flanking the heterologous gene. Even more preferably, those flanking sequences are at least homologous in parts with sequences of the viral vector. The sequence homology then allows recombination of both molecules, the viral vector, and the transfer vector to generate a recombinant viral vector containing the heterologous gene.

In more preferred forms, the methods of the present disclosure will begin with the isolation of PCV3 DNA. Any PCV3 gene can be used for purposes of the present disclosure. The PCV3 DNA is preferably amplified using PCR methods. The resulting DNA is then cloned into the transfer vector.

Thus, in one aspect of the present disclosure, a method for constructing a recombinant viral vector containing PCV3 DNA is provided. This method generally comprises the steps of: 1) cloning at least one recombinant PCV3 gene into a transfer vector; and 2) transfecting the portion of the transfer vector containing the recombinant PCV3 gene into a viral vector, to generate the recombinant viral vector. As noted above, the PCV3 gene can encode ORF1, ORF2, or ORF3.

According to a further aspect, the PCV3 DNA can be amplified prior to step 1) in vitro, wherein the flanking sequences of the PCV3 DNA are modified. In vitro methods for amplifying the PCV3 DNA and modifying the flanking sequences, cloning in vitro amplified PCV3 DNA into a transfer vector and suitable transfer vectors are described above or known to a person skilled in the art. Thus according to a further aspect, the present disclosure relates to a method for constructing a recombinant viral vector containing PCV3 DNA and expressing a desired PCV3 protein comprising the steps of: 1) amplifying PCV3 DNA in vitro, wherein the flanking sequences of said PCV3 DNA are modified, 2) cloning the amplified PCV3 ORF2 DNA into a transfer vector; and 3) transfecting the transfer vector or a portion thereof containing the recombinant PCV3 DNA into a viral vector to generate the recombinant viral vector. In some aspects, the modification of the flanking sequences of the PCV3 DNA is performed by introducing a 5' Kozak's sequence and/or an EcoR 1 site.

A further aspect of the present disclosure relates to a method for preparing a composition comprising PCV3 protein, and inactivated viral vector. This method generally comprises the steps of: 1) cloning the amplified PCV3 DNA into a transfer vector; 2) transfecting the portion of the transfer vector containing the recombinant PCV3 DNA into a virus; 3) infecting cells in media with the transfected viral vector; 4) causing the transfected viral vector to express the recombinant protein from the PCV3 DNA; 5) separating cells from the supernate; 6) recovering the expressed PCV3 protein; and 7) inactivating the recombinant viral vector. In preferred forms and as described above, a neutralization step, step 8), will be performed after step 7). Of course, prior to step 1) the PCV3 DNA can be amplified in vitro, preferably with flanking sequences of the PCV3 DNA, as described above.

In another aspect of the present disclosure, a method for preparing a composition, preferably an immunogenic composition, such as a vaccine, for invoking an immune response against PCV3 is provided. Generally, this method includes the steps of transfecting a construct into a virus, wherein the construct comprises 1) recombinant DNA from an ORF of PCV3, 2) infecting cells in growth media with the transfected virus, 3) causing the virus to express the recombinant ORF protein from PCV3, 4) recovering the expressed recombinant ORF protein, 5) and preparing the composition by combining the recovered protein with a suitable adjuvant and/or other pharmaceutically acceptable carrier. In some preferred forms, the composition also includes at least a portion of the viral vector expressing said PCV3 ORF protein, and/or a portion of the cell culture supernate "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIM adjuvant system (Ribi Inc.), Block co-polymer (CytRx, Atlanta Ga.), SAF-M (Chiron, Emeryville Calif.), monophosphoryl lipid A, Avirdine lipid-amine adjuvant, heat-labile enterotoxin from *E. coli* (recombinant or otherwise), cholera toxin, IMS 1314 or muramyl dipeptide among many others.

Preferably, the adjuvant is added in an amount of about 100 µg to about 10 mg per dose. Even more preferably, the adjuvant is added in an amount of about 100 µg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

In another aspect of the present disclosure, a method for preparing an immunogenic composition, such as a vaccine, for invoking an immune response against PCV3 comprises the steps of 1) expressing and recovering PCV3 ORF protein, and 2) admixing the recovered protein with a suitable adjuvant. Preferably, the expressing step 1) includes the steps as described for the preparation and recovery of PCV3 protein. Another optional step for this method includes cloning the amplified PCV3 ORF DNA into a first vector, excising the ORF DNA from this first vector, and using this excised PCV3 ORF DNA for cloning into the transfer vector. Preferably, the recovery step of this method also includes the step of separating the media from the cells and cell debris. This can be done in any conventional manner, with one preferred manner comprising filtering the cells, cell debris, and growth media through a filter having pores ranging in size from about 0.45 µM to about 1.0 µM. Finally, for this aspect, it is preferred to include a virus inactivation step prior to combining the recovered recombinant PCV3 ORF protein in a composition. When an inactivation step is included, it is also preferred to include a neutralization step, as described above.

Additionally, the composition can include one or more pharmaceutical-acceptable or veterinary-acceptable carriers. As used herein, "a pharmaceutical-acceptable carrier" or "veterinary-acceptable carrier" includes any and all solvents, dispersion media, coatings, stabilizing agents, diluents, preservatives, antibacterial and antifungal agents, isotonic agents, adsorption delaying agents, and the like. In one preferred form, the composition provided herewith, contains PCV3 ORF protein recovered from in vitro cultured cells, wherein said cells were infected with a recombinant viral vector containing PCV3 ORF DNA and expressing PCV3 ORF protein, and wherein the cell culture was treated to inactivate the viral vector, and an equivalent concentration of a neutralization agent was added, and wherein both an adjuvant and physiological saline are also added. As with the other aspects, the PCV3 ORF protein can be ORF1, ORF2, or ORF3. When included, the amount of physiological saline is preferably about 50 to about 90% (v/v), more preferably about 60 to 80% (v/v), still more preferably about 70% (v/v). Optionally, this method can also include the addition of a protectant. A protectant as used herein, refers to an anti-microbiological active agent, such as for example Gentamycin, Merthiolate, and the like. In particular adding a protectant is most preferred for the preparation of a multi-dose composition. Those anti-microbiological active agents are added in concentrations effective to prevent the composition of interest from any microbiological contamination or for inhibition of any microbiological growth within the composition of interest.

The methods of the present disclosure can also comprise the addition of any stabilizing agent, such as for example saccharides, trehalose, mannitol, saccharose and the like, to increase and/or maintain product shelf-life and/or to enhance stability.

In another aspect of the present disclosure, products resulting from the methods as described above are provided. In particular, the present disclosure relates to a composition of matter comprising recombinantly expressed PCV3 ORF protein. In some preferred forms, this composition of matter also comprises an agent suitable for the inactivation of viral vectors and comprises an agent, suitable for the inactivation of viral vectors. Such products are useful as immunogenic compositions that induce an immune response and, more preferably, confers protective immunity against the clinical signs of PCV3 infection. The composition generally comprises the polypeptide, or a fragment thereof, expressed by ORF1, ORF2, ORF3, or any combination of one or more of these ORFs of PCV3, as the antigenic component of the composition. Of course, it is understood that the PCV3 ORF polypeptide used in an immunogenic composition in accordance with the present disclosure can be derived in any fashion including isolation and purification, standard protein synthesis, and recombinant methodology.

Clinical signs of PCV3 infection occur both post weaning around 6-8 weeks of age, and in growers and finishers, 12 to 14 weeks of age, and sporadically in other age groups. Clinical signs include the appearance of extensive purplish red slightly raised blotches of various sizes and shapes over the chest, abdomen, thighs and forelegs. Over time the blotches become covered with dark crusts and then fade leaving scars. Additionally, pigs are depressed, may have an elevated fever, they are usually reluctant to move and eat, they lose weight, breathe heavily or have respiratory distress, oedema or fluid may be seen on the limbs and around the eyelids, superficial lymph nodes may be enlarged, their hair may become rough, their skin may become pale, they may exhibit jaundice, and some pigs have diarrhea. Although there is a high death rate overall, most pigs with skin lesions die. Further evidence of PCV3 infection can be found in the stomach and intestines where gastric ulcers and hemorrhage is present, fluid is present in the abdomen, lesions can be found in the lungs, tonsils, spleen, liver, and kidneys which are swollen, pale and mottled with many small hemorrhages showing through the surface.

Any PCV3 ORF would be effective as the source of the PCV3 ORF DNA and/or polypeptide as used herein. In preferred forms, the ORF DNA is ORF2. A preferred PCV3 ORF2 protein is that of SEQ ID NO. 6, but it is understood by those of skill in the art that this sequence, as well as those for ORF1 and ORF3 could vary by as much as 10% in sequence homology and still retain the antigenic characteristics that render it useful in immunogenic compositions. The antigenic characteristics of an immunological composition can be, for example, estimated by challenge experiments. Moreover, the antigenic characteristic of a modified antigen is still retained, when the modified antigen confers at least 70%, preferably 80%, more preferably 90% of the protective immunity as compared to the PCV3 ORF protein, encoded by the polynucleotide sequence of SEQ ID NOS: 3, 5, or 7. In some forms, immunogenic portions of a PCV3 ORF protein are used as the antigenic component in the composition. The term "immunogenic portion" as used herein refers to truncated and/or substituted forms, or fragments of PCV3 ORF2 protein and/or polynucleotide, respectively. Preferably, such truncated and/or substituted forms, or fragments will comprise at least 6 contiguous amino acids from the full-length ORF polypeptide. More preferably, the truncated or substituted forms, or fragments will have at least 10, more preferably at least 15, and still more preferably at least 19 contiguous amino acids from the full-length ORF polypeptide. It is further understood that such sequences may be a part of larger fragments or truncated forms. Preferably, such truncated or substituted forms, or fragments will comprise at least 18 contiguous nucleotides from the full-length ORF nucleotide sequence, e.g. of SEQ ID NOS: 3, 5, or 7. More preferably, the truncated or substituted forms, or fragments will have at least 30, more preferably at least 45, and still more preferably at least 57 contiguous nucleotides the full-length ORF nucleotide sequence.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homologous sequence comprises at least a stretch of 50, even more preferably 100, even more preferably 250, even more preferably 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

In a further aspect of the present disclosure, an immunogenic composition effective for lessening the severity of clinical symptoms associated with PCV3 infection comprising PCV3 ORF protein is provided. Preferably, the PCV3 ORF2 protein is selected from the group consisting of: 1) a polypeptide comprising the sequence of SEQ ID NO: 4, 6, 8, or any combination thereof; 2) any polypeptide that is at least 90% homologous to the polypeptide of 1); 3) any immunogenic portion of the polypeptides of 1) and/or 2); 4) the immunogenic portion of 3), comprising at least 10 contiguous amino acids included in the sequences of SEQ ID NO: 4, 6, or 8; 5) a polypeptide equivalent to (due to the degeneracy of the genetic code) one encoded by a DNA comprising the sequence of SEQ ID NO: 3, 5, or 7; 6) any polypeptide that is encoded by a polynucleotide that is at least 80% homologous to the polynucleotide of 5); 7) any immunogenic portion of the polypeptides encoded by the polynucleotide of 5) and/or 6); or 8) the immunogenic portion of 7), wherein the polynucleotide coding for said immunogenic portion comprises at least 30 contiguous nucleotides included in the sequences of SEQ ID NO: 3, 5, or 7.

In preferred forms, these immunogenic portions will have the immunogenic characteristics of PCV3 ORF protein that is encoded by the sequence of SEQ ID NO: 3, 5, or 7.

According to a further aspect, PCV3 ORF2 protein is provided in the immunological composition at an antigen inclusion level effective for inducing the desired immune response, namely reducing the incidence of or lessening the severity of clinical signs resulting from PCV3 infection. Preferably, the PCV3 ORF2 protein inclusion level is at least 0.2 µg antigen/ml of the final immunogenic composition (µg/ml), more preferably from about 0.2 to about 400 µg/ml.

The polypeptide is incorporated into a composition that can be administered to an animal susceptible to PCV3 infection. In preferred forms, the composition may also include additional components known to those of skill in the art (see also Remington's Pharmaceutical Sciences. (1990). 18th ed. Mack Publ., Easton).

Those of skill in the art will understand that the composition herein may incorporate known injectable, physiologically acceptable, sterile solutions. For preparing a ready-to-use solution for parenteral injection or infusion, aqueous isotonic solutions, such as e.g. saline or corresponding plasma protein solutions are readily available. In addition, the immunogenic and vaccine compositions of the present disclosure can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others. Suitable adjuvants, are those described above.

According to a further aspect, the immunogenic composition of the present disclosure further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic compositions described herein can further include one or more other immunomodulatory agents such as, e.g., interleukins, interferons, or other cytokines. The immunogenic compositions can also include Gentamicin and Merthiolate. In another preferred embodiment, the present disclosure contemplates vaccine compositions comprising from about 1 ug/ml to about 60 µg/ml of antibiotics, and more preferably less than about 30 µg/ml of antibiotics.

It will be found that the immunogenic compositions comprising recombinant PCV3 ORF protein as provided herewith are very effective in reducing the severity of or incidence of clinical signs associated with PCV3 infections up to and including the prevention of such signs.

Another aspect of the present disclosure relates to a kit. Generally the kit includes a container comprising at least one dose of the immunogenic composition of PCV3 ORF protein as provided herewith, wherein one dose comprises at least 2 µg PCV3 ORF protein. Said container can comprise from 1 to 250 doses of the immunogenic composition. In some preferred forms, the container contains 1, 10, 25, 50, 100, 150, 200, or 250 doses of the immunogenic composition of PCV3 ORF protein. Preferably, each of the containers comprising more than one dose of the immunogenic composition of PCV3 ORF protein further comprises an antimicrobiological active agent. Those agents are for example, antibiotics including Gentamicin and Merthiolate and the like. Thus, one aspect of the present disclosure relates to a container that comprises from 1 to 250 doses of the immunogenic composition of PCV3 ORF protein, wherein one dose comprises at least 2 µg PCV3 ORF protein, and Gentamicin and/or Merthiolate, preferably from about 1 µg/ml to about 60 µg/ml of antibiotics, and more preferably less than about 30 µg/ml. In preferred forms, the kit also includes an instruction manual, including the information for the intramuscular application of at least one dose of the immunogenic composition of PCV3 ORF protein into animals, preferably pigs and piglets to lessen the incidence and/or severity of clinical symptoms associated with PCV3 infection. Moreover, according to a further aspect, said instruction manual comprises the information of a second or further administration(s) of at least one dose of the immunogenic composition of PCV3 ORF2, wherein the second administration or any further administration is at least 14 days beyond the initial or any former administration. In some preferred forms, said instruction manual also includes the information, to administer an immune stimulant. Preferably, said immune stimulant shall be given at least twice. Preferably, at least 3, more preferably at least 5, and even more preferably at least 7 days are between the first and the second or any further administration of the immune stimulant. Preferably, the immune stimulant is given at least 10 days, preferably 15, even more preferably 20, and still even more preferably at least 22 days beyond the initial administration of the immunogenic composition of PCV3 ORF protein. It is understood that any immune stimulant known to a person skilled in the art can also be used. "Immune stimulant" as used herein, means any agent or composition that can trigger a general immune response, preferably without initiating or increasing a specific immune response, for example the immune response against a specific pathogen. It is further instructed to administer the immune stimulant in a suitable dose. The kit may also comprise a second container, including at least one dose of the immune stimulant.

A further aspect of the present disclosure relates to the kit as described above, comprising the immunogenic composition of PCV3 ORF as provided herewith and the instruction manual, wherein the instruction manual further includes the information to administer the PCV3 ORF immunogenic composition together, or around the same time as, with an immunogenic composition that comprises an additional antigen effective for reducing the severity of or incidence of clinical signs related to another porcine pathogen. Preferably, the manual contains the information of when the PCV3 ORF containing composition and the immunogenic composition that comprises an additional antigen are administered.

A further aspect, relates to the use of any of the compositions provided herewith as a medicament, preferably as a veterinary medicament, even more preferably as a vaccine. Moreover, the present disclosure also relates to the use of any of the compositions described herein, for the preparation of a medicament for lessening the severity of clinical symptoms associated with PCV3 infection. Preferably, the medicament is for the prevention of a PCV3 infection in swine, even more preferably in piglets.

A further aspect relates to a method for (1) the prevention of an infection, or re-infection with PCV3 or (2) the reduction in incidence or severity of or elimination of clinical symptoms caused by PCV3 in a subject, comprising administering any of the immunogenic compositions provided herewith to a subject in need thereof. Preferably, the subject is a pig. It is understood that the reduction is in comparison to a subject that has not received an administration of a composition of the present disclosure. Preferably, one dose or two doses of the immunogenic composition is/are administered, wherein one dose preferably comprises at least about 2 μg PCV3 ORF protein. A further aspect relates to the method of treatment as described above, wherein a second application of the immunogenic composition is administered. Preferably, the second administration is done with the same immunogenic composition, preferably having the same amount of PCV3 ORF protein. Preferably, the second administration is done at least 14 days beyond the initial administration, even more preferably at least 4 weeks beyond the initial administration. In preferred forms, the method is effective after just a single dose of the immunogenic composition and does not require a second or subsequent administration in order to confer the protective benefits upon the subject.

According to a further aspect, the present disclosure provides a multivalent combination vaccine which includes an immunological agent effective for reducing the incidence of or lessening the severity of PCV3 infection, and at least one immunological active component against another disease-causing organism in swine.

In particular the immunological agent effective for reducing the incidence of or lessening the severity of PCV3 infection is a PCV3 antigen. Preferably, said PCV3 antigen is a PCV3 ORF protein as provided herewith, or any immunogenic composition as described above, that comprises PCV3 ORF protein. The PCV3 ORF protein can be ORF1, ORF2, ORF3, or any combination thereof. For example, ORF1 in combination with ORF2, ORF2 in combination with ORF3, ORF 1 in combination with ORF3, and a combination of ORFs 1, 2, and 3, are each possible combinations of the PCV3 ORFs that could be combined in a single immunogenic composition. In preferred forms, the ORF is ORF2 or a combination including ORF2.

The terms "immunogenic protein", "immunogenic polypeptide" or "immunogenic amino acid sequence" as used herein refer to any amino acid sequence which elicits an immune response in a host against a pathogen comprising said immunogenic protein, immunogenic polypeptide or immunogenic amino acid sequence. An "immunogenic protein", "immunogenic polypeptide" or "immunogenic amino acid sequence" as used herein, includes the full-length sequence of any proteins, analogs thereof, or immunogenic fragments thereof. By "immunogenic fragment" is meant a fragment of a protein which includes one or more epitopes and thus elicits the immunological response against the relevant pathogen. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, Jun. 28-Jul. 3, 1998.

Preferably the other disease-causing organism in swine is selected from the group consisting of: *Actinobacillus pleuropneumonia*; Adenovirus; Alphavirus such as Eastern equine encephalomyelitis viruses; *Bordetella bronchiseptica; Brachyspira* spp., preferably *B. hyodyentheriae; B. piosicoli, Brucella suis*, preferably biovars 1, 2, and 3; Classical swine fever virus; *Clostridium* spp., preferably *Cl. difficile, Cl. perfringens* types A, B, and C, *Cl. novyi, Cl. septicum, Cl. tetani;* Coronavirus, preferably Porcine Respiratory Corona virus; *Eperythrozoonosis suis; Erysipelothrix rhsiopathiae; Escherichia coli; Haemophilus parasuis,* preferably subtypes 1, 7 and 14: Hemagglutinating encephalomyelitis virus; Japanese Encephalitis Virus; *Lawsonia intracellularis; Leptospira* spp.; preferably *Leptospira australis; Leptospira canicola; Leptospira grippotyphosa; Leptospira icterohaemorrhagicae;* and *Leptospira interrogans; Leptospira pomona; Leptospira tarassovi; Mycobacterium* spp. preferably *M. avium; M. intracellulare;* and *M. bovis; Mycoplasma hyopneumoniae* (M hyo); *Pasteurella multocida;* Porcine cytomegalovirus; Porcine Parvovirus; Porcine Reproductive and Respiratory Syndrome (PRRS) Virus; Pseudorabies virus; Rotavirus; *Salmonella* spp.; preferably *S. thyhimurium;* and *S. choleraesuis; Staph. hyicus; Staphylococcus* spp. preferably *Streptococcus* spp., preferably *Strep. suis;* Swine herpes virus; Swine Influenza Virus; Swine pox virus; Swine pox virus; Vesicular stomatitis virus; Virus of vesicular exanthema of swine; *Leptospira Hardjo;* and/or *Mycoplasma hyosynoviae.*

An "immunological active component" as used herein means a component that induces or stimulates the immune response in an animal to which said component is administered. According to a preferred embodiment, said immune response is directed to said component or to a microorganism comprising said component. According to a further preferred embodiment, the immunological active component is an attenuated microorganism, including modified live virus (MLV), a killed-microorganism or at least an immunological active part of a microorganism.

"Immunological active part of a microorganism" as used herein means a protein-, sugar-, and or glycoprotein containing fraction of a microorganism that comprises at least one antigen that induces or stimulates the immune response in an animal to which said component is administered. According to a preferred embodiment, said immune response is directed to said immunological active part of a microorganism or to a microorganism comprising said immunological active part.

In another aspect of the present disclosure, infectious chimeric DNA clones of porcine circovirus (PCV3) and live chimeric viruses derived from the DNA clones that are useful as vaccines are provided. The new live chimeric, genetically avirulent viruses are made from the nonpathogenic PCV1 genomic structure in which an immunogenic gene of a pathogenic PCV3 strain replaces a gene of the PCV1, typically in the same corresponding position. The disclosure encompasses the biologically functional plasmids, viral vectors and the like that contain the new recombinant nucleic acid molecules described herein, suitable host cells transfected by the vectors comprising the DNA and the immunogenic polypeptide expression products. Included within the scope of the present disclosure is a novel method of protecting pigs or providing a protective effect against viral infection or clinical signs described above and for postweaning multisystemic wasting syndrome (PMWS), pneumonia, reproductive failure, and porcine dermatitis and nephropathy syndrome (PDNS) caused by PCV3 comprising administering to a pig in need of such protection an immunologically effective amount of a vaccine comprising, for example, the cloned chimeric DNA in a plasmid, a chimeric virus derived from the chimeric DNA clone, the polypeptide products expressed from the DNA described herein, or any combination thereof. Another aspect of the disclosure is drawn to novel mutants of the PCV3 immunogenic capsid gene and protein, and the introduction of the mutations in the chimeric clones to facilitate cell culture growth and ensure vaccine safety. In yet another aspect, the disclosure provides new infectious PCV3 molecular DNA and reciprocal chimeric DNA clones of PCV that are useful as experimental models in obtaining or characterizing the novel avirulent viral vaccines.

In accordance with one aspect of the present disclosure, infectious molecular and chimeric nucleic acid molecules of porcine circovirus (PCV), live chimeric viruses produced from the chimeric nucleic acid molecule and veterinary vaccines to protect pigs from viral infection, pneumonia, reproductive failure, PMWS, and/or PDNS caused by PCV3 are provided. The disclosure further provides immunogenic polypeptide expression products that may be used as vaccines. The new avirulent, infectious chimeric DNA molecule of PCV (PCV1-3) comprises a nucleic acid molecule encoding an infectious, nonpathogenic PCV1 that contains an immunogenic open reading frame (ORF) gene of a pathogenic PCV3 in place of an ORF gene in the PCV1 genome. The infectious chimeric PCV1-3 DNA clone preferably contains the immunogenic capsid gene (ORF2) of the PCV3 DNA cloned in the genomic backbone of the infectious, nonpathogenic PCV1 DNA clone. Generally, the capsid gene of the PCV3 DNA replaces the ORF2 gene of the PCV1 DNA in the nonpathogenic PCV1 genomic structure but it is contemplated that a variety of positional permutations may be constructed through genetic engineering to obtain other avirulent or attenuated chimeric DNA clones. The reciprocal chimeric infectious PCV3-1 DNA clone between PCV1 and PCV3 is disclosed as a control to analyze the chimeric PCV1-3 clone of the disclosure and is constructed by replacing the capsid gene of PCV3 with that of PCV1 in the backbone of the pathogenic PCV3 infectious DNA clone. In addition to being an experimental model, the reciprocal chimeric PCV3-1 DNA clone may find use in making specially tailored vaccines.

In other forms, ORF3 of PCV3 can be substituted for the ORF2 or ORF3 of the PCV1-3 or PCV3-1 infectious clone. In still other preferred forms, ORF1 and ORF3 of PCV3 can be substituted for ORF2 of PCV3 of the PCV1-3 or PCV3-1 infectious clone.

The cloned genomic DNA of PCV3 described herein will be shown to be in vitro and in vivo infectious when transfected into PK-15 cells and given to pigs. The infectious PCV3 DNA clone will produce pathological lesions characteristic of PMWS and or PDNS in pigs allowing for an improved characterization of clinical disease and understanding of virus distribution in the tissue cells. This new, readily reproducible pathogenic agent lends itself to the development of a suitable vaccination program to prevent PMWS and or PDNS in pigs.

The novel chimeric PCV1-3 DNA clone will also be infectious by both in vitro transfection of PK-15 cells and in vivo administration to pigs. In transfected PK-15 cells, one preferred chimeric PCV1-3 DNA clone will express the PCV3 ORF2 capsid antigen (the immunogenic capsid protein of PCV3) whereas the reciprocal chimeric PCV3-1 DNA clone will express the PCV1 capsid antigen, which can be demonstrated by immunofluorescence assay (IFA) using antibodies specific to PCV1 or PCV3 capsid antigen. Seroconversion to PCV3-specific antibody will be detectable in pigs inoculated with the infectious PCV3 clone as well as the chimeric PCV1-3 clone. Detecting the seroconversion to PCV3-specific antibody will establish that the chimeric PCV1-3 DNA clone induces the PCV3-specific antibody in infected pigs and, consequently, will act to protect inoculated pigs from infection with PCV3.

Surprisingly and advantageously, the chimeric PCV1-3 infectious DNA clone having the immunogenic capsid gene (ORF2) of the pathogenic PCV3 cloned into the nonpathogenic PCV1 genomic backbone will induce a specific antibody response to the pathogenic PCV3 capsid antigen while it uniquely retains the nonpathogenic nature of PCV1 in pigs. Animals inoculated with the chimeric PCV1-3 infectious DNA clone will develop a mild infection resembling that of PCV1 inoculated animals while seroconverting to the antibody against the ORF2 capsid protein of the pathogenic PCV3. The average length of viremia observed in PCV1 and chimeric PCV1-3 inoculated animals will be shorter than that in pathogenic PCV3 inoculated animals. The lack of detectable chimeric PCV1-3 viremia in some inoculated animals will not affect seroconversion to antibody against PCV3 ORF2 capsid protein in the PCV1-3 inoculated pigs. The results will indicate that, even though the chimeric PCV1-3 viremia is short or undetectable in some inoculated animals, the chimeric PCV1-3 virus will be able to induce antibody response against PCV3 ORF2 capsid protein. The special ability of the chimeric PCV1-3 infectious DNA clone to induce the immune response specific to the pathogenic PCV3 immunogenic ORF2 capsid protein yet remain non-pathogenic to pigs will make the chimeric PCV1-3 clone(s) particularly useful as genetically engineered live-attenuated vaccine and other types of vaccines. Suitable cells containing the chimeric nucleic acid molecule will uniquely produce live, infectious chimeric porcine circoviruses. In some preferred forms, live, infectious chimeric virus will be derived from the chimeric DNA clone by transfecting PK-15 cells via in vitro and in vivo transfections. The disclosure further envisions that the chimeric virus is derived from the complementary strand or the nucleotide sequences having a high homology, at least 90%, more preferably 91, 92, 93, 94, 95, 96, 97, 98, or 99%, to the chimeric nucleotide sequence.

Also included within the scope of the present disclosure are biologically functional plasmids, viral vectors and the like that contain the new recombinant nucleic acid molecules described herein, suitable host cells transfected by the vectors comprising the chimeric and molecular DNA clones and the immunogenic polypeptide expression products. Some particularly preferred immunogenic proteins will have the amino acid sequence set forth in SEQ ID NO:4, 6, or 8. The biologically active variants thereof are further encompassed by the disclosure. One of ordinary skill in the art would know how to modify, substitute, delete, etc., amino acid(s) from the polypeptide sequence and produce biologically active variants that retain the same, or substantially the same, activity as the parent sequence without undue effort.

To produce the immunogenic polypeptide products of this disclosure, the process may include the following steps: growing, under suitable nutrient conditions, prokaryotic or eukaryotic host cells transfected with the new recombinant nucleic acid molecules described herein in a manner allowing expression of said polypeptide products, and isolating the desired polypeptide products of the expression of said nucleic acid molecules by standard methods known in the art. It is contemplated that the immunogenic proteins may be prepared by other techniques such as, for example, biochemical synthesis and the like.

Another embodiment of the present disclosure relates to novel mutations of the nucleotide and amino acid sequences of the PCV3 immunogenic capsid gene and protein. PCV3 is a causative agent of PMWS, PDNS, pneumonia, and reproductive failure whereas the PK-15 cell culture-derived porcine circovirus type I (PCV1) is nonpathogenic to pigs. A PCV1-3 vaccine containing the mutation may be further tested in cell culture by routine procedures to select the combination that facilitates cell culture growth or ensures improved safety measures when vaccinating pigs due to the further attenuation of PCV3 virulent properties, if any persist. While the benefit of the PCV1-3 chimera lies in its natural avirulent trait, the alternative use of the mutated PCV3 ORF2 to make the PCV1-3 chimera provides another embodiment of the present disclosure that is available if further safening of the natural live chimera vaccine becomes warranted.

Vaccines of the chimeric viral and molecular DNA clones, and methods of using them, are also included within the scope of the present disclosure. Inoculated pigs are protected from serious viral infection, pneumonia, reproductive failure, PDNS, and PMWS caused by PCV3. The novel method protects pigs in need of protection against viral infection, pneumonia, reproductive failure, PDNS, or PMWS by administering to the pig an immunologically effective amount of a vaccine according to the disclosure, such as, for example, a vaccine comprising an immunogenic amount of the chimeric PCV1-3 DNA, the cloned chimeric virus, a plasmid or viral vector containing the chimeric DNA of PCV1-3, the polypeptide expression products, the recombinant PCV3 DNA, etc. Other antigens such as those described above and immune stimulants may be given concurrently to the pig to provide a broad spectrum of protection against infections. Such concurrent administration can be provided in distinct and separate administrations or be combined into a single multivalent composition.

The vaccines comprise, for example, the infectious chimeric PCV1-3 DNA, the cloned PCV chimeric DNA genome in suitable plasmids or vectors such as, for example, the pSK vector, an avirulent, live chimeric virus, an inactivated chimeric virus, etc. in combination with a nontoxic, physiologically acceptable carrier and, optionally, one or more adjuvants, as described above. The vaccine may also comprise the infectious PCV3 molecular DNA clone described herein. The avirulent, live viral vaccine of the present disclosure provides an advantage over traditional viral vaccines that use either attenuated, live viruses which run the risk of reverting back to the virulent state or killed cell culture propagated whole virus which may not induce sufficient antibody immune response for protection against the viral disease.

Although the live viral vaccine has some advantages, other types of vaccines may be used to inoculate pigs with the new chimeric virus and other antigens described herein. To prepare inactivated virus vaccines, for instance, the virus propagation from the infectious DNA clone is done by methods known in the art or described herein. Serial virus inactivation is then optimized by protocols generally known to those of ordinary skill in the art.

Inactivated virus vaccines may be prepared by treating the isolated virus or the chimeric virus derived from the cloned PCV DNA with inactivating agents such as formalin or hydrophobic solvents, acids, etc., by irradiation with ultraviolet light or X-rays, by heating, etc. Inactivation is conducted in a manner understood in the art. The virus is considered inactivated if it is unable to infect a cell susceptible to infection.

To prepare attenuated vaccines from pathogenic clones, the tissue culture adapted, live, pathogenic PCV3 is first attenuated (rendered nonpathogenic or harmless) by methods known in the art, typically made by serial passage through cell cultures. Attenuation of pathogenic clones may also be made by gene deletions or viral-producing gene mutations. Then, the attenuated PCV3 viruses may be used to construct additional chimeric PCV1-3 viruses that retain the nonpathogenic phenotype of PCV1 but can vary in the strength of the immunogenicity traits selected from the PCV3 genome through recombinant technology.

The present disclosure also relates to vaccines comprising a nucleotide sequence of the genome of PCV3, SEQ ID No. 1, SEQ ID No. 3, SEQ ID No. 5, SEQ Id No. 7, or a homologue or fragment thereof, and an acceptable pharmaceutical or veterinary vehicle. In one embodiment of the disclosure, the nucleotide sequence is selected from, or a homologue or fragment thereof. In another embodiment of the disclosure, the homologue has at least 90% sequence identity to SEQ ID No. 2, SEQ ID No. 4, SEQ ID No. 6 or SEQ ID No. 8. In yet another embodiment, the vaccine further comprises an adjuvant.

A further aspect of the present disclosure relates to vaccines comprising a vector and an acceptable pharmaceutical or veterinary vehicle, the vector comprising a nucleotide sequence of the genome of PCV3, such as SEQ ID NO. 2, 4, 6, 8, or any combination thereof, or a homologue or fragment thereof.

The present disclosure also relates to vaccines immunogenic compositions comprising a cell and an acceptable pharmaceutical or veterinary carrier, wherein the cell is transformed with a nucleotide sequence of the genome of PCV3, or a homologue or fragment thereof.

Still further, the present disclosure relates to vaccines or immunogenic compositions comprising a pharmaceutically acceptable vehicle and a single polypeptide, wherein the single polypeptide consists of SEQ ID No. 2, 4, 6, or 8

Additionally, the present disclosure relates to methods of immunizing a mammal against PCV3 comprising administering to a mammal an effective amount of a vaccine or immu9nogenci composition described above.

The present disclosure relates to nucleotide sequences of the genome of PCV3 selected from the sequences SEQ ID No. 1, SEQ ID No. 3, SEQ ID No. 5, SEQ ID No. 7 or one of their fragments.

The present disclosure likewise relates to nucleotide sequences, characterized in that they are selected from: a) a nucleotide sequence of a specific fragment of the sequence SEQ ID No. 1, SEQ ID No. 3, SEQ ID No. 5, SEQ ID No. 7 or one of their fragments; b) a nucleotide sequence homologous to a nucleotide sequence such as defined in a); c) a nucleotide sequence complementary to a nucleotide sequence such as defined in a) or b), and a nucleotide sequence of their corresponding RNA; d) a nucleotide sequence capable of hybridizing under stringent conditions with a sequence such as defined in a), b) or c); e) a nucleotide sequence comprising a sequence such as defined in a), b), c) or d); and f) a nucleotide sequence modified by a nucleotide sequence such as defined in a), b), c), d) or e).

Nucleotide, polynucleotide or nucleic acid sequence will be understood according to the present disclosure as meaning both a double-stranded or single-stranded DNA in the monomeric and dimeric (so-called in tandem) forms and the transcription products of said DNAs.

It must be understood that the present disclosure does not relate to the genomic nucleotide sequences taken in their natural environment, that is to say in the natural state. It concerns sequences which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning and subcloning, it being possible for the sequences of the disclosure to be carried by vectors.

Complementary nucleotide sequence of a sequence of the disclosure is understood as meaning any DNA whose nucleotides are complementary to those of the sequence of the disclosure, and whose orientation is reversed (antiparallel sequence).

Hybridization under conditions of stringency with a nucleotide sequence according to the disclosure is understood as meaning a hybridization under conditions of temperature and ionic strength chosen in such a way that they allow the maintenance of the hybridization between two fragments of complementary DNA.

Among the nucleotide sequences according to the disclosure, those are likewise preferred which can be used as a primer or probe in methods allowing the homologous sequences according to the disclosure to be obtained, these methods, such as the polymerase chain reaction (PCR), nucleic acid cloning and sequencing, being well known to the person skilled in the art.

Among said nucleotide sequences according to the disclosure, those are again preferred which can be used as a primer or probe in methods allowing the presence of PCV3 or one of its variants such as defined below to be diagnosed.

The nucleotide sequences according to the disclosure capable of modulating, of inhibiting or of inducing the expression of PCV3 gene, and/or capable of modulating the replication cycle of PCV3 in the host cell and/or organism are likewise preferred. Replication cycle will be understood as designating the invasion and the multiplication of PCV3, and its propagation from host cell to host cell in the host organism.

Among said nucleotide sequences according to the disclosure, those corresponding to open reading frames, called ORF sequences, and coding for polypeptides, such as, for example, the sequences SEQ ID No. 4 (ORF1), SEQ ID No. 6 (ORF2) and SEQ ID No. 8 (ORF3) respectively. The nucleotide sequence fragments according to the disclosure can be obtained, for example, by specific amplification, such as PCR, or after digestion with appropriate restriction enzymes of nucleotide sequences according to the disclosure, these methods in particular being described in the work of Sambrook et al., 1989. Said representative fragments can likewise be obtained by chemical synthesis when their size is not very large and according to methods well known to persons skilled in the art.

Modified nucleotide sequence will be understood as meaning any nucleotide sequence obtained by mutagenesis according to techniques well known to the person skilled in the art, and containing modifications with respect to the normal sequences according to the disclosure, for example mutations in the regulatory and/or promoter sequences of polypeptide expression, especially leading to a modification of the rate of expression of said polypeptide or to a modulation of the replicative cycle.

Modified nucleotide sequence will likewise be understood as meaning any nucleotide sequence coding for a modified polypeptide such as defined below.

The present disclosure relates to nucleotide sequences of PCV3 according to the disclosure, characterized in that they are selected from the sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8, or one of their fragments.

The disclosure likewise relates to nucleotide sequences characterized in that they comprise a nucleotide sequence selected from: a) a nucleotide sequence SEQ ID No. 1, SEQ ID No. 3, SEQ ID No. 5, SEQ ID No. 7, SEQ ID No. 9, or one of their fragments; b) a nucleotide sequence of a specific fragment of a sequence such as defined in a); c) a homologous nucleotide sequence having at least 80% identity with a sequence such as defined in a) or b); d) a complementary nucleotide sequence or sequence of RNA corresponding to a sequence such as defined in a), b) or c); and e) a nucleotide sequence modified by a sequence such as defined in a), b), c) or d).

As far as homology with the nucleotide sequences SEQ ID No. 1, SEQ ID No. 3, SEQ ID No. 5, SEQ ID No. 7, or one of their fragments is concerned, the homologous, especially specific, sequences having a percentage identity with one of the sequences SEQ ID No. 1, SEQ ID No. 3, SEQ ID No. 5, SEQ ID No. 7, or one of their fragments of at least 80%, preferably 90% or 95%, are preferred. Said specific homologous sequences can comprise, for example, the sequences corresponding to the sequences ORF1, ORF2, ORF3, of PCV3. In the same manner, these specific homologous sequences can correspond to variations linked to mutations within strains of PCV3 and especially correspond to truncations, substitutions, deletions and/or additions of at least one nucleotide.

The disclosure comprises the polypeptides encoded by a nucleotide sequence according to the disclosure, preferably a polypeptide whose sequence is represented by a fragment, especially a specific fragment, these six amino acid sequences corresponding to the polypeptides which can be encoded according to one of the three possible reading frames of the sequence SEQ ID No. 1 or of the sequence SEQ ID No. 2.

The disclosure likewise relates to the polypeptides, characterized in that they comprise a polypeptide selected from the amino acid sequences SEQ ID No. 2, SEQ ID No. 4, SEQ ID No. 6, SEQ ID No. 8, or one of their fragments.

The disclosure also relates to the polypeptides, characterized in that they comprise a polypeptide selected from: a) a specific fragment of at least 5 amino acids of a polypeptide of an amino acid sequence according to the disclosure; b) a polypeptide homologous to a polypeptide such as defined in a); c) a specific biologically active fragment of a polypeptide such as defined in a) or b); and d) a polypeptide modified by a polypeptide such as defined in a), b) or c).

Among the polypeptides according to the disclosure, the polypeptides of amino acid sequences SEQ ID No. 2, SEQ ID No. 4, SEQ ID No. 6 and SEQ ID No. 8 are also preferred, these polypeptides being especially capable of specifically recognizing the antibodies produced during infection by the PCV3. These polypeptides thus have epitopes specific for the PCV3 and can thus be used in particular in the diagnostic field or as immunogenic agent to confer protection in pigs against infection by PCV3.

In the present description, the terms polypeptide, peptide and protein are interchangeable.

It must be understood that the disclosure does not relate to the polypeptides in natural form, that is to say that they are not taken in their natural environment but that they can be isolated or obtained by purification from natural sources, or else obtained by genetic recombination, or alternatively by chemical synthesis and that they can thus contain unnatural amino acids, as will be described below.

Polypeptide fragment according to the disclosure is understood as designating a polypeptide containing at least 5 consecutive amino acids, preferably 10 consecutive amino acids or 15 consecutive amino acids.

In the present disclosure, specific polypeptide fragment is understood as designating the consecutive polypeptide fragment encoded by a specific fragment nucleotide sequence according to the disclosure.

Homologous polypeptide will be understood as designating the polypeptides having, with respect to the natural polypeptide, certain modifications such as, in particular, a deletion, addition or substitution of at least one amino acid, a truncation, a prolongation, a chimeric fusion, and/or a mutation. Among the homologous polypeptides, those are preferred whose amino acid sequence has at least 80%, preferably 90%, homology with the sequences of amino acids of polypeptides according to the disclosure.

Specific homologous polypeptide will be understood as designating the homologous polypeptides such as defined above and having a specific fragment of polypeptide according to the disclosure.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following. These equivalent amino acids can be determined either by depending on their structural homology with the amino acids which they substitute, or on results of comparative tests of biological activity between the different polypeptides, which are capable of being carried out. By way of example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine etc., the reverse substitutions naturally being envisageable under the same conditions.

The specific homologous polypeptides likewise correspond to polypeptides encoded by the specific homologous nucleotide sequences such as defined above and thus comprise in the present definition the polypeptides which are mutated or correspond to variants which can exist in PCV3, and which especially correspond to truncations, substitutions, deletions and/or additions of at least one amino acid residue.

Specific biologically active fragment of a polypeptide according to the disclosure will be understood in particular as designating a specific polypeptide fragment, such as defined above, having at least one of the characteristics of polypeptides according to the disclosure, especially in that it is: capable of inducing an immunogenic reaction directed against a PCV3; and/or capable of being recognized by a specific antibody of a polypeptide according to the disclosure; and/or capable of linking to a polypeptide or to a nucleotide sequence of PCV3; and/or capable of exerting a physiological activity, even partial, such as, for example, a dissemination or structural (capsid) activity; and/or capable of modulating, of inducing or of inhibiting the expression of PCV3 gene or one of its variants, and/or capable of modulating the replication cycle of PCV3 in the cell and/or the host organism.

The polypeptide fragments according to the disclosure can correspond to isolated or purified fragments naturally present in a PCV3 or correspond to fragments which can be obtained by cleavage of said polypeptide by a proteolytic enzyme, such as trypsin or chymotrypsin or collagenase, or by a chemical reagent, such as cyanogen bromide (CNBr) or alternatively by placing said polypeptide in a very acidic environment, for example at pH 2.5. Such polypeptide fragments can likewise just as easily be prepared by chemical synthesis, from hosts transformed by an expression vector according to the disclosure containing a nucleic acid allowing the expression of said fragments, placed under the control of appropriate regulation and/or expression elements.

"Modified polypeptide" of a polypeptide according to the disclosure is understood as designating a polypeptide obtained by genetic recombination or by chemical synthesis as will be described below, having at least one modification with respect to the normal sequence. These modifications will especially be able to bear on amino acids at the origin of a specificity, of pathogenicity and/or of virulence, or at the origin of the structural conformation, and of the capacity of membrane insertion of the polypeptide according to the disclosure. It will thus be possible to create polypeptides of equivalent, increased or decreased activity, and of equivalent, narrower, or wider specificity. Among the modified polypeptides, it is necessary to mention the polypeptides in which up to 5 amino acids can be modified, truncated at the N- or C-terminal end, or even deleted or added.

As is indicated, the modifications of the polypeptide will especially have as objective: to render it capable of modulating, of inhibiting or of inducing the expression of PCV3 gene and/or capable of modulating the replication cycle of PCV3 in the cell and/or the host organism, of allowing its incorporation into vaccine compositions, and/or of modifying its bioavailability as a compound for therapeutic use.

The methods allowing said modulations on eukaryotic or prokaryotic cells to be demonstrated are well known to the person skilled in the art. It is likewise well understood that it will be possible to use the nucleotide sequences coding for said modified polypeptides for said modulations, for example through vectors according to the disclosure and described below, in order, for example, to prevent or to treat the pathologies linked to the infection.

The preceding modified polypeptides can be obtained by using combinatorial chemistry, in which it is possible to systematically vary parts of the polypeptide before testing them on models, cell cultures or microorganisms for example, to select the compounds which are most active or have the properties sought.

Chemical synthesis likewise has the advantage of being able to use unnatural amino acids, or nonpeptide bonds. Thus, in order to improve the duration of life of the polypeptides according to the disclosure, it may be of interest to u se unnatural amino acids, for example in D form, or else amino acid analogs, especially sulfur-containing forms, for example.

Finally; it will be possible to integrate the structure of the polypeptides according to the disclosure, its specific or modified homologous forms, into chemical structures of polypeptide type or others. Thus, it may be of interest to provide at the N- and C-terminal ends compounds not recognized by the proteases.

The nucleotide sequences coding for a polypeptide according to the disclosure are likewise part of the disclosure.

The disclosure likewise relates to nucleotide sequences utilizable as a primer or probe, characterized in that said sequences are selected from the nucleotide sequences according to the disclosure.

The cloning and the sequencing of the PCV3 has allowed it to be identified, after comparative analysis with the nucleotide sequences of other porcine circoviruses, that, among the sequences of fragments of these nucleic acids, were those which are strictly specific to the PCV3 and those which correspond to a consensus sequence of porcine circoviruses other than the PCV3. There is likewise a great need for nucleotide sequences utilizable as a primer or probe specific to the whole of the other known and nonpathogenic porcine circoviruses.

It is well understood that the present disclosure likewise relates to specific polypeptides of known porcine circoviruses other than PCV3, encoded by said consensus nucleotide sequences, capable of being obtained by purification from natural polypeptides, by genetic recombination or by chemical synthesis by procedures well known to the person skilled in the art and such as described in particular below. In the same manner, the labeled or unlabeled mono- or polyclonal antibodies directed against said specific polypeptides encoded by said consensus nucleotide sequences are also part of the disclosure.

It will be possible to use said consensus nucleotide sequences, said corresponding polypeptides as well as said antibodies directed against said polypeptides in procedures or sets for detection and/or identification such as described below, in place of or in addition to nucleotide sequences, polypeptides or antibodies according to the disclosure, specific to PCV3 type A and/or B.

These protocols have been improved for the differential detection of the circular monomeric forms of specific replicative forms of the virion or of the DNA in replication and the dimeric forms found in so-called in-tandem molecular constructs.

The disclosure additionally relates to the use of a nucleotide sequence according to the disclosure as a primer or probe for the detection and/or the amplification of nucleic acid sequences.

The nucleotide sequences according to the disclosure can thus be used to amplify nucleotide sequences, especially by the PCR technique (polymerase chain reaction) (Erlich, 1989; Innis et al., 1990; Rolfs et al., 1991; and White et al., 1997). These oligodeoxyribonucleotide or oligoribonucleotide primers advantageously have a length of at least 8 nucleotides, preferably of at least 12 nucleotides, and even more preferentially at least 20 nucleotides. Other amplification techniques of the target nucleic acid can be advantageously employed as alternatives to PCR.

The nucleotide sequences of the disclosure, in particular the primers according to the disclosure, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); the TMA technique (Transcription Mediated Amplification).

The polynucleotides of the disclosure can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al. as well as by Stone et al. in 1996.

In the case where the target polynucleotide to be detected is possibly an RNA, for example an MRNA, it will be possible to use, prior to the employment of an amplification reaction with the aid of at least one primer according to the disclosure or to the employment of a detection procedure with the aid of at least one probe of the disclosure, an enzyme of reverse transcriptase type in order to obtain a cDNA from the RNA contained in the biological sample. The cDNA obtained will thus serve as a target for the primer(s) or the probe(s) employed in the amplification or detection procedure according to the disclosure.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

The disclosure also comprises the nucleotide sequences utilizable as a probe or primer according to the disclosure, characterized in that they are labeled with a radioactive compound or with a nonradioactive compound. The unlabeled nucleotide sequences can be used directly as probes or primers, although the sequences are generally labeled with a radioactive element ($^{32}$P, $^{35}$S, $^{3}$H, $^{125}$I) or with a nonradioactive molecule (biotin, acetylaminofluorene, digoxigenin, 5-bromodeoxyuridine, fluorescein) to obtain probes which are utilizable for numerous applications. Examples of nonradioactive labeling of nucleotide sequences are described, for example, in French Patent No. 78.10975 or by Urdea et al. or by Sanchez-Pescador et al. in 1988. In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The disclosure likewise comprises the nucleotide sequences according to the disclosure, characterized in that they are immobilized on a support, covalently or noncovalently.

According to another advantageous mode of employing nucleotide sequences according to the disclosure, the latter can be used immobilized on a support and can thus serve to capture, by specific hybridization, the target nucleic acid obtained from the biological sample to be tested. If necessary, the solid support is separated from the sample and the hybridization complex formed between said capture probe and the target nucleic acid is then detected with the aid of a second probe, a so-called detection probe, labeled with an easily detectable element.

Another subject of the present disclosure is a vector for the cloning and/or expression of a sequence, characterized in that it contains a nucleotide sequence according to the disclosure.

The vectors according to the disclosure, characterized in that they contain the elements allowing the expression and/or the secretion of said nucleotide sequences in a determined host cell, are likewise part of the disclosure. The vector must then contain a promoter, signals of initiation and termination of translation, as well as appropriate regions of regulation of transcription. It must be able to be maintained stably in the host cell and can optionally have particular signals specifying the secretion of the translated protein. These different elements are chosen as a function of the host cell used. To this end, the nucleotide sequences according to the disclosure can be inserted into autonomous replication vectors within the chosen host, or integrated vectors of the chosen host. Such vectors will be prepared according to the methods currently used by the person skilled in the art, and it will be possible to introduce the clones resulting therefrom into an appropriate host by standard methods, such as, for example, lipofection, electroporation and thermal shock. The vectors according to the disclosure are, for example, vectors of plasmid or viral origin. A preferred vector for the expression of polypeptides of the disclosure is baculovirus.

These vectors are useful for transforming host cells in order to clone or to express the nucleotide sequences of the disclosure. The disclosure likewise comprises the host cells transformed by a vector according to the disclosure. These cells can be obtained by the introduction into host cells of a nucleotide sequence inserted into a vector such as defined above, then the culturing of said cells under conditions allowing the replication and/or expression of the transfected nucleotide sequence. The host cell can be selected from prokaryotic or eukaryotic systems, such as, for example, bacterial cells (Olins and Lee, 1993), but likewise yeast cells (Buckholz, 1993), as well as animal cells, in particular the cultures of mammalian cells (Edwards and Aruffo, 1993), and especially Chinese hamster ovary (CHO) cells, but likewise the cells of insects in which it is possible to use procedures employing baculoviruses, for example (Luckow, 1993). A preferred host cell for the expression of the proteins of the disclosure is constituted by sf9 insect cells.

The disclosure likewise relates to animals comprising one of said transformed cells according to the disclosure. The obtainment of transgenic animals according to the disclosure overexpressing one or more of the genes of PCV3 or part of the genes will be preferably carried out in rats, mice or rabbits according to methods well known to the person skilled in the art, such as by viral or nonviral transfections. It will be possible to obtain the transgenic animals overexpressing one or more of said genes by transfection of multiple copies of said genes under the control of a strong promoter of ubiquitous nature, or selective for one type of tissue. It will likewise be possible to obtain the transgenic animals by homologous recombination in embryonic cell strains, transfer of these cell strains to embryos, selection of the affected chimeras at the level of the reproductive lines, and growth of said chimeras. The transformed cells as well as the transgenic animals according to the disclosure are utilizable in procedures for preparation of recombinant polypeptides.

It is today possible to produce recombinant polypeptides in relatively large quantity by genetic engineering using the cells transformed by expression vectors according to the disclosure or using transgenic animals according to the disclosure. The procedures for preparation of a polypeptide of the disclosure in recombinant form, characterized in that they employ a vector and/or a cell transformed by a vector according to the disclosure and/or a transgenic animal comprising one of said transformed cells according to the disclosure, are themselves comprised in the present disclosure. Among said procedures for preparation of a polypeptide of the disclosure in recombinant form, the preparation procedures employing a vector, and/or a cell transformed by said vector and/or a transgenic animal comprising one of said transformed cells, containing a nucleotide sequence according to the disclosure coding for a polypeptide of PCV3, are preferred. The recombinant polypeptides obtained as indicated above can just as well be present in glycosylated form as in nonglycosylated form and can or cannot have the natural tertiary structure.

A preferred variant consists in producing a recombinant polypeptide used to a "carrier" protein (chimeric protein). The advantage of this system is that it allows a stabilization of and a decrease in the proteolysis of the recombinant product, an increase in the solubility in the course of renaturation in vitro and/or a simplification of the purification when the fusion partner has an affinity for a specific ligand.

More particularly, the disclosure relates to a procedure for preparation of a polypeptide of the disclosure comprising the following steps: a) culture of transformed cells under conditions allowing the expression of a recombinant polypeptide of nucleotide sequence according to the disclosure; b) if need be, recovery of said recombinant polypeptide.

When the procedure for preparation of a polypeptide of the disclosure employs a transgenic animal according to the disclosure, the recombinant polypeptide is then extracted from said animal.

The disclosure also relates to a polypeptide which is capable of being obtained by a procedure of the disclosure such as described previously.

The disclosure also comprises a procedure for preparation of a synthetic polypeptide, characterized in that it uses a sequence of amino acids of polypeptides according to the disclosure. The disclosure likewise relates to a synthetic polypeptide obtained by a procedure according to the disclosure.

The polypeptides according to the disclosure can likewise be prepared by techniques which are conventional in the field of the synthesis of peptides. This synthesis can be carried out in homogeneous solution or in solid phase. For example, reference can be made to the technique of synthesis in homogeneous solution described by Houben-Weyl in 1974. This method of synthesis consists in successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides. According to another preferred technique of the disclosure, recourse will be made to the technique described by Merrifield. To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids which are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The disclosure additionally relates to hybrid polypeptides having at least one polypeptide according to the disclosure, and a sequence of a polypeptide capable of inducing an immune response in man or animals.

Advantageously, the antigenic determinant is such that it is capable of inducing a humoral and/or cellular response. It will be possible for such a determinant to comprise a polypeptide according to the disclosure in glycosylated form used with a view to obtaining immunogenic compositions capable of inducing the synthesis of antibodies directed against multiple epitopes. Said polypeptides or their glycosylated fragments are likewise part of the disclosure. These hybrid molecules can be formed, in part, of a polypeptide carrier molecule or of fragments thereof according to the disclosure, associated with a possibly immunogenic part, in particular an epitope of the diphtheria toxin, the tetanus toxin, a surface antigen of the hepatitis B virus (patent FR 79 21811), the VP1 antigen of the poliomyelitis virus or any other viral or bacterial toxin or antigen. The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984. Said hybrid nucleotide sequences coding for a hybrid polypeptide as well as the hybrid polypeptides according to the disclosure characterized in that they are recombinant polypeptides obtained by the expression of said hybrid nucleotide sequences are likewise part of the disclosure.

The disclosure likewise comprises the vectors characterized in that they contain one of said hybrid nucleotide sequences. The host cells transformed by said vectors, the transgenic animals comprising one of said transformed cells as well as the procedures for preparation of recombinant polypeptides using said vectors, said transformed cells and/or said transgenic animals are, of course, likewise part of the disclosure.

The polypeptides according to the disclosure, the antibodies according to the disclosure described below and the nucleotide sequences according to the disclosure can advantageously be employed in procedures for the detection and/or identification of PCV3, or of porcine circovirus other than a PCV3, in a biological sample (biological tissue or fluid) capable of containing them. These procedures, according to the specificity of the polypeptides, the antibodies and the nucleotide sequences according to the disclosure which will be used, will in particular be able to detect and/or to identify a PCV3 or a porcine circovirus other than a PCV3 or other than the PCV3.

The polypeptides according to the disclosure can advantageously be employed in a procedure for the detection and/or the identification of PCV3 in a biological sample (biological tissue or fluid) capable of containing them, characterized in that it comprises the following steps: a) contacting of this biological sample with a polypeptide or one of its fragments according to the disclosure (under conditions allowing an immunological reaction between said polypeptide and the antibodies possibly present in the biological sample); and b) demonstration of the antigen-antibody complexes possibly formed. Preferably, the biological sample is formed by a fluid, for example a pig serum, whole blood or biopsies. Any conventional procedure can be employed for carrying out such a detection of the antigen-antibody complexes possibly formed. By way of example, a preferred method brings into play immunoenzymatic processes according to the ELISA technique, by immunofluorescence, or radioimmunological processes (RIA) or their equivalent.

Thus, the disclosure likewise relates to the polypeptides according to the disclosure, labeled with the aid of an adequate label such as of the enzymatic, fluorescent or radioactive type. Such methods comprise, for example, the following steps: 1) deposition of determined quantities of a polypeptide composition according to the disclosure in the wells of a microtiter plate; 2) introduction into said wells of increasing dilutions of serum, or of a biological sample other than that defined previously, having to be analyzed; 3) incubation of the microplate; and 4) introduction into the wells of the microtiter plate of labeled antibodies directed against pig immunoglobulins, the labeling of these antibodies having been carried out with the aid of an enzyme selected from those which are capable of hydrolyzing a substrate by modifying the absorption of the radiation of the latter, at least at a determined wavelength, for example at 550 nm, detection, by comparison with a control test, of the quantity of hydrolyzed substrate.

The disclosure likewise relates to a kit or set for the detection and/or identification of PCV3, characterized in that it comprises the following elements: 1) a polypeptide according to the disclosure; 2) if need be, the reagents for the formation of the medium favorable to the immunological or specific reaction; 3) if need be, the reagents allowing the detection of the antigen-antibody complexes produced by the immunological reaction between the polypeptide(s) of the disclosure and the antibodies possibly present in the biological sample, these reagents likewise being able to carry a label, or to be recognized in their turn by a labeled reagent, more particularly in the case where the polypeptide according to the disclosure is not labeled; 4) if need be, a biological reference sample (negative control) devoid of antibodies recognized by a polypeptide according to the disclosure; and 5) if need be, a biological reference sample (positive control) containing a predetermined quantity of antibodies recognized by a polypeptide according to the disclosure.

The polypeptides according to the disclosure allow monoclonal or polyclonal antibodies to be prepared which are characterized in that they specifically recognize the polypeptides according to the disclosure. It will advantageously be possible to prepare the monoclonal antibodies from hybridomas according to the technique described by Kohler and Milstein in 1975. It will be possible to prepare the polyclonal antibodies, for example, by immunization of an animal, in particular a mouse, with a polypeptide or a DNA, according to the disclosure, associated with an adjuvant of the immune response, and then purification of the specific antibodies contained in the serum of the immunized animals on an affinity column on which the polypeptide which has served as an antigen has previously been immobilized. The polyclonal antibodies according to the disclosure can also be prepared by purification, on an affinity column on which a polypeptide according to the disclosure has previously been immobilized, of the antibodies contained in the serum of pigs infected by a PCV3.

The disclosure likewise relates to mono- or polyclonal antibodies or their fragments, or chimeric antibodies, characterized in that they are capable of specifically recognizing a polypeptide according to the disclosure. It will likewise be possible for the antibodies of the disclosure to be labeled in the same manner as described previously for the nucleic probes of the disclosure, such as a labeling of enzymatic, fluorescent or radioactive type.

The disclosure is additionally directed at a procedure for the detection and/or identification of PCV3, in a biological sample, characterized in that it comprises the following steps: a) contacting of the biological sample (biological tissue or fluid) with a mono- or polyclonal antibody according to the disclosure (under conditions allowing an immunological reaction between said antibodies and the polypeptides of PCV3, including ORF1, ORF2, and/or ORF3, possibly present in the biological sample); and b) demonstration of the antigen-antibody complex possibly formed.

Likewise within the scope of the disclosure is a kit or set for the detection and/or identification of PCV3, characterized in that it comprises the following components: a) a polyclonal or monoclonal antibody according to the disclosure, if need be labeled; b) if need be, a reagent for the formation of the medium favorable to the carrying out of the immunological reaction; c) if need be, a reagent allowing the detection of the antigen-antibody complexes produced by the immunological reaction, this reagent likewise being able to carry a label, or being capable of being recognized in its turn by a labeled reagent, more particularly in the case where said monoclonal or polyclonal antibody is not labeled; and d) if need be, reagents for carrying out the lysis of cells of the sample tested.

The present disclosure likewise relates to a procedure for the detection and/or the identification of PCV3 in a biological sample, characterized in that it employs a nucleotide sequence according to the disclosure. More particularly, the disclosure relates to a procedure for the detection and/or the identification of PCV3, in a biological sample, characterized in that it contains the following steps: a) if need be, isolation of the DNA from the biological sample to be analyzed; b) specific amplification of the DNA of the sample with the aid of at least one primer, or a pair of primers, according to the disclosure; and c) demonstration of the amplification products. These can be detected, for example, by the technique of molecular hybridization utilizing a nucleic probe according to the disclosure. This probe will advantageously be labeled with a nonradioactive (cold probe) or radioactive element.

For the purposes of the present disclosure, "DNA of the biological sample" or "DNA contained in the biological sample" will be understood as meaning either the DNA present in the biological sample considered, or possibly the cDNA obtained after the action of an enzyme of reverse transcriptase type on the RNA present in said biological sample.

Another aim of the present disclosure consists in a procedure according to the disclosure, characterized in that it comprises the following steps: a) contacting of a nucleotide probe according to the disclosure with a biological sample, the DNA contained in the biological sample having, if need be, previously been made accessible to hybridization under conditions allowing the hybridization of the probe with the DNA of the sample; and b) demonstration of the hybrid formed between the nucleotide probe and the DNA of the biological sample.

The present disclosure also relates to a procedure according to the disclosure, characterized in that it comprises the following steps: a) contacting of a nucleotide probe immobilized on a support according to the disclosure with a biological sample, the DNA of the sample having, if need be, previously been made accessible to hybridization, under conditions allowing the hybridization of the probe with the DNA of the sample; b) contacting of the hybrid formed between the nucleotide probe immobilized on a support and the DNA contained in the biological sample, if need be after elimination of the DNA of the biological sample which has not hybridized with the probe, with a nucleotide probe labeled according to the disclosure; and c) demonstration of the novel hybrid formed in step b). According to an advantageous embodiment of the procedure for detection and/or identification defined previously, this is characterized in that, prior to step a), the DNA of the biological sample is first amplified with the aid of at least one primer according to the disclosure.

The disclosure is additionally directed at a kit or set for the detection and/or the identification of PCV3, characterized in that it comprises the following elements: a) a nucleotide probe according to the disclosure; b) if need be, the reagents necessary for the carrying out of a hybridization reaction; and c) if need be, at least one primer according to the disclosure as well as the reagents necessary for an amplification reaction of the DNA.

The disclosure likewise relates to a kit or set for the detection and/or the identification of PCV3 or of porcine circovirus other than the PCV3, characterized in that it comprises the following components: a) a nucleotide probe, called a capture probe, according to the disclosure; b) an oligonucleotide probe, called a revealing probe, according to the disclosure, and c) if need be, at least one primer according to the disclosure, as well as the reagents necessary for an amplification reaction of the DNA.

The disclosure also relates to a kit or set for the detection and/or identification of PCV3, characterized in that it comprises the following elements: a) at least one primer according to the disclosure; b) if need be, the reagents necessary for carrying out a DNA amplification reaction; and c) if need be, a component allowing the sequence of the amplified fragment to be verified, more particularly an oligonucleotide probe according to the disclosure.

The disclosure additionally relates to the use of a nucleotide sequence according to the disclosure, of a polypeptide according to the disclosure, of an antibody according to the disclosure, of a cell according to the disclosure, and/or of an animal transformed according to the disclosure, for the selection of an organic or inorganic compound capable of modulating, inducing or inhibiting the expression of genes, and/or of modifying the cellular replication of PCV3 or capable of inducing or of inhibiting the pathologies including reducing the incidence of and severity of clinical signs linked to an infection by a PCV3.

The disclosure likewise comprises a method of selection of compounds capable of binding to a polypeptide or one of its fragments according to the disclosure, capable of binding to a nucleotide sequence according to the disclosure, or capable of recognizing an antibody according to the disclosure, and/or capable of modulating, inducing or inhibiting the expression of genes, and/or of modifying the cellular replication of PCV3 or capable of inducing or inhibiting the pathologies including reducing the incidence of and severity of clinical signs linked to an infection by a PCV3, characterized in that it comprises the following steps: a) contacting of said compound with said polypeptide, said nucleotide sequence, or with a cell transformed according to the disclosure and/or administration of said compound to an animal transformed according to the disclosure; and b) determination of the capacity of said compound to bind to said polypeptide or said nucleotide sequence, or to modulate, induce or inhibit the expression of genes, or to modulate the growth or the replication of PCV3, or to induce or inhibit in said transformed animal the pathologies linked to an infection by PCV3 (designated activity of said compound). The compounds capable of being selected can be organic compounds such as polypeptides or carbohydrates or any other organic or inorganic compounds already known, or novel organic compounds elaborated by molecular modelling techniques and obtained by chemical or biochemical synthesis, these techniques being known to the person skilled in the art. It will be possible to use said selected compounds to modulate the cellular replication of PCV3 and thus to control infection by this virus, the methods allowing said modulations to be determined being well known to the person skilled in the art. This modulation can be carried out, for example, by an agent capable of binding to a protein and thus of inhibiting or of potentiating its biological activity, or capable of binding to an envelope protein of the external surface of said virus and of blocking the penetration of said virus into the host cell or of favoring the action of the immune system of the infected organism directed against said virus. This modulation can likewise be carried out by an agent capable of binding to a nucleotide sequence of a DNA of said virus and of blocking, for example, the expression of a polypeptide whose biological or structural activity is necessary for the replication or for the proliferation of said virus host cells to host cells in the host animal.

The disclosure relates to the compounds capable of being selected by a selection method according to the disclosure.

The disclosure likewise relates to a pharmaceutical composition comprising a compound selected from the following compounds: a) a nucleotide sequence according to the disclosure; b) a polypeptide according to the disclosure; c) a vector, a viral particle or a cell transformed according to the disclosure; d) an antibody according to the disclosure; and e) a compound capable of being selected by a selection method according to the disclosure; possibly in combination with a pharmaceutically acceptable carrier and, if need be, with one or more adjuvants of the appropriate immunity.

The disclosure also relates to an immunogenic and/or vaccine composition, characterized in that it comprises a compound selected from the following compounds: a) a nucleotide sequence according to the disclosure; b) a polypeptide according to the disclosure; c) a vector or a viral particle according to the disclosure; and d) a cell according to the disclosure.

In one embodiment, the vaccine composition according to the disclosure is characterized in that it comprises a mixture of at least two of said compounds a), b), c) and d) above and in that one of the two said compounds is related to the PCV3.

In another embodiment of the disclosure, the vaccine composition is characterized in that it comprises at least one compound a), b), c), or d) above which is related to PCV3. In still another embodiment, the vaccine composition is characterized in that it comprises at least one compound a), b), c), or d) above which is related to PCV3 ORF2.

A compound related to the PCV3 is understood here as respectively designating a compound obtained from the genomic sequence of the PCV3 and/or ORF1, ORF2, and ORF2 of PCV3.

The disclosure is additionally aimed at an immunogenic and/or vaccine composition, characterized in that it comprises at least one of the following compounds: 1) a nucleotide sequence SEQ ID No. 1, SEQ ID No. 3, SEQ ID No. 5, SEQ ID No. 7 or one of their fragments or homologues; 2) a polypeptide of sequence SEQ ID No. 2, SEQ ID No. 4, SEQ ID No. 6, SEQ ID No. 8 or one of their fragments, or a modification thereof; 3) a vector or a viral particle comprising a nucleotide sequence SEQ ID No. 1, SEQ ID No. 3, SEQ ID No. 5, SEQ ID No. 7, or one of their fragments or homologues; 4) a transformed cell capable of expressing a polypeptide of sequence SEQ ID No. 2, SEQ ID No. 4, SEQ ID No. 6, SEQ ID No. 8, or one of their fragments, or a modification thereof; or 5) a mixture of at least two of said compounds.

The disclosure also comprises an immunogenic and/or vaccine composition according to the disclosure, characterized in that it comprises said mixture of at least two of said compounds as a combination product for simultaneous, separate or protracted use for the prevention or the treatment of infection by a PCV3.

In a preferred embodiment, the vaccine composition according to the disclosure comprises the mixture of the following compounds: 1) a pcDNA3 plasmid containing a nucleic acid of sequence SEQ ID No. 1; 2) a pcDNA3 plasmid containing a nucleic acid of sequence SEQ ID No. 3, SEQ ID No. 5, or SEQ ID No. 7; 3) a pcDNA3 plasmid containing a nucleic acid coding for the GM-CSF protein; 4) a recombinant baculovirus containing a nucleic acid of sequence SEQ ID No. 1; 5) a recombinant baculovirus containing a nucleic acid of sequence SEQ ID No. 3, SEQ ID No. 5, or SEQ ID No. 7; and 6) if need be, an adjuvant of the appropriate immunity, especially the adjuvant AIF™.

The disclosure is likewise directed at a pharmaceutical composition according to the disclosure, for the prevention or the treatment of an infection by a PCV3.

It is understood that "prevention" as used in the present disclosure, includes the complete prevention of infection by a PCV3, but also encompasses a reduction in the severity of or incidence of clinical signs associated with or caused by PCV3 infection. Such prevention is also referred to herein as a protective effect.

The disclosure likewise concerns the use of a composition according to the disclosure, for the preparation of a medicament intended for the prevention or the treatment of infection by a PCV3.

Under another aspect, the disclosure relates to a vector, a viral particle or a cell according to the disclosure, for the treatment and/or the prevention of a disease by gene therapy.

Finally, the disclosure comprises the use of a vector, of a viral particle or of a cell according to the disclosure for the preparation of a medicament intended for the treatment and/or the prevention of a disease by gene therapy.

The polypeptides of the disclosure entering into the immunogenic or vaccine compositions according to the disclosure can be selected by techniques known to the person skilled in the art such as, for example, depending on the capacity of said polypeptides to stimulate the T cells, which is translated, for example, by their proliferation or the secretion of interleukins, and which leads to the production of antibodies directed against said polypeptides.

In pigs, as in mice, in which a weight dose of the vaccine composition comparable to the dose used in man is administered, the antibody reaction is tested by taking of the serum followed by a study of the formation of a complex between the antibodies present in the serum and the antigen of the vaccine composition, according to the usual techniques.

The pharmaceutical compositions according to the disclosure will contain an effective quantity of the compounds of the disclosure, that is to say in sufficient quantity of said compound(s) allowing the desired effect to be obtained, such as, for example, the modulation of the cellular replication of PCV3. The person skilled in the art will know how to determine this quantity, as a function, for example, of the age and of the weight of the individual to be treated, of the state of advancement of the pathology, of the possible secondary effects and by means of a test of evaluation of the effects obtained on a population range, these tests being known in these fields of application.

According to the disclosure, said vaccine combinations will preferably be combined with a pharmaceutically or veterinary acceptable carrier and, if need be, with one or more adjuvants of the appropriate immunity.

Today, various types of vaccines are available for protecting animals or man against infectious diseases: attenuated living microorganisms (*M. bovis*—BCG for tuberculosis), inactivated microorganisms (influenza virus), a cellular extracts (*Bordetella pertussis* for whooping cough), recombined proteins (surface antigen of the hepatitis B virus), polysaccharides (pneumococcal). Vaccines prepared from synthetic peptides or genetically modified microorganisms expressing heterologous antigens are in the course of experimentation. More recently still, recombined plasmid DNAs carrying genes coding for protective antigens have been proposed as an alternative vaccine strategy. This type of vaccination is carried out with a particular plasmid originating from a plasmid of *E. coli* which does not replicate in vivo and which codes uniquely for the vaccinating protein. Animals have been immunized by simply injecting the naked plasmid DNA into the muscle. This technique leads to the expression of the vaccine protein in situ and to an immune response of cellular type (CTL) and of humoral type (antibody). This double induction of the immune response is one of the principal advantages of the vaccination technique with naked DNA.

The constitutive nucleotide sequence of the vaccine composition according to the disclosure can be injected into the host after having been coupled to compounds which favor the penetration of this polynucleotide into the interior of the cell or its transport to the cell nucleus. The resultant conjugates can be encapsulated in polymeric microparticles, as described in the international application No. WO 94/27238 (Medisorb Technologies International).

According to another embodiment of the vaccine composition according to the disclosure, the nucleotide sequence, preferably a DNA, is complexed with DEAE-dextran (Pagano et al., 1967) or with nuclear proteins (Kaneda et al., 1989), with lipids (Felgner et al., 1987) or encapsulated in liposomes (Fraley et al., 1980) or else introduced in the form of a gel facilitating its transfection into the cells (Midoux et al., 1993, Pastore et al., 1994). The polynucleotide or the vector according to the disclosure can also be in suspension in a buffer solution or be combined with liposomes.

Advantageously, such a vaccine will be prepared according to the technique described by Tacson et al. or Huygen et al. in 1996 or alternatively according to the technique described by Davis et al. in the international application No. WO 95/11307.

Such a vaccine can likewise be prepared in the form of a composition containing a vector according to the disclosure, placed under the control of regulation elements allowing its expression in man or animal. It will be possible, for example, to use, by way of in vivo expression vector of the polypeptide antigen of interest, the plasmid pcDNA3 or the plasmid pcDNA1/neo, both marketed by Invitrogen (R&D Systems, Abingdon, United Kingdom). It is also possible to use the plasmid V1Jns.tPA, described by Shiver et al. in 1995. Such a vaccine will advantageously comprise, apart from the recombinant vector, a saline solution, for example a sodium chloride solution.

As far as the vaccine formulations are concerned, these can comprise adjuvants of the appropriate immunity which are known to the person skilled in the art, such as, for example, those described above.

These compounds can be administered by the systemic route, in particular by the intravenous route, by the intramuscular, intradermal or subcutaneous route, or by the oral route. In a more preferred manner, the vaccine composition comprising polypeptides according to the disclosure will be administered by the intramuscular route, through the food or by nebulization several times, staggered over time.

Their administration modes, dosages and optimum pharmaceutical forms can be determined according to the criteria generally taken into account in the establishment of a treatment adapted to an animal such as, for example, the age or the weight, the seriousness of its general condition, the tolerance to the treatment and the secondary effects noted. Preferably, the vaccine of the present disclosure is administered in an amount that is protective or provides a protective effect against PCV3 infection.

For example, in the case of a vaccine according to the present disclosure comprising a polypeptide encoded by a nucleotide sequence of the genome of PCV3, or a homologue or fragment thereof, the polypeptide will be administered one time or several times, spread out over time, directly or by means of a transformed cell capable of expressing the polypeptide, in an amount of about 0.1 to 10 µg per kilogram weight of the animal, preferably about 0.2 to about 5 µg/kg, more preferably about 0.5 to about 2 µg/kg for a dose.

The present disclosure likewise relates to the use of nucleotide sequences of PCV3 according to the disclosure for the construction of autoreplicative retroviral vectors and the therapeutic applications of these, especially in the field of gene therapy in vivo.

The feasibility of gene therapy applied to man no longer needs to be demonstrated and this relates to numerous therapeutic applications like genetic diseases, infectious diseases and cancers. Numerous documents of the prior art describe the means of employing gene therapy, especially through viral vectors. Generally speaking, the vectors are obtained by deletion of at least some of the viral genes which are replaced by the genes of therapeutic interest. Such vectors can be propagated in a complementation line which supplies in trans the deleted viral functions in order to generate a defective viral vector particle for replication but capable of infecting a host cell. To date, the retroviral vectors are amongst the most widely used and their mode of infection is widely described in the literature accessible to the person skilled in the art.

The principle of gene therapy is to deliver a functional gene, called a gene of interest, of which the RNA or the corresponding protein will produce the desired biochemical effect in the targeted cells or tissues. On the one hand, the insertion of genes allows the prolonged expression of complex and unstable molecules such as RNAs or proteins which can be extremely difficult or even impossible to obtain or to administer directly. On the other hand, the controlled insertion of the desired gene into the interior of targeted specific cells allows the expression product to be regulated in defined tissues. For this, it is necessary to be able to insert the desired therapeutic gene into the interior of chosen cells and thus to have available a method of insertion capable of specifically targeting the cells or the tissues chosen. Some preferred genes of interest for the present disclosure are those that encode ORF1, ORF2, or ORF3.

Among the methods of insertion of genes, such as, for example, microinjection, especially the injection of naked plasmid DNA, electroporation, homologous recombination, the use of viral particles, such as retroviruses, is widespread. However, applied in vivo, the gene transfer systems of recombinant retroviral type at the same time have a weak infectious power (insufficient concentration of viral particles) and a lack of specificity with regard to chosen target cells.

The production of cell-specific viral vectors, having a tissue-specific tropism, and whose gene of interest can be translated adequately by the target cells, is realizable, for example, by fusing a specific ligand of the target host cells to the N-terminal part of a surface protein of the envelope of PCV3. It is possible to mention, for example, the construction of retroviral particles having the CD4 molecule on the surface of the envelope so as to target the human cells infected by the HIV virus, viral particles having a peptide hormone fused to an envelope protein to specifically infect the cells expressing the corresponding receptor or else alternatively viral particles having a fused polypeptide capable of immobilizing on the receptor of the epidermal growth factor (EGF). In another approach, single-chain fragments of antibodies directed against surface antigens of the target cells are inserted by fusion with the N-terminal part of the envelope protein.

For the purposes of the present disclosure, a gene of interest in use in the disclosure can be obtained from a eukaryotic or prokaryotic organism or from a virus by any conventional technique. It is, preferably, capable of producing an expression product having a therapeutic effect and it can be a product homologous to the cell host or, alternatively, heterologous. In the scope of the present disclosure, a gene of interest can code for an (1) intracellular or (2) membrane product present on the surface of the host cell or (3) secreted outside the host cell. It can therefore comprise appropriate additional elements such as, for example, a sequence coding for a secretion signal. These signals are known to the person skilled in the art.

In accordance with the aims pursued by the present disclosure, a gene of interest can code for a protein corresponding to all or part of a native protein as found in nature. It can likewise be a chimeric protein, for example arising from the fusion of polypeptides of various origins or from a mutant having improved and/or modified biological properties. Such a mutant can be obtained, by conventional biological techniques, by substitution, deletion and/or addition of one or more amino acid residues.

The disclosure thus relates to the vectors characterized in that they comprise a nucleotide sequence of PCV3 according to the disclosure, and in that they additionally comprise a gene of interest.

The present disclosure likewise relates to viral particles generated from said vector according to the disclosure. It additionally relates to methods for the preparation of viral particles according to the disclosure, characterized in that they employ a vector according to the disclosure, including viral pseudoparticles (VLP, virus-like particles).

The disclosure likewise relates to animal cells transfected by a vector according to the disclosure. Likewise comprised in the disclosure are animal cells, especially mammalian, infected by a viral particle according to the disclosure.

One preferred vaccine employs the live chimeric virus DNA clone, in particular, the clone containing the immunogenic genes of PCV3 cloned in the backbone of the nonpathogenic PCV1. Advantageously, the live chimeric virus, which is naturally avirulent when constructed through genetic engineering, does not require time-consuming attenuation procedures. The virus uniquely serves as a live but nonpathogenic replicating virus that produces immunogenic proteins against PCV3 during virus replication, which can then elicit a full range of immune responses against the pathogenic PCV3.

As a further benefit, the live chimeric virus of the present disclosure provides a genetically stable vaccine that is easier to make, store and deliver than other types of attenuated vaccines. Avirulent or attenuated vaccines based upon chimeric viruses are generally considered as safe as, if not safer than, the traditionally modified live vaccines. For example, the ChimeriVax-JE vaccine against Japanese encephalitis virus (JEV), which is a genetically engineered derivative of the yellow fever virus vaccine YFV17D in which the genes encoding the structural proteins prM and E of YFV17D are replaced with the corresponding genes of the attenuated JEV SA14-14-2 strain, has been shown to be genetically stable after prolonged passages both in vitro and in vivo. Another chimeric virus vaccine ChimeriVax-D2 against Dengue virus type 2, which is an attenuated chimeric yellow fever (YF)-dengue type 2 (dengue-2) virus, has also been found to be genetically stable; its sequences were reported to be unchanged after 18 passages in Vero cells.

Another preferred vaccine of the present disclosure utilizes suitable plasmids for delivering the nonpathogenic chimeric DNA clone to pigs. In contrast to the traditional vaccine that uses live or killed cell culture propagated whole virus, this disclosure provides for the direct inoculation of pigs with the plasmid DNA containing the infectious chimeric viral genome.

Additional genetically engineered vaccines, which are desirable in the present disclosure, are produced by techniques known in the art. Such techniques involve, but are not limited to, further manipulation of recombinant DNA, modification of or substitutions to the amino acid sequences of the recombinant proteins and the like. Genetically engineered vaccines based on recombinant DNA technology are made, for instance, by identifying alternative portions of the viral gene encoding proteins responsible for inducing a stronger immune or protective response in pigs (e.g., proteins derived from ORF1, ORF2, ORF3). Such identified genes or immuno-dominant fragments can be cloned into standard protein expression vectors, such as the baculovirus vector, and used to infect appropriate host cells. The host cells are cultured, thus expressing the desired vaccine proteins, which can be purified to the desired extent and formulated into a suitable vaccine product.

If the clones retain any undesirable natural abilities of causing disease, it is also possible to pinpoint the nucleotide sequences in the viral genome responsible for any residual virulence, and genetically engineer the virus avirulent through, for example, site-directed mutagenesis. Site-directed mutagenesis is able to add, delete or change one or more nucleotides. An oligonucleotide is synthesized containing the desired mutation and annealed to a portion of single stranded viral DNA. The hybrid molecule, which results from that procedure, is employed to transform bacteria. Then double-stranded DNA, which is isolated containing the appropriate mutation, is used to produce full-length DNA by ligation to a restriction fragment of the latter that is subsequently transfected into a suitable cell culture. Ligation of the genome into the suitable vector for transfer may be accomplished through any standard technique known to those of ordinary skill in the art. Transfection of the vector into host cells for the production of viral progeny may be done using any of the conventional methods such as calcium-phosphate or DEAE-dextran mediated transfection, electroporation, protoplast fusion and other well-known techniques. The cloned virus then exhibits the desired mutation. Alternatively, two oligonucleotides can be synthesized which contain the appropriate mutation. These may be annealed to form double-stranded DNA that can be inserted in the viral DNA to produce full-length DNA.

Genetically engineered proteins, useful in vaccines, for instance, may be expressed in insect cells, yeast cells or mammalian cells. The genetically engineered proteins, which may be purified or isolated by conventional methods, can be directly inoculated into pigs to confer protection against viral infection or postweaning multisystemic wasting syndrome (PMWS) caused by PCV3. An insect cell line (like HI-FIVE) can be transformed with a transfer vector containing nucleic acid molecules obtained from the virus or copied from the viral genome which encodes one or more of the immuno-dominant proteins of the virus. The transfer vector includes, for example, linearized baculovirus DNA and a plasmid containing the desired polynucleotides. The host cell line may be co-transfected with the linearized baculovirus DNA and a plasmid in order to make a recombinant baculovirus.

Alternatively, DNA from a pig suffering from pneumonia, reproductive failure, PDNS, and/or PMWS, which encode one or more capsid proteins, the infectious PCV3 molecular DNA clone, or the cloned PCV chimeric DNA genome, can be inserted into live vectors, such as a poxvirus or an adenovirus and used as a vaccine.

An immunologically effective amount of the vaccines or immunogenic compositions of the present disclosure is administered to a pig in need of protection against viral infection, pneumonia, reproductive failure, PDNS and/or PMWS. The immunologically effective amount or the immunogenic amount that inoculates the pig can be easily determined or readily titrated by routine testing. An effective amount is one in which a sufficient immunological response to the vaccine is attained to protect the pig exposed to the virus which causes PMWS. Preferably, the pig is protected to an extent in which one to all of the adverse physiological symptoms or effects of the viral disease are significantly reduced, ameliorated or totally prevented.

The vaccine can be administered in a single dose or in repeated doses with single doses being preferred. Single dose vaccines provide protection after a single dose without the need for any booster or subsequent dosages. Protection can include the complete prevention of clinical signs of infection, or a lessening of the severity, duration, or likelihood of the manifestation of one or more clinical signs of infection. Dosages may range, for example, from about 1 microgram to about 1,000 micrograms of the plasmid DNA containing the infectious chimeric DNA genome (dependent upon the concentration of the immuno-active component of the vaccine), preferably 100 to 200 micrograms of the chimeric PCV1-3 DNA clone, but should not contain an amount of virus-based antigen sufficient to result in an adverse reaction or physiological symptoms of viral infection. Methods are known in the art for determining or titrating suitable dosages of active antigenic agent to find minimal effective dosages based on the weight of the pig, concentration of the antigen and other typical factors. Preferably, the infectious chimeric viral DNA clone is used as a vaccine, or a live infectious chimeric virus can be generated in vitro and then the live chimeric virus is used as a vaccine. In that case, from about 50 to about 10,000 of the 50% tissue culture infective dose ($TCID_{50}$) of live chimeric virus, for example, can be given to a pig.

Desirably, the vaccine is administered to a pig not yet exposed to the PCV virus. The vaccine containing the chimeric PCV1-3 infectious DNA clone or other antigenic forms thereof can conveniently be administered intranasally, transdermally (i.e., applied on or at the skin surface for systemic absorption), parenterally, etc. The parenteral route of administration includes, but is not limited to, intramuscular, intravenous, intraperitoneal, intradermal (i.e., injected or otherwise placed under the skin) routes and the like. Since the intramuscular and intradermal routes of inoculation have been successful in other studies using viral infectious DNA clones, these routes are most preferred, in addition to the practical intranasal route of administration. Although less convenient, it is also contemplated that the vaccine is given to the pig through the intralymphoid route of inoculation. One unique, preferred method of administration involves directly injecting the plasmid DNA containing PCV1-3 chimera into the pig intramuscularly, intradermally, intralymphoidly, etc.

When administered as a liquid, the present vaccine may be prepared in the form of an aqueous solution, syrup, an elixir, a tincture and the like. Such formulations are known in the art and are typically prepared by dissolution of the antigen and other typical additives in the appropriate carrier or solvent systems. Suitable carriers or solvents include, but are not limited to, water, saline, ethanol, ethylene glycol, glycerol, etc. Typical additives are, for example, certified dyes, flavors, sweeteners and antimicrobial preservatives such as thimerosal (sodium ethylmercurithiosalicylate). Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions that contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of porcine body fluids. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives that can be employed in the present vaccine include, but are not limited to, dextrose, conventional antioxidants and conventional chelating agents such as ethylenediamine tetraacetic acid (EDTA). Parenteral dosage forms must also be sterilized prior to use.

In another embodiment of the present disclosure, a protein encoded by a chimeric DNA molecule is provided. This protein can be administered separately, or in addition to the other compositions described herein. In preferred forms, the protein is administered in an amount ranging from about 0.2 to about 400 µg/ml. The chimeric DNA molecule is preferably as described herein.

An infectious DNA clone of PCV3 is constructed, as described herein, so that a biologically pure and homogeneous infectious virus stock can be generated for pathogenesis studies and the development of nonpathogenic, chimeric vaccines. The course of clinical disease, virus distribution and pathological lesions associated with PCV3 infection are more definitively characterized by using this molecular DNA clone and a biologically pure and homogeneous infectious PCV3 virus stock derived from the molecular DNA clone than have been observed in the past, which lends itself to the development of the desired vaccine products of the present disclosure.

The PCV3 molecular clone is generated by ligating two copies of the complete PCV3 genome in tandem into the pSK vector. In sharp contrast to the single copy genome disclosed in the art, the infectious DNA PCV3 clone made by the methods described herein contains two complete copies of the PCV3 genome ligated together in tandem repeat. Ligating two copies of genome in tandem provides a similar circular genome that mimics the usual circular genome of PCV3. The advantage of having two copies of the genome in tandem in the infectious DNA PCV3 clone is to be able to maximize replication when the infectious DNA clone is transfected in vitro and in vivo. Thus, the clone of the disclosure operates more efficiently and effectively than the prior single copy genome.

Infection of animals with the molecular viral clone is extremely useful to studying the genetic determinants of viral replication and virulence in the host. PCV3 has been incriminated as the causative agent of pneumonia, reproductive failure, PMWS, and PDNS. PMWS and PDNS are complex disease syndromes in swine and multiple factors may be involved in the clinical presentation of PMWS and/or PDNS. However, the difficulty in producing a biologically pure form of PCV3 due to the presence of other common swine agents in the tissue homogenates of diseased pigs has impeded a definitive characterization of the clinical disease and pathological lesions solely attributable to PCV3 infection. This will be the first time an infectious molecular DNA clone of PCV3 will be constructed and used to characterize the disease and pathological lesions associated with PCV3 infection by direct in vivo transfection of pigs with the molecular clone.

The homogeneous PCV3 live virus stock derived from the molecular clone will be shown to be infectious in vitro when transfected into PK-15 cells. The cloned PCV3 genomic DNA will also be infectious when directly injected into the livers and superficial iliac lymph nodes of specific-pathogen-free (SPF) pigs. Animals injected with the cloned PCV3 plasmid DNA will develop an infection and disease resembling that induced by intranasal inoculation with a homogenous, infectious PCV3 live virus stock. Seroconversion to PCV3-specific antibody will be detectable in the majority of pigs from the inoculated groups at 35 days postinoculation (DPI).

The onset and duration of viremia in pigs inoculated with the chimeric PCV1-3 DNA clone will be similar to those of the pigs inoculated with the nonpathogenic PCV1 DNA clone, whereas viremia in pigs inoculated with the PCV3 clone will appear earlier and last longer. Beginning at 14 DPI and lasting about 2-6 weeks, viremia will be detectable in the majority of the PCV3-inoculated animals. Similarly, the majority of inoculated pigs necropsied at 35 DPI will have seroconverted to PCV3-antibodies. PCV3 antigen will be detected in various tissues and organs in inoculated pigs. Gross lesions will be limited to the lungs and lymph nodes, and will be characterized by systematically enlarged tan colored lymph nodes, lungs that failed to collapse and mild multifocal tan-colored foci of consolidation. Gross lesions affecting the lymph nodes in both the nonpathogenic PCV1 and the chimeric PCV1-3 inoculated pigs will be mild and limited to only a few animals, whereas the pathogenic PCV3 inoculated pigs will have a greater incidence of moderate-to-severe swelling and discoloration of lymphoid tissues. Statistical analysis will reveal that the scores of the gross lesions in the lymph nodes of the chimeric PCV1-3 inoculated animals will be similar to those in nonpathogenic PCV1 inoculated pigs. At 21 DPI, PCV3 inoculated pigs will have gross lesions that are statistically more severe than those of the PCV1 and the chimeric PCV1-3 inoculated pigs. Histopathological lesions and PCV3-specific antigen will be detected in numerous tissues and organs including brain, lung, heart, kidney, tonsil, lymph nodes, spleen, ileum and liver of the inoculated (infected) pigs. The histopathological lesions in multiple tissues and organs similar to those of PMWS will be reproduced with the PCV3 molecular DNA clone as well as with the infectious virus prepared in vitro from the molecular DNA clone. Microscopically, at both 21 and 49 DPIs, the chimeric PCV1-3 inoculated animals will have statistically less microscopic lesions than the PCV3 inoculated animals. The microscopic lesion scores in lymph nodes of the chimeric PCV1-3 inoculated pigs will be similar to those of the nonpathogenic PCV1, the reciprocal chimeric PCV3-1 and the uninoculated control animals. Moderate to severe microscopic lesions will be found in multiple tissues of pathogenic PCV3 inoculated animals including lung, liver, lymphoid, spleen, brain, heart, kidney and tonsil tissue. However, in chimeric PCV1-3 inoculated animals, mild to moderate microscopic lesions will be limited only to liver, lymph nodes and kidney tissues.

The availability of the infectious DNA clone of PCV3 described herein makes it feasible to develop the genetically engineered attenuated vaccine for preventing PCV3 infection and PDNS and PMWS in pigs.

The structural and functional relationships of the PCV genes are better understood due to the availability of the PCV3, PCV1, chimeric PCV1-3, and reciprocal chimeric PCV3-1 infectious DNA clones described herein.

The construction of an infectious PCV3 molecular DNA clone, and the demonstration of infection by direct injection of cloned PCV3 plasmid DNA into the liver and lymph nodes of pigs in the context of the present disclosure will be advantageous for PCV3 studies. This in vivo transfection system will enhance the study of the structural and functional relationship of PCV3 genes using recombinant plasmids constructed in vitro to test different regions or genes of PCV3 for their roles in virus replication and pathogenesis in the host. The replication and pathogenesis of PCV3 can be studied in vivo without having to produce infectious virus stocks by propagating PCV3 in cell cultures. This is advantageous as serial cell culture passages may select for viral variants. Another advantage of using cloned PCV3 genomic DNA, instead of live virus, for animal studies is its relative ease for quantitation of the inoculation dose. The amount of the cloned PCV3 DNA used for animal inoculation can be easily determined by a spectrophotometer, whereas the dose of live PCV3 virus requires infectivity titration in cell cultures and confirmation of infection by IFA. Direct injection of animals with cloned PCV3 plasmid DNA eliminates the problems associated with the presence of other indigenous swine agents in tissue homogenate inocula in animal studies.

In one aspect of the present disclosure, the immunogenic ORF2 capsid gene is switched between the pathogenic PCV3 and the nonpathogenic PCV1 to produce the unique structure of the chimeric PCV1-3 infectious DNA clone. Surprisingly and advantageously, the chimeric PCV1-3 infectious clone will replicate, express the immunogenic ORF2 capsid antigen in vitro and in vivo, and induce a specific antibody response against PCV3 ORF2 but retain the nonpathogenic nature of PCV1. The chimeric PCV1-3 infectious DNA clone will have the ability to induce a strong immune response against PCV3 while inducing only a limited infection with mild pathologic lesions similar to that of the nonpathogenic PCV1. For vaccine development, the relatively easy storage and stability of cloned DNA, and the economy of large-scale recombinant PCV3 plasmid DNA and chimeric PCV1-3 DNA clone production will provide an attractive means of delivering a live, infectious viral DNA vaccine or genetically engineered attenuated viral vaccines to pigs. Therefore, the chimeric PCV1-3 infectious DNA clone taught in this disclosure is a useful vaccine candidate against PCV3 infection and PMWS.

It should be appreciated that all scientific and technological terms used herein have the same meaning as commonly understood by those of ordinary skill in the art. For purposes of this disclosure, the term "infectious" means that the virus replicates in pigs, regardless of whether or not the virus causes any diseases. "SPF" refers to Specific-pathogen-free pigs.

The "gnotobiotic" pigs intend germ-free pigs. The terms "PCV3 plasmid DNA," "PCV3 genomic DNA" and "PCV3 molecular DNA" are being used interchangeably to refer to the same cloned nucleotide sequence.

The following examples demonstrate certain aspects of the present disclosure. However, it is to be understood that these examples are for illustration only and do not purport to be wholly definitive as to conditions and scope of this disclosure. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified. Further unless noted otherwise, all components of the disclosure are understood to be disclosed to cover "comprising", "consisting essentially of", and "consisting of" claim language as those terms are commonly used in patent claims.

Another aspect of the present disclosure is the preparation of the combination vaccine(s) or immunogenic compositions. Such combinations can be between the different vaccine components described herein. For example, a vaccine of the present disclosure can include both protein portions and DNA portions of PCV3, as described herein, which are administered concurrently or separately. Additionally, the combinations can be between the PCV3 vaccine components described herein and antigens of other disease-causing organisms, such as those described above.

According to a further aspect, the vaccine or immunogenic composition is first dehydrated. If the composition is first lyophilized or dehydrated by other methods, then, prior to vaccination, said composition is rehydrated in aqueous (e.g. saline, PBS (phosphate buffered saline)) or non-aqueous solutions (e.g. oil emulsion (mineral oil, or vegetable/metabolizable oil based/single or double emulsion based), aluminum-based, carbomer based adjuvant).

According to the present disclosure, an effective amount of a combination vaccine administered to pigs provides effective immunity or a protective effect against microbiological infections caused by PCV3 and at least one further pathogen. Preferred combinations of antigens for the treatment and prophylaxis of microbiological diseases in pigs are listed above.

According to a further embodiment, the combination vaccine is administered to pigs in one or two doses at an interval of about 2 to 4 weeks. For example, the first administration is performed when the animal is about 2 to 3 weeks to about 8 weeks of age. The second administration is performed about 1 to about 4 weeks after the first administration of the first vaccination. According to a further embodiment, revaccination is performed in an interval of 3 to 12 month after administration of the second dose. Administration of subsequent vaccine doses is preferably done on a 6 month to an annual basis. In another preferred embodiment, animals vaccinated before the age of about 2 to 3 weeks should be revaccinated. Administration of subsequent vaccine doses is preferably done on an annual basis. In the event that one of the components of the combination vaccine is effective after just a single dose, such component needs to only be administered a single time with the other component (s) administered according to their preferred regimen.

The amount of combination vaccine that is effective depends on the ingredients of the vaccine and the schedule of administration. Typically, when an inactivated virus or a modified live virus preparation is used in the combination vaccine, an amount of the vaccine containing about $10^2$ to about $10^9$ TCID$_{50}$ per dose, preferably about $10^3$ to $10^8$ TCID$_{50}$ per dose, more preferably, about $10^4$ to about $10^8$ TCID$_{50}$ per dose. In general, inactivated antigen is normally used in higher amounts than live modified viruses. Typically, when bacterial antigen is used in the combination vaccine, the vaccine containing an amount of about $10^3$ to about $10^9$ colony forming units (CFU) per dose, preferably, about $10^4$ to about $10^8$ (CFU) per dose, more preferably about $10^5$ to about $10^6$ (CFU) per dose. Sub-unit vaccines are normally administered with an antigen inclusion level of at least 0.2 µg antigen per dose, preferably with about 0.2 to about 400 µg/dose, still more preferably with about 0.3 to about 200 µg/dose, even more preferably with about 0.35 to about 100 µg/dose, still more preferably with about 0.4 to about 50 µg/dose, still more preferably with about 0.45 to about 30 µg/dose, still more preferably with about 0.6 to about 15 µg/dose, even more preferably with about 0.75 to about 8 µg/dose, even more preferably with about 1.0 to about 6 µg/dose, and still more preferably with about 1.3 to about 3.0 µg/dose. For example, the antigen inclusion level of the PCV3 ORF2 antigen, preferably of the PCV3 ORF2 protein as provided herewith, contains about 2 µg to about 150 µg, preferably about 2 µg to about 60 µg, even more preferably about 2 µg to about 50 µg, even more preferably about 2 µg to about 40 µg, even more preferably about 2 µg to about 30 µg, even more preferably about 2 µg to about 25 µg, even more preferably about 2 µg to about 20 µg, even more preferably about 4 µg to about 20 µg, and even more preferably about 4 µg to about 16 µg.

The composition according to the disclosure may be applied intradermally, intratracheally, or intravaginally. The composition preferably may be applied intramuscularly or intranasally. In an animal body, it can prove advantageous to apply the pharmaceutical compositions as described above via an intravenous injection or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the compositions according to the disclosure may be administered once or several times, also intermittently, for instance on a daily basis for several days, weeks or months, and in different dosages.

Example 1

This example develops qPCR for specific detection of the PCV3 capsid gene.

Viral DNA was isolated from clinical specimens using the MagMax-96 total nucleic acid isolation kit according to the manufacturer's protocol. Nucleic acid from formalin-fixed, paraffin-embedded tissues was extracted with the QIAamp DNA FFPE Tissue kit as instructed by the manufacturer (Qiagen, Valencia, Calif.). A 5'-nuclease assay was designed to target a 112 bp region of the PCV3 cap gene nucleic acid in samples: probe, 5'-FAM-ACC CCA TGG-Zen-CTC AAC ACA TAT GAC C-Iowa Black-3' (SEQ ID NO. 14); Forward, 5'-AGT GCT CCC CAT TGA ACG-3' (SEQ ID NO. 13); Reverse, 5'-ACA CAG CCG TTA CTT CAC-3' (SEQ ID NO. 12). Quantitative PCR was performed with the Qiagen Quantitect PCR kit under the following conditions: 95° C., 15 minutes; and 45 cycles of 94° C., 15 seconds and 60° C. for 60 seconds. The sensitivity and specificity of the assay was determined using a dilution series of a plasmid (pSF-CMV-cap) containing the entire PCV3 cap gene cloned into pSF-CMV-AMP (Oxford Genetics, UK) and PCV2 nucleic acid extracted from cell culture. The cycle threshold ($C_t$) values determined from the plasmid dilution series were used to create a standard curve for the calculations to determine genomic copies/ml (gc/ml).

The complete genome for PCV3 was determined from a fetal tissue homogenate pool from the PDNS-outbreak farm and from a sample in the prevalence study using Sanger sequencing of four overlapping amplicons generated with primers shown in Table 1. The PCR was performed using TaKaRa Taq™ as follows: 94° C., 4 minutes; followed by 40 cycles of 94° C., 20 seconds; 50° C., 30 seconds; 72° C., 1 minute; and 72° C. for 5 minutes. Sequencing to confirm select PCV3 positive samples was performed using a 330 bp internal cap gene primer set: 5'-CCA CAG AAG GCG CTA TGT C-3' (SEQ ID NO. 16) and 5'-CCG CAT AAG GGT CGT CTT G-3' (SEQ ID NO. 17). The cap gene PCR reactions were performed using TaKaRa Taq™ as outlined above. PCR products were Sanger sequenced for verification.

Example 2

This example isolated the virus.

Virus isolation was attempted on swine testicles cells (ST) and porcine kidney cells (PK-15) maintained in minimal essential media (MEM) supplemented with L-glutamine and 5% fetal bovine sera. Cells were seeded onto 6-well plates (60-80% confluent) and 100 µl of sample were inoculated into 1 ml viral replacement media, which consisted of MEM and penicillin-streptomycin solution. Cells were observed daily for cytopathic effects and PCV3 growth was monitored by qPCR and immunofluorescence.

Example 3

This example demonstrates the cloning, expression and purification of PCV3 capsid protein.

To create the recombinant PCV3 cap construct, primers were designed to amplify a portion of the PCV3 gene encoding amino acids (aa) 35-214: F, 5'-AAA AAA <u>GCTAGC</u> GCT GGA ACA TAC TAC ACA-3' (SEQ ID NO. 18); R, 5'-AAA AAA <u>GAATTC</u> TTA GAG AAC GGA CTTGTA ACG-3' (SEQ ID NO. 19). The 5' ends of the forward and reverse primers contained NheI and EcoRI restriction sites (underlined), respectively. PCR products were cloned into the pET28a (Novagen, Madison, Wis.) vector to enable expression of the N-terminal truncated PCV3 cap as an N-terminal 6× histidine (His) fusion protein in E. coli. The pET28a-cap plasmid was transformed into E. coli BL21 (DE3) cells and expressed as previously described. After expression, bacteria were harvested by centrifugation and lysed using the B-PER reagent (Pierce, Rockford, Ill.) following the Ni-NTA agarose (Qiagen, Valencia, Calif.) purification was completed as specified by the manufacturer. The purity and identity of the recombinant protein was assessed by sodium dodecyl sulfate-polyacrylamide gel electrophoresis (SDS-PAGE) under denaturing conditions and Western blot detecting the His-tag at the N-terminal of the recombinant protein.

Example 4

This example demonstrates the production and in vitro characterization of an anti-PCV3 capsid monoclonal antibody.

BALB/c mice were immunized with purified, truncated capsid protein (35-214aa). The mice were inoculated with 50 µg of antigen mixed with Freund's incomplete adjuvant bi-weekly for a total of eight weeks. Subsequently, mouse splenocyte cells were fused with NS-1 myeloma cells. Monoclonal antibodies (MAbs) specific to PCV3 were identified by immunofluorescence antibody assays (IFA) using HEK293 cells expressing native PCV3 cap. HEK293 cells on a 6-well plate maintained in MEM with 5% fetal bovine serum (FBS) and antibiotics (ciprofloxacin, penicillin, streptomycin and gentamycin) were transfected with pSF-CMV-AMP or a plasmid derived from pSF-CMV-AMP which contained the complete PCV3 cap gene cloned into the XhoI restriction site (pSF-CMV-cap). On a 6 well plate, $10^6$ cells were transfected with Lipofectamine™ 2000 (Invitrogen), per the manufacturer's instructions, and 10 µg of DNA. After 48 hours, the plates were fixed with 80% acetone for 10 minutes at room temperature (RT) and allowed to dry. Transfected cells were incubated with undiluted anti-PCV3-cap MAbs at 37° C. for 1 hour, followed by three washes with phosphate buffered saline (PBS), and incubated with fluorescein isothiocyanate (FITC)-conjugated goat anti-mouse IgG (Jackson Immunoresearch Laboratories Inc. West Grove, Pa.) diluted 1:100 in PBS at 37° C. for one hour. Following a final wash, cells were visualized using an Eclipse TE2000-U inverted fluorescent microscope (Nikon). ST cells infected with PCV2 were used to evaluate the specificity of the PCV3 MAbs.

Example 5

This example demonstrates PCV3 detection and immunohistochemistry on PDNS cases.

Tissues were fixed in 10% neutral buffered formalin at RT and tissue sections were embedded in paraffin until sectioning. The immunohistochemistry was performed via the standard protocol and slides were visualized with a LSM 700 confocal scanning microscope (Zeiss).

Example 6

This example demonstrates the development of a recombinant PCV3 capsid ELISA.

The ELISA was performed similar to assays previously described using 2 µg/ml of purified recombinant PCV3 capsid protein per well to coat the Corning EIA/RIA High-binding plates (33-35).

Results for Examples 1-6

The full genome sequences of PCV3 used in the phylogenetic analyses were submitted to Genbank under the accession numbers KT869077 (PCV3 strain 29160) and KX458235 (PCV3 strain 2164). Previously published sequences used for phylogenetic analysis include: Barbel circovirus (BarCV) GU799606; Bat circovirus-1 (BtCV-1) JX863737; Bat circovirus-2 (BtCV-2) KC339249; Bat circovirus-3 (BtCV-3) JQ814849; Beak and Feather disease virus (BFDV) AF080560; Canary circovirus (CaCV) AJ301633; Canine circovirus (CanineCV) KC241983; Chimpanzee faeces associated circovirus (ChfaCV) GQ404851; Duck circovirus (DuCV) AY228555; European catfish circovirus (EcatfishCV) JQ011377; Finch Circovirus (FiCV) DQ845075; Goose circovirus (GoCV) AJ304456; Gull circovirus (GuCV) DQ845074; Human faeces associated circovirus (HufaCV) GQ404856; Mink circovirus (MiCV) KJ020099; Columbid circovirus (PiCV) AF252610; Porcine circovirus 1 (PCV1) Y09921; Porcine circovirus 2 (PCV2) AF027217; PorkNW2/USA/2009 HQ738638; Raven circovirus (RaCV) DQ146997; Starling circovirus (StCV) DQ172906; Swan circovirus (SwCV) EU056309; Zebra finch circovirus (ZfiCV) KP793918.

Clinical and histological findings of an outbreak of PDNS-like disease in a commercial sow farm.

During June 2015, a commercial swine operation experienced a 10.2% increase in sow mortality rate and 0.6% decrease in conception rate compared to historical farm averages due to an outbreak of PDNS. Clinically, affected sows were anorexic, and presented multifocal papules, macules and superficial dermatitis. Tissue samples were submitted to the ISUVDL for diagnostic testing. Histologically, skin lesions were characterized by acute necrotic dermatitis and epidermatitis associated with lymphoplasmacytic perivascular cuffs. The kidneys displayed dilated cortical tubules, attenuation and regeneration of the tubular lining epithelium, and large clusters of lymphocytes and macrophages diffusely infiltrated the cortical interstitium and glomeruli. The farm experienced an increment of 1.19 aborted mummified fetuses per litter above the historical average abortion rate. The aborted litters contained mummified fetuses of varied gestational age, consistent with those previously described in PCV2 associated abortion. While the gross and histological lesions observed in sows, as well as the presence of abortions, were consistent with PCVAD, all sow tissues, including kidney, lymph node, lung and skin, tested negative by IHC and qPCR for PCV2, PRRSV and IAV. In addition, fetal tissues were negative for PCV2, PRRSV and PPV by qPCR.

Metagenomic Sequencing

A tissue homogenate pool, prepared from the three fetuses, was analyzed by viral metagenomic sequencing. The Miseq run generated 989,478 total reads with 926,380 mapping to the host genome, *Sus scrofa*. The remaining reads were assembled de novo resulting in 27 contigs. Approximately 54% of the reads mapped to a 1,246 bp contig which was 98% similar to a partial circovirus genome identified in commercial ground pork, PorkNW2/USA/2009 (accession HQ738638), when analyzed by BLASTN. The remaining reads showed no similarity to any known eukaryotic virus.

Metagenomic sequencing was also performed on a pooled tissue homogenate from the sows with PDNS-like lesions. De novo assembly of sequences not mapping to the *Sus scrofa* reference yielded 735 contigs which were analyzed by BLASTN. Two contigs had ~97% identity to torque teno virus 1 (TTV-1). Assembly using a PCV3 reference (KT869077) identified four reads mapping to the genome. The remaining reads showed no homology to known eukaryotic viruses.

Genetic Analysis

Rolling circle amplification followed by PCR and Sanger sequencing of the resulting amplicons allowed assembly of a 2,000 nucleotide (nt) circular genome from the fetal tissue homogenate. ORF analysis identified three ORFs encoding proteins greater than 200 amino acids (aa), with two ORFs showing homology to circovirus rep and cap proteins by BLASTP, orientated in opposite directions (FIG. 1). Within the 235 nt 5'-intergenic region between the rep and cap ORFs on the rep gene strand was a predicted stem-loop structure with a 9 nt stem and loop nonomer identical to PCV1 (TAGTATTAC) (SEQ ID NO. 15). Following convention, the "A" residue at position 8 in the loop nonomer was defined as position "1" in the genome.

The largest ORF encoded a predicted 297 aa protein which by BLASTP was 69.4% identical to a partial replicase protein of Circoviridae PorkNW2/USA/2009 (accession ADU77001, 221 aa) and 54% identical to a bat circovirus from China (accession AIF76248, 293 aa). The PorkNW2/USA/2009 genome was obtained from commercial pork meat products and encodes for a complete replicase and partial capsid gene most similar in organization and sequence to circoviruses. Conserved circovirus replicase and helicase domains were identified by BLASTP from aa 9-93 and 162-251, respectively, in the rep ORF. Further examination of the rep ORF protein sequence revealed conserved rolling circle replication (RCR) motifs and a P-loop motif similar to GoCV and PiCV. Of the three RCR motifs conserved among circoviruses, in PCV3 the FTLNN (SEQ ID NO. 20) motif contained a single mutation, present as FTINN (SEQ ID NO. 21). This mutation is seen in other circoviruses such as GoCV. The two other RCR motifs, HLQG (SEQ ID NO. 22) and YCKK (SEQ ID NO. 23), are present in PCV3 as well. Moreover, three motifs conserved among circovirus replicase proteins but having unknown function were identified in PCV3 including, WWDGY (amino acids 196-200) (SEQ ID NO. 24), DDFYGWVP (amino acids 209-216) (SEQ ID NO. 25), and DRYP (amino acids 225-228) (SEQ ID NO. 26). Interestingly, a canonical start codon was not identified. A GTC (SEQ ID NO. 27) codon (encoding valine) is present at 5'-end of the ORF with the closest in-frame ATG (SEQ ID NO. 28) present approximately 400 bp downstream. This alternative start codon was also seen in PorkNW2/USA/2009. Alternative initiation codons have been proposed for a number of avian circoviruses, including goose circovirus, pigeon circovirus and beak and feather disease virus.

The putative cap ORF, in the opposite orientation of rep, encodes a 214 aa protein 87% identical to the partial capsid sequence (110 aa) of PorkNW2/USA/2009 and 36-37% identical to PCV2 and duck circoviruses (233 and 257 aa, respectively) by BLASTP (FIG. 1). Similar to other circovirus capsid proteins, the N-terminus contained numerous arginine residues and was highly basic. A conserved circovirus capsid domain was identified by BLASTP from aa 26-173. Additionally, the PCV3 cap protein had no predicted N-linked glycosylation sites but two predicted O-linked glycosylation sites at aa 146 and 150 (S and T, respectively). This contrasts to PCV2 which has two experimentally verified N-linked glycosylation sites.

The third ORF, oriented on the same strand as the predicted rep, encodes a 231 aa protein that is 94% identical to an ORF identified in PorkNW2/USA/2009 and 39% identical to Murid herpesvirus M169, a protein of unknown function. Similar to rep, the initiation codon for ORF3 is unclear. The codon at the 5'-end is TCG (encoding serine). A methionine at ORF3 aa 55 is an alternate possible initiation site which would yield a 177 aa protein.

Owing to the genetic and structural similarity to the genus Circovirus and the <70% capsid aa identity to other species, the novel species is proposed as porcine circovirus 3 (PCV3). The PCV3 genome sequences were submitted to Genbank under accession KT869077 and KX458235.

Phylogenetic Analysis

Figure 2:
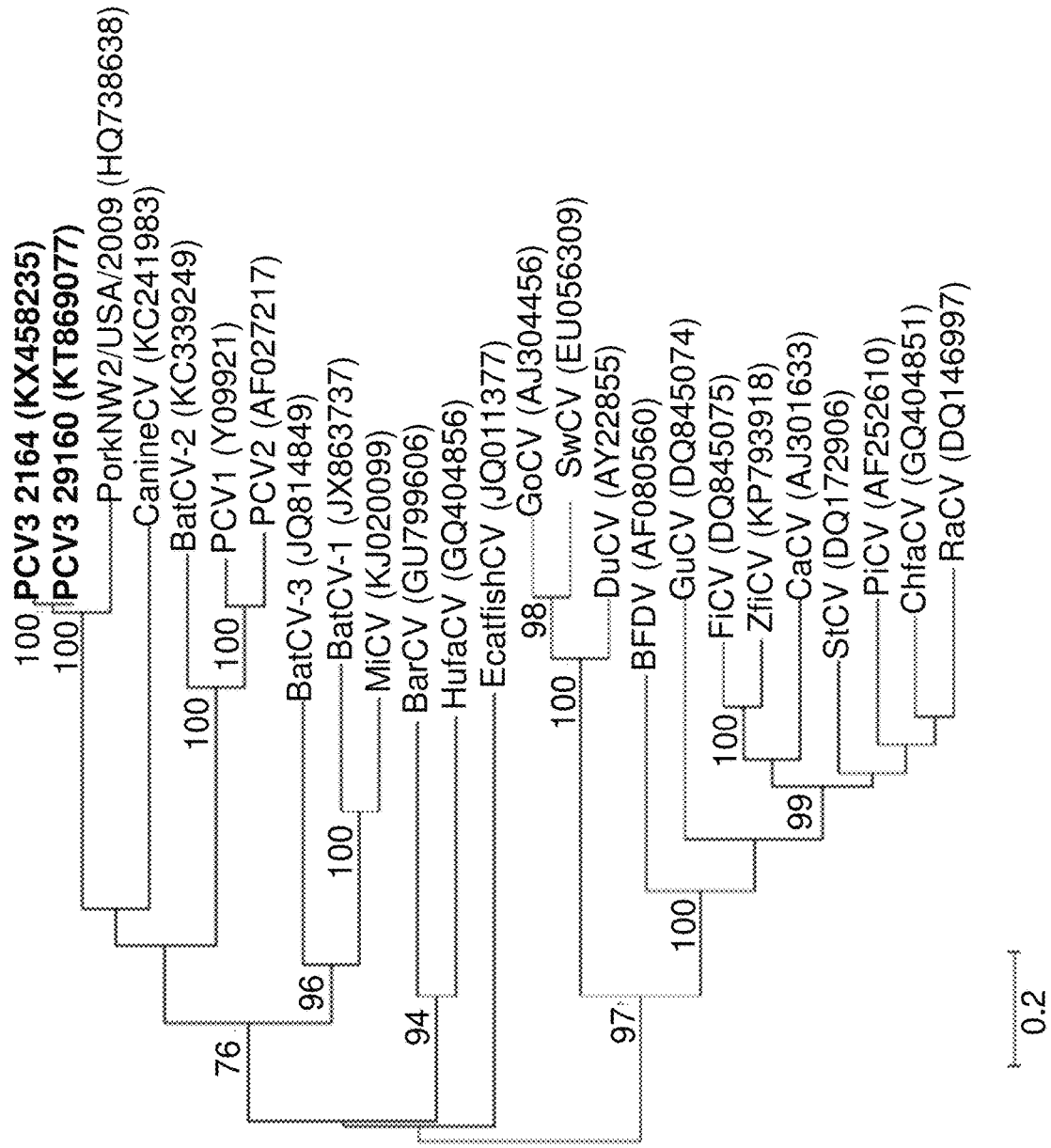
FIG. 2 is a phylogenetic tree of Circovirus replicase proteins

To investigate the evolutionary relationship of PCV3 to other members of Circoviridae, genome sequences from twenty-three members of the family and two PCV3 genomes were analyzed. Analysis of the full circovirus genomes grouped both PCV3 sequences in a Glade with PorkNW2/USA/2009 separate from all other members of the genus (FIG. 2). The phylogeny indicated that PCV3 was most closely related to canine circovirus (KC241983), however this relationship lacked strong bootstrap support. The phylogeny also suggests that PCV3 and canineCV shares a common ancestor with a clade containing PCV1, PCV2 and BatCV-2 (KC339249). With the exception of the human circovirus (HufaCV, GQ404856), mammalian and avian circoviruses belonged to separate, well supported clades.

Detection of PCV3 by PCR

To confirm the presence of PCV3 in porcine samples, a 5'-nuclease assay was designed to determine the presence of the PCV3 cap gene. The fetal tissue homogenate samples from the outbreak farm were strongly positive for PCV3 with $C_t$ values between 16.7 and 21.3, corresponding to high levels of PCV3 of approximately to $1.88 \times 10^8$ and $7.55 \times 10^6$ gc/ml. Tissues from three of the sows with PDNS-like lesions were positive for PCV3, having between $2.13 \times 10^4$ and $8.62 \times 10^4$ gc/ml. In addition, 30 serum samples submitted to ISUVDL were analyzed for PCV3 by qPCR. The serum samples were positive for PCV3 with $5.63 \times 10^2$ to $2.28 \times 10^4$ gc/ml. The serum sample with the highest PCV3 titer was used amplified by PCR to generate overlapping amplicons to obtain a second complete PCV3 genome which was 99.0% identical to the original PCV3 from the farm with the outbreak. This second PCV3 genome was submitted to Genbank under accession KX458235.

Additionally, to investigate the prevalence of PCV3, a total of 271 samples submitted to ISUVDL for respiratory disease diagnostic testing, were analyzed by qPCR. Thirty-four (12.5%) of the samples were positive with titers of $3.00 \times 10^2$-$1.52 \times 10^7$ gc/ml.

Characterization of PCV3-Cap MAb14

HEK293 cells transfected with the pSF-CMV-cap were incubated separately with four different MAb clonal cell supernatants and screened by IFA. Fluorescence localized to the nucleus, as expected owing to the predicted highly basic nuclear localization signal, was observed for clone 14 (MAb14). No fluorescence was observed for cells transfected with pSF-CMV-Amp. In addition, ST cells infected with PCV2 had no detectable fluorescence.

Virus Isolation

Virus isolation was attempted on ST and PK-15 cells. Cells were inoculated with filtered fetal tissue homogenates and passaged three times. No cytopathic effects were evident and Ct values increased with each successive passage. No fluorescence was evident by IFA using MAb14.

Histological Lesions Associated with the Presence of PCV3 Antigen in PDNS Cases

Tissue samples from the sows with PDNS-like lesions and archived PDNS cases were examined by H&E staining and IHC using PCV3 MAb14. Lungs showed variable degrees of bronchointerstitial pneumonia occasionally complicated by a secondary suppurative bronchopneumonia. The small and medium-size airways and small blood vessels were cuffed with peribronchiolar and perivascular aggregates of lymphocytes and plasma cells. Adjacent alveolar septa were infiltrated by lymphocytes and plasma cells. Within alveolar lumina there were abundant intraluminal edema intermixed with moderate numbers of foamy macrophages, rare multinucleated giant cells, and small clusters of neutrophils. Occasional lymphocytes and scatter macrophages showed moderate intracytoplasmic immunostaining against PCV3. In a section of skin, the dermis and subcutis had characteristic necrotizing vasculitis with fibrinoid change and transmural neutrophilic infiltration, hemorrhage, and fibrin exudation. The inflammatory infiltrate often extended into the surrounding dermis and subcutis. There were also scatter lymphoplasmacytic aggregates that occasionally cuff around vessels and dermal adnexa. Occasionally, the epidermis was hyperplastic with mild orthokeratotic hyperkeratosis. The dermal lymphocytic infiltration showed marked intracytoplasmic immunostaining against PCV3. Minimal background staining was evident when PCV3MAb14 was replaced with PBS.

The lymph nodes showed diffuse granulomatous lymphadenitis. The cortical follicles had moderate lymphoid depletion and were infiltrated by histiocytes and numerous multinucleated giant cells. The subcortical and medullary sinuses were expanded by moderate amounts of edema and hemorrhage, intermixed with numerous macrophages and plasma cells. The follicular and perifollicular lymphocytic population showed a diffuse, intense intracytoplasmic staining against PCV3 as compared to background staining where PCV3 MAb14 was replaced with PBS or lymph node tissue from a PCV3 qPCR negative pig.

Sections of kidney were characterized by the presence of diffuse membrane proliferative glomerulonephritis. There was severe glomerulosclerosis and the Bowman's capsules were often thickened, and cortical tubules were attenuated and associated with variable interstitial fibrosis. The glomerular mesangium was hypercellular and thickened by amorphous eosinophilic material. The tubules were occasionally ecstatic, lined by attenuated epithelium and occasionally presented marked proteinosis. Scattered throughout the sections were small to medium size clusters of lymphocytes and plasma cells in the interstitium. The tubular epithelium showed random areas of positive staining against PCV3. Minimal background fluorescence were observed for slides mock stained with PBS and goat anti-mouse FITC or kidney tissue from a PCV3 qPCR negative pig.

Detection of PCV3 Nucleic Acid in Tissues with PDNS Lesions

To further investigate the etiologic role of PCV3 in PDNS, 48 cases with histological lesions consistent with PDNS that previously tested negative for PCV2 by IHC were evaluated. Tissue scrolls from paraffin-embedded tissue blocks were assayed for PCV3 by qPCR. Forty five (93.8%) of the cases were positive for PCV3 with viral titers $1.60\text{-}3.47\times10^4$ gc/ml. To confirm these results, five of the samples with the highest viral titers were analyzed with a PCR targeting a 330 bp fragment of the cap gene. The target amplicon was amplified in all samples evaluated and amplicon product sequences showed 100% identity with the PCV3 genome sequence. Tissues from five PCV3 PCR-positive cases were tested by PCV3-IHC. Three of the five were positive.

PCV3 Seroprevalence

The prevalence of anti-PCV3 cap antibodies in swine sera were examined by ELISA using rPCV3-cap antigen. Eighteen sera samples from 3-week old pigs obtained from a specific pathogen free herd that tested PCV3 qPCR negative were used as negative controls and had an average absorbance of 0.49. The cutoff value differentiating positive and negative sera was determined as three standard deviations above the mean of the negative controls (0.87). Sera from ten sows from the outbreak farm collected three months after the PDNS outbreak were all positive with an average absorbance of 1.27. Additionally, 27 sera from gilts from a farm that supplies replacement animals to the sow farm were also tested, with seventeen animals (63%) having absorbances of 0.88-1.37. Anti-PCV3 cap antibodies were detected in 47 of 83 (56.6%) of samples submitted for unrelated diagnostic testing from multiple states. Of the positive samples, 13 originated from Iowa, one from Indiana, five from Mexico, four from North Carolina, five from Nebraska, one from Oklahoma and 18 were of unknown origin.

Discussion

First described in 1993 in Europe, PDNS has been reported in numerous countries worldwide. Although the prevalence of disease within a herd is typically low (<1%), mortality for afflicted pigs can be high. The incidence of PDNS may exceed that of PMWS in Europe and the United Kingdom. Although the etiology of PDNS is unknown, PCV2 nucleic acid is commonly detected in affected pigs using qPCR, while PCV2 antigen is inconsistently detected. This has led to speculation on the role of PCV2 in PDNS. Here, a highly divergent new species of porcine circovirus, designated PCV3, was identified from mummified fetuses aborted from sows with PDNS-like lesions and from sows which died acutely with clinical signs consistent with PDNS. PCV3 was the only virus identified by metagenomic sequencing of pooled fetal tissue, which was confirmed by qPCR. Cycle threshold values of 16.7-21.3 in fetal tissue pools indicate high viral titers of $7.55\times10^6\text{-}1.88\times10^8$ gc/ml of sample. There is a correlation between PCV2 titer in the fetuses and reproductive disease, with PCV2 levels of $10^7$ PCV2 DNA copies/500 ng fetal tissue or more associated with PCV2-associated reproductive failure including mummification. Based on the amount of PCV3 nucleic acids and tissue distribution detected during this outbreak, a similar correlation for PCV3 and reproductive failure exists.

PCV3 was also detected by PCR and IHC in skin, lung, kidney, and lymph nodes of sows with PDNS-like lesions. Both PCR, IHC and metagenomic sequencing failed to identify PCV2 in the samples collected from the outbreak farm. These results show that PCV3 infection contributes to the PDNS-like lesions and the presence of abortion and PCV3 in fetuses are the results of vertical transmission. In support of this etiologic role for PCV3 in PDNS lesions, screening of archived PCV2 IHC-negative PDNS cases found that PCV3 nucleic acid was highly prevalent (93.8%) and three out of the five cases examined for PCV3 by IHC were positive. It is noted that the relatively low titers of PCV3 in the tissues may limit consistent detection.

Attempts to reproduce PDNS experimentally with PCV2 have been unsuccessful, however, PDNS has been reproduced experimentally in the absence of PCV2 using PRRSV and a tissue homogenate containing TTV. Relatively little is known on the clinical significance of TTV infection. TTV is ubiquitous in pigs worldwide. While TTV is commonly detected in healthy pigs, several studies have suggested TTV infection moderates disease severity during co-infections. For example, inoculation of pigs with a tissue homogenate containing TTV followed by PCV2 resulted in PMWS while mono-infections did not. The sows from the outbreak farm with PDNS were infected with both PCV3 and TTV1. The impact of TTV1 co-infection is unknown. It is unclear whether co-infections with genetically diverse small circular DNA viruses such as TTV1 (Anelloviridae), PCV2 and PCV3 influence the development of PDNS. The additive effects on disease severity of co-infections with PCV2 have been demonstrated for PMWS. A co-infection of PPV and PCV2 has been show to exacerbate disease. PCV2 and PRRSV co-infections are a significant component of the porcine respiratory disease complex. Infection of a herd with these agents causes severe respiratory disease and economically devastating sow abortions and mortality.

The pathogenesis of PDNS, which includes characteristic necrotizing vasculitis, is thought to be a manifestation of an immune complex-mediated disorder involving PCV2. In a case control study, all pigs with clinical signs of PDNS were PCV2-PCR positive and had PCV2 antibody titers significantly higher than clinically normal pigs. Examination of the kidneys of PDNS positive pigs found increased fibrinoid deposits in the glomerula consisting of accumulated of IgG1, IgG2, IgM, and complement factors C1q and C3, as compared to clinically normal pigs. Although PCV2 antigen was identified in lung tissue of these PDNS pigs by IHC, PCV2 antigen was not identified in the immune complexes. This result is similar to the inconsistent detection of PCV2 in renal tissues of PDNS pigs reported by others. Viral infections are known to contribute to immunological disorders, of which Aleutian Mink Disease (AMD), caused by Aleutian Mink Disease Virus (AMDV), has a similar pathogenesis to PDNS. The pathogenesis of AMD has been associated with the overproduction of AMDV-specific IgG antibodies. A role for PCV3 in a possible immune complex-mediated disorder resulting in the pathogenesis of PDNS needs further study.

PCV2 is one of the most economically significant swine viral pathogens worldwide. The most common genotypes associated with PCVAD are PCV2a and PCV2b. Before 2003, PCV2a was the principle genotype identified in the U.S. and Canada, although both PCV2a and PCV2b were found internationally. Around 2003, a drastic shift occurred in the frequency of PCV2 genotypes globally from PCV2a to PCV2b coincident with severe systemic disease associated with PCV2b. The worldwide epidemic was successfully controlled with the development of commercial vaccines, which contain PCV2a antigen, that have been shown to be cross protective. More recently, the novel genotype PCV2d, first detected in Switzerland in 1999, spread to China followed by the U.S. Similar to seen with PCV2b, epidemiological studies suggest a genotype shift is in process with resulting reports of PCV2 vaccine failure and increased clinical disease. PCV2d has been implicated in a more severe clinical signs and lesions.

Circoviruses are genetically diverse and infect a broad range of hosts with documented cross-species transmission. Phylogenetic analysis suggests a closest evolutionary relationship between PCV3 and CanineCV. Interestingly, CanineCV was identified in the liver of a dog displaying necrotizing vasculitis and granulomatous lymphadenitis, both of which were observed in PCV3 infected sows as well as reported in PCV2 infections. It is unclear whether PCV3 has been evolving in pigs undetected for some time or whether it originated via cross-species transmission or has arisen via recombination between unidentified parental circoviruses. PCV2 is capable of crossing species barriers causing fatal disease in species other than swine; a recent report identified PCV2 in six mink that died of diarrhea in China.

The discovery of a novel porcine circovirus with a likely etiologic role in PDNS and reproductive failure is disconcerting. Retrospective studies suggest that PCV2 caused sporadically systemic disease as earlier as 1985 before becoming an epidemic in the late 1990's. The possibility that PCV3 is on a similar trajectory deserves further research and production of the immunogenic compositions of the present disclosure. Importantly, given the approximately 30% identity between the PCV2 and PCV3 capsid proteins, cross protection seems unlikely.

CONCLUSIONS

Porcine circovirus 2 in one of the most significant swine pathogens worldwide. Here, a highly divergent new species of porcine circovirus, PCV3, was identified from sows experiencing abortions and exhibiting PDNS, the latter a clinical manifestation typically associated with PCV2 infection. The PCV3 genome includes ORF1, ORF2, and ORF3. No other viruses were detected by metagenomic sequencing and PCR was negative for PCV2, PPV, PRRSV and IAV. This, coupled with the high viral load in mummy tissue, suggests that PCV3 can cause clinical disease similar to PCV2. Molecular and serological assays for PCV3 also suggest that the virus commonly circulates in the U.S. swine herd. As PCV2 infection initially was subclinical and only sporadically caused disease before becoming a global epidemic, PCV3 warrants further study.

The teaching and content of the following references are hereby incorporated by reference.

Segalés J, Kekarainen T, Cortey M. The natural history of porcine circovirus type 2: from an inoffensive virus to a devastating swine disease? Vet Microbiol. 2013; 165:13-20

Chae C. Commercial porcine circovirus type 2 vaccines: efficacy and clinical application. Vet J. 2012; 194:151-7

Opriessnig T, Langohr I. Current state of knowledge on porcine circovirus type 2-associated lesions. Vet Pathol. 2012; 50:23-38

Meehan B M, McNeilly F, McNair I, Walker I, Ellis J A, Krakowka S, et al. Isolation and characterization of porcine circovirus 2 from cases of sow abortion and porcine dermatitis and nephropathy syndrome. Arch Virol. 2001; 146:835-842

Jacobsen B, Krueger L, Seeliger F, Bruegmann M, Segalés J, Baumgaertner W. Retrospective study on the occurrence of porcine circovirus 2 infection and associated entities in Northern Germany. Vet Microbiol. 2009; 138: 27-33

Cortey M, Pileri E, Sibila M, Pujols J, Balasch M, Plana J, et al. Genotypic shift of porcine circovirus type 2 from PCV-2a to PCV-2b in Spain from 1985 to 2008. Vet J. 2011; 187:363-8.

Cheung A K, Lager K M, Kohutyuk O I, Vincent A L, Henry S C, Baker R B, et al. Detection of two porcine circovirus type 2 genotypic groups in the United States swine herds. Arch Virol. 2007; 152:1035-44

Hause B M, Collin E A, Anderson J, Hesse R A, Anderson G. Bovine rhinitis viruses are common in U.S. cattle with bovine respiratory disease. PLoS One 2015 10:e0121998

Li L, Shan T, Soji O B, Alam M M, Kunz T H, Zaidi S Z, Delwart E. Possible cross-species transmission of circoviruses and cycloviruses among farm animals. J Gen Virol. 2011; 92:768-772

Zhang W, Li L, Deng X, Kapusinszky B, Delwart E. What is for dinner? Viral metagenomics of U.S. store bought beef, pork and chicken. Virology 2014; 468-470:303-310.

Li L, Kapoor A, Slikas B, Bamidele O S, Wang C, et al. Multiple diverse circoviruses infect farm animals and are commonly found in human and chimpanzee feces. J Virol. 2010; 84:1674-1682

King A M Q, Adams M J, Carstens E B, Lefkowitz E J, Carstens E B, editors. Virus taxonomy: classification and nomenclature of viruses: ninth report of the International Committee on Taxonomy of Viruses. San Diego: Academic Press, Elsevier; 2011.

He B, Li Z, Yang F, Zheng J, Guo H, et al. Virome profiling of bats from Myanmar by metagenomics analysis of tissue samples reveals more novel Mammalian viruses. PLoS One 2013; 8:e61950.

Wu P C, Lin W L, Wu C M, Chi J N, Chien M S, et al. Characterization of porcine circovirus type 2 (PCV2) capsid particle assembly and its application to virus-like particle vaccine development. Appl Microbiol Biotechnol. 2012; 95:1501-7

Lin M, Trottier E, Pasick J. Antibody responses of pigs to defined Erns fragments after infection with classical swine fever virus. Clin Diagn Lab Immunol. 2005; 12:180-186.

What is claimed:

1. A vector comprising a heterologous nucleotide sequence encoding a protein, wherein the protein comprises an amino acid sequence having at least 90% sequence identity with SEQ ID NO. 6.

2. The vector of claim 1, wherein the protein comprises an amino acid sequence having at least 95% sequence identity with SEQ ID NO. 6.

3. The vector of claim 1, wherein the vector is a viral vector or a plasmid.

4. The vector of claim 3, wherein the vector is a viral vector.

5. The vector of claim 4, wherein the viral vector is a baculovirus vector.

6. A composition comprising the vector of claim 1.

7. The composition of claim 6, further comprising an additional component selected from the group consisting of an adjuvant, a pharmaceutically acceptable salt, an inactivating agent, a neutralizing agent, a portion of cell culture supernatant, a veterinary acceptable carrier, at least one immunological active component against another disease-causing organism in swine, and any combination thereof.

8. The composition of claim 7, wherein said adjuvant is selected from the group consisting of aluminum hydroxide, aluminum phosphate, saponin, emulsions, polymers of acrylic or methacrylic acid, copolymers of maleic anhydride and alkenyl derivative, the RIBI adjuvant system, block co-polymer, SAF-M, monophosphoryl lipid A, Avirdine lipid-amine, heat-labile enterotoxin from *E. coli*, cholera toxin, IMS 1314, and muramyl dipeptide.

9. The composition of claim 8, wherein said adjuvant is a carbomer.

10. The composition of claim 9, wherein said carbomer is Carbopol or Carbopol 971P.

11. The composition of claim 8, wherein said adjuvant is an emulsion.

12. The composition of claim 11, wherein said emulsion is a water-in-oil-in-water emulsion.

13. The composition of claim 12, wherein said emulsion comprises esters of mannide.

14. The composition of claim 13, wherein said esters of mannide comprise anhydromannitol oleate.

15. The composition of claim 7, wherein said inactivating agent is binary ethylenimine (BEI).

16. The composition of claim 7, wherein the veterinary acceptable carrier is selected from the group consisting of a solvent, a dispersion media, a coating, a stabilizing agent, a diluent, a preservative, an antimicrobial agent, an antifungal agent, an isotonic agent, an adsorption delaying agent, or any combination thereof.

17. The composition of claim 7, wherein said pharmaceutically acceptable salt is a phosphate salt in physiological acceptable concentrations.

18. The composition of claim 7, wherein said neutralizing agent is sodium thiosulfate.

19. A vector comprising a heterologous nucleotide sequence having at least 90% sequence identity with SEQ ID NO. 5.

20. The vector of claim 19, wherein the nucleotide sequence has at least 95% sequence identity with SEQ ID NO. 5.

21. The vector of claim 19, wherein the vector is a viral vector or a plasmid.

22. The vector of claim 21, wherein the vector is a viral vector.

23. The vector of claim 22, wherein the viral vector is a baculovirus vector.

24. A composition comprising the vector of claim 19.

25. The composition of claim 24, further comprising an additional component selected from the group consisting of an adjuvant, a pharmaceutically acceptable salt, an inactivating agent, a neutralizing agent, a portion of cell culture supernatant, a veterinary acceptable carrier, at least one immunological active component against another disease-causing organism in swine, and any combination thereof.

26. The composition of claim 25, wherein said adjuvant is selected from the group consisting of aluminum hydroxide, aluminum phosphate, saponin, emulsions, polymers of acrylic or methacrylic acid, copolymers of maleic anhydride and alkenyl derivative, the RIBI adjuvant system, block co-polymer, SAF-M, monophosphoryl lipid A, Avirdine lipid-amine, heat-labile enterotoxin from *E. coli*, cholera toxin, IMS 1314, and muramyl dipeptide.

27. The composition of claim 26, wherein said adjuvant is a carbomer.

28. The composition of claim 27, wherein said carbomer is Carbopol or Carbopol 971P.

29. The composition of claim 26, wherein said adjuvant is an emulsion.

30. The composition of claim 29, wherein said emulsion is a water-in-oil-in-water emulsion.

31. The composition of claim 30, wherein said emulsion comprises esters of mannide.

32. The composition of claim 31, wherein said esters of mannide comprise anhydromannitol oleate.

33. The composition of claim 25, wherein said inactivating agent is binary ethylenimine (BEI).

34. The composition of claim 25, wherein the veterinary acceptable carrier is selected from the group consisting of a solvent, a dispersion media, a coating, a stabilizing agent, a diluent, a preservative, an antimicrobial agent, an antifungal agent, an isotonic agent, an adsorption delaying agent, or any combination thereof.

35. The composition of claim 25, wherein said pharmaceutically acceptable salt is a phosphate salt in physiological acceptable concentrations.

36. The composition of claim 25, wherein said neutralizing agent is sodium thiosulfate.

37. A vector comprising a heterologous RNA sequence corresponding to a nucleotide sequence having at least 90% sequence identity with SEQ ID NO. 5.

38. The vector of claim 37, wherein the nucleotide sequence has at least 95% sequence identity with SEQ ID NO. 5.

39. The vector of claim 37, wherein the RNA sequence encodes a protein comprising an amino acid sequence having at least 95% sequence identity with SEQ ID NO. 6.

40. The vector of claim 37, wherein the vector is a viral vector or a plasmid.

41. The vector of claim 40, wherein the vector is a viral vector.

42. A composition comprising the vector of claim 37.

43. The composition of claim 42, further comprising an additional component selected from the group consisting of an adjuvant, a pharmaceutically acceptable salt, an inactivating agent, a neutralizing agent, a portion of cell culture supernatant, a veterinary acceptable carrier, at least one immunological active component against another disease-causing organism in swine, and any combination thereof.

44. The composition of claim 43, wherein the veterinary acceptable carrier is selected from the group consisting of a solvent, a dispersion media, a coating, a stabilizing agent, a diluent, a preservative, an antimicrobial agent, an antifungal agent, an isotonic agent, an adsorption delaying agent, or any combination thereof.

45. The composition of claim 43, wherein said pharmaceutically acceptable salt is a phosphate salt in physiological acceptable concentrations.

* * * * *

SEQUENCE LISTING

```
<160> NUMBER OF SEQ ID NOS: 28

<210> SEQ ID NO 1
<211> LENGTH: 2000
<212> TYPE: DNA
<213> ORGANISM: Porcine circovirus 3

<400> SEQUENCE: 1
acccggcacc tcggaacccg gatccacgga ggtctgtagg gagaaaaagt ggtatcccat     60
tatggatgct ccgcaccgtg tgagtggata taccgggcag tggatgatga agcggcctcg    120
tgttttgatg ccgcaggacg gggactggat aactgagttt ttgtggtgct acgagtgtcc   180
tgaagataag gacttttatt gtcatcctat tctaggtccg gagggaaagc ccgaaacaca    240
ggtggtgttt tacgataaac aactggaccc cgaccgagtg ggaatctatt gtggagtgtg    300
gaggcagtat agcgagatac cttattatcg gcaaagaggt tggaaaaagc ggtaccccac    360
acttgcaagg gtacgtgaat tcaagaaca aaaggcgact cagctcggtg aagcgcttac     420
ccggatttgg tcgggcccat ctggagccgg cgaggggag ccacaaagag gccagcgagt    480
attgcaagaa agaggggat tacctcgaga ttggcgaaga ttcctcttcg ggtaccagat     540
cggatcttca agcagcagct cggattctga cggagacgtc gggaaatctg actgaagttg    600
cggagaagat gcctgcagta tttatacgct atgggcgggg tttgcgtgat ttttgcgggg   660
tgatggggtt gggtaaaccg cgtgattta aaactgaagt ttatgttttt attggtcctc    720
caggatgcgg gaaaacgcgg gaagcttgtg cggatgcggc tgcgcgggaa ttgcagttgt   780
atttcaagcc acggggggcct tggtgggatg gttataatgg ggagggtgct gttattttgg   840
atgattttta tgggtgggtt ccatttgatg aattgctgag aattggggac aggtaccctc   900
tgagggttcc tgttaagggt gggtttgtta attttgtggc taaggtatta tatattacta    960
gtaatgttgt accggaggag tggtattcat cggagaatat tcgtggaaag ttggaggcct  1020
tgtttaggag gttcactaag gttgtttgtt gggggagg ggggtaaag aaagacatgg     1080 agacagtgta tccaataaac tattgatttt atttgcactt gtgtacaatt attgcgttgg   1140
ggtgggggta tttattggga gggtgggtgg gcagccccct agccacggct tgtcgccccc   1200
accgaagcat gtgggggatg gggtccccac atgcgagggc gtttacctgt gcccgcaccc   1260
gaagcgcagc gggagcgcgc gcgagggggac acggcttgtc gccaccggag gggtcagatt   1320
tatatttatt ttcacttaga gaacggactt gtaacgaatc caaacttctt tggtgccgta   1380
gaagtctgtc attccagttt tttccgggac ataaatgctc caaagcagtg ctccccattg    1440
aacggtgggg tcatatgtgt tgagccatgg ggtgggtctg gagaaaaaga agaggctttg    1500
tcctgggtga gcgctggtag ttcccgccag aagtggtttg gggtgaagt aacggctgtg     1560 ttttttttta gaagtcataa ctttacgagt ggaactttcc gcataagggt cgtcttggag    1620
ccaagtgttt gtggtccagg cgccgtctag atctatggct gtgtgcccga acatagtttt    1680
tgtttgctga gccggagaaa ttacagggct gagtgtaact ttcattttta gtatcttata    1740
```

-continued atattcaaag gtaattgcag tttcccattc gtttaggcgg gtaatgaagt ggttggcgtg 1800
ccagggcttg ttattctgag ggttccaac ggatatgacg ttcattgtgg agtatttctt 1860
tgtgtagtat gtgccagctg tgggcctcct aatgaatagt cgtcttctgg catagcgcct 1920
tctgtggcgt cgtcgtctcc ttgggcgggg tcttcttctg aatatagctc tgtgtctcat 1980
tttggtgccg ggctagtatt 2000

<210> SEQ ID NO 2
<211> LENGTH: 646
<212> TYPE: PRT
<213> ORGANISM: Porcine circovirus

<400> SEQUENCE: 2

Thr Arg His Leu Gly Thr Arg Ile His Gly Gly Leu Gly Glu Lys Val
1 5 10 15

Val Ser His Tyr Gly Cys Ser Ala Pro Cys Glu Trp Ile Tyr Arg Ala
20 25 30

Val Asp Asp Glu Ala Ala Ser Cys Phe Asp Ala Ala Gly Arg Gly Leu
35 40 45

Asp Asn Val Phe Val Val Leu Arg Val Ser Arg Gly Leu Leu Leu Ser
50 55 60

Ser Tyr Ser Arg Ser Gly Gly Lys Ala Arg Asn Thr Gly Gly Val Leu
65 70 75 80

Arg Thr Thr Gly Pro Arg Pro Ser Gly Asn Leu Leu Trp Ser Val Glu
85 90 95

Ala Val Arg Asp Thr Leu Leu Ser Ala Lys Arg Leu Glu Lys Ala Val
100 105 110

Pro His Thr Cys Lys Gly Thr Ile Ser Arg Thr Lys Gly Asp Ser Ala
115 120 125

Arg Ser Ala Tyr Pro Asp Leu Val Gly Pro Ile Trp Ser Arg Arg Gly
130 135 140

Gly Ala Thr Lys Arg Pro Ala Ser Ile Ala Arg Lys Arg Gly Ile Thr
145 150 155 160

Ser Arg Leu Ala Lys Ile Pro Leu Arg Val Pro Asp Arg Ile Phe Lys
165 170 175

Gln Gln Leu Gly Phe Arg Arg Arg Arg Glu Ile Leu Lys Leu Arg Arg
180 185 190

Arg Cys Leu Gln Tyr Leu Tyr Ala Met Gly Gly Val Cys Val Ile Phe
195 200 205

Ala Gly Trp Gly Trp Val Asn Arg Val Ile Leu Lys Leu Lys Phe Met
210 215 220

Phe Leu Leu Val Leu Gln Asp Ala Gly Lys Arg Gly Lys Leu Val Arg
225 230 235 240

Met Arg Leu Arg Gly Asn Cys Ser Cys Ile Ser Ser His Gly Gly Leu
245 250 255

Gly Gly Met Val Ile Met Gly Arg Val Leu Leu Phe Trp Met Ile Phe
260 265 270

Met Gly Gly Phe His Leu Met Asn Cys Glu Leu Gly Thr Gly Thr Leu
275 280 285

Gly Phe Leu Leu Arg Val Gly Leu Leu Ile Leu Trp Leu Arg Tyr Tyr
290 295 300

Ile Leu Leu Val Met Leu Tyr Arg Arg Ser Gly Ile His Arg Arg Ile
305 310 315 320

Phe Val Glu Ser Trp Arg Pro Cys Leu Gly Gly Ser Leu Arg Leu Phe

|   |   |   | 325 |   |   |   | 330 |   |   |   | 335 |   |
|---|---|---|---|---|---|---|---|---|---|---|---|---|
| Val | Gly | Gly | Arg | Gly | Gly | Arg | Lys | Thr | Trp | Arg | Gln | Cys | Ile | Gln | Thr |

Val Gly Gly Arg Gly Gly Arg Lys Thr Trp Arg Gln Cys Ile Gln Thr
             340                 345                 350
Ile Asp Phe Ile Cys Thr Cys Val Gln Leu Leu Arg Trp Gly Gly Gly
355                 360                 365
Ile Tyr Trp Glu Gly Gly Trp Ala Ala Pro Pro Arg Leu Val Ala Pro
        370                 375                 380
Thr Glu Ala Cys Gly Gly Trp Gly Pro His Met Arg Gly Arg Leu Pro
385                 390                 395                 400
Val Pro Ala Pro Glu Ala Gln Arg Glu Arg Ala Arg Gly Asp Thr Ala
                405                 410                 415
Cys Arg His Arg Arg Gly Gln Ile Tyr Ile Tyr Phe His Leu Glu Asn
            420                 425                 430
Gly Leu Val Thr Asn Pro Asn Phe Phe Gly Ala Val Glu Val Cys His
                435                 440                 445
Ser Ser Phe Phe Arg Asp Ile Asn Ala Pro Lys Gln Cys Ser Pro Leu
        450                 455                 460
Asn Gly Gly Val Ile Cys Val Glu Pro Trp Gly Gly Ser Gly Glu Lys
465                 470                 475                 480
Glu Glu Ala Leu Ser Trp Val Ser Ala Gly Ser Ser Arg Gln Lys Trp
                485                 490                 495
Phe Gly Gly Glu Val Thr Ala Val Phe Phe Arg Ser His Asn Phe
            500                 505                 510
Thr Ser Gly Thr Phe Arg Ile Arg Val Val Leu Glu Pro Ser Val Cys
        515                 520                 525
Gly Pro Gly Ala Val Ile Tyr Gly Cys Val Pro Glu His Ser Phe Cys
530                 535                 540
Leu Leu Ser Arg Arg Asn Tyr Arg Ala Glu Cys Asn Phe His Phe Tyr
545                 550                 555                 560
Leu Ile Ile Phe Lys Gly Asn Cys Ser Phe Pro Phe Val Ala Gly Asn
                565                 570                 575
Glu Val Val Gly Val Pro Gly Leu Val Ile Leu Arg Gly Ser Asn Gly
            580                 585                 590
Tyr Asp Val His Cys Gly Val Phe Leu Cys Val Val Cys Ala Ser Cys
        595                 600                 605
Gly Pro Pro Asn Glu Ser Ser Gly Ile Ala Pro Ser Val Ala Ser
610                 615                 620
Ser Ser Pro Trp Ala Gly Ser Ser Ser Glu Tyr Ser Ser Val Ser His
625                 630                 635                 640
Phe Gly Ala Gly Leu Val
            645

<210> SEQ ID NO 3
<211> LENGTH: 891
<212> TYPE: DNA
<213> ORGANISM: Porcine circovirus ORF1

<400> SEQUENCE: 3
gtccggaggg aaagcccgaa acacaggtgg tgttttacga taaacaactg gaccccgacc    60 gagtgggaat

```
gaagattcct cttcgggtac cagatcggat cttcaagcag cagctcggat tctgacggag    360
acgtcgggaa atctgactga agttgcggag aagatgcctg cagtatttat acgctatggg    420
cggggtttgc gtgattttg cggggtgatg gggttgggta accgcgtga ttttaaaact     480 gaagtttatg ttttttattgg tcctccagga tgcgggaaaa cgcgggaagc ttgtgcggat    540
gcggctgcgc gggaattgca gttgtatttc aagccacggg ggccttggtg ggatggttat    600
aatggggagg gtgctgttat tttggatgat ttttatgggt gggttccatt tgatgaattg    660
ctgagaattg gggacaggta ccctctgagg gttcctgtta agggtgggtt tgttaatttt    720
gtggctaagg tattatatat tactagtaat gttgtaccgg aggagtggta ttcatcggag    780
aatattcgtg gaaagttgga ggccttgttt aggaggttca ctaaggttgt ttgttggggg    840
gagggggggg taaagaaaga catggagaca gtgtatccaa taaactattg a              891
```

<210> SEQ ID NO 4
<211> LENGTH: 296
<212> TYPE: PRT
<213> ORGANISM: Porcine circovirus ORF1

<400> SEQUENCE: 4

```
Val Arg Arg Glu Ser Pro Lys His Arg Trp Cys Phe Thr Ile Asn Asn
1               5                   10                  15

Trp Thr Pro Thr Glu Trp Glu Ser Ile Val Glu Cys Gly Gly Ser Ile
            20                  25                  30

Ala Arg Tyr Leu Ile Ile Gly Lys Glu Val Gly Lys Ser Gly Thr Pro
        35                  40                  45

His Leu Gln Gly Tyr Val Asn Phe Lys Asn Lys Arg Arg Leu Ser Ser
    50                  55                  60

Val Lys Arg Leu Pro Gly Phe Gly Arg Ala His Leu Glu Pro Ala Arg
65                  70                  75                  80

Gly Ser His Lys Glu Ala Ser Glu Tyr Cys Lys Lys Glu Gly Asp Tyr
                85                  90                  95

Leu Glu Ile Gly Glu Asp Ser Ser Ser Gly Thr Arg Ser Asp Leu Gln
            100                 105                 110

Ala Ala Ala Arg Ile Leu Thr Glu Thr Ser Gly Asn Leu Thr Glu Val
        115                 120                 125

Ala Glu Lys Met Pro Ala Val Phe Ile Arg Tyr Gly Arg Gly Leu Arg
    130                 135                 140

Asp Phe Cys Gly Val Met Gly Leu Gly Lys Pro Arg Asp Phe Lys Thr
145                 150                 155                 160

Glu Val Tyr Val Phe Ile Gly Pro Pro Gly Cys Gly Lys Thr Arg Glu
                165                 170                 175

Ala Cys Ala Asp Ala Ala Ala Arg Glu Leu Gln Leu Tyr Phe Lys Pro
            180                 185                 190

Arg Gly Pro Trp Trp Asp Gly Tyr Asn Gly Glu Gly Ala Val Ile Leu
        195                 200                 205

Asp Asp Phe Tyr Gly Trp Val Pro Phe Asp Glu Leu Leu Arg Ile Gly
    210                 215                 220

Asp Arg Tyr Pro Leu Arg Val Pro Val Lys Gly Gly Phe Val Asn Phe
225                 230                 235                 240

Val Ala Lys Val Leu Tyr Ile Thr Ser Asn Val Val Pro Glu Glu Trp
                245                 250                 255

Tyr Ser Ser Glu Asn Ile Arg Gly Lys Leu Glu Ala Leu Phe Arg Arg
            260                 265                 270
```

```
Phe Thr Lys Val Val Cys Trp Gly Glu Gly Gly Val Lys Lys Asp Met
            275                 280                 285

Glu Thr Val Tyr Pro Ile Asn Tyr
    290                 295

<210> SEQ ID NO 5
<211> LENGTH: 645
<212> TYPE: DNA
<213> ORGANISM: Porcine circovirus ORF2

<400> SEQUENCE: 5
atgagacaca gagctatatt cagaagaaga ccccgcccaa ggagacgacg acgccacaga     60
aggcgctatg ccagaagacg actattcatt aggaggccca cagctggcac atactacaca    120
aagaaatact ccacaatgaa cgtcatatcc gttggaaccc ctcagaataa caagccctgg    180
cacgccaacc acttcattac ccgcctaaac gaatgggaaa ctgcaattac ctttgaatat    240
tataagatac taaaaatgaa agttacactc agccctgtaa tttctccggc tcagcaaaca    300
aaaactatgt tcgggcacac agccatagat ctagacggcg cctggaccac aaacacttgg    360
ctccaagacg acccttatgc ggaaagttcc actcgtaaag ttatgacttc taaaaaaaaa    420
cacagccgtt acttcacccc caaaccactt ctggcgggaa ctaccagcgc tcacccagga    480
caaagcctct tctttttctc agacccaccc catggctca acacatatga ccccaccgtt    540
caatggggag cactgctttg agcatttat gtcccggaaa aaactggaat gacagacttc    600
tacggcacca agaagtttg gattcgttac aagtccgttc tctaa                    645

<210> SEQ ID NO 6
<211> LENGTH: 214
<212> TYPE: PRT
<213> ORGANISM: Porcine circovirus ORF2

<400> SEQUENCE: 6

Met Arg His Arg Ala Ile Phe Arg Arg Arg Pro Arg Pro Arg Arg
1               5                   10                  15

Arg Arg His Arg Arg Arg Tyr Ala Arg Arg Arg Leu Phe Ile Arg Arg
            20                  25                  30

Pro Thr Ala Gly Thr Tyr Tyr Thr Lys Lys Tyr Ser Thr Met Asn Val
        35                  40                  45

Ile Ser Val Gly Thr Pro Gln Asn Asn Lys Pro Trp His Ala Asn His
    50                  55                  60

Phe Ile Thr Arg Leu Asn Glu Trp Glu Thr Ala Ile Thr Phe Glu Tyr
65                  70                  75                  80

Tyr Lys Ile Leu Lys Met Lys Val Thr Leu Ser Pro Val Ile Ser Pro
                85                  90                  95

Ala Gln Gln Thr Lys Thr Met Phe Gly His Thr Ala Ile Asp Leu Asp
            100                 105                 110

Gly Ala Trp Thr Thr Asn Thr Trp Leu Gln Asp Asp Pro Tyr Ala Glu
        115                 120                 125

Ser Ser Thr Arg Lys Val Met Thr Ser Lys Lys His Ser Arg Tyr
    130                 135                 140

Phe Thr Pro Lys Pro Leu Leu Ala Gly Thr Ser Ala His Pro Gly
145                 150                 155                 160

Gln Ser Leu Phe Phe Phe Ser Arg Pro Thr Pro Trp Leu Asn Thr Tyr
                165                 170                 175

Asp Pro Thr Val Gln Trp Gly Ala Leu Leu Trp Ser Ile Tyr Val Pro
```

-continued

```
            180                 185                 190
Glu Lys Thr Gly Met Thr Asp Phe Tyr Gly Thr Lys Glu Val Trp Ile
        195                 200                 205

Arg Tyr Lys Ser Val Leu
    210
```

<210> SEQ ID NO 7
<211> LENGTH: 696
<212> TYPE: DNA
<213> ORGANISM: Porcine circovirus ORF3

<400> SEQUENCE: 7

```
tcgtcttctg gcatagcgcc ttctgtggcg tcgtcgtctc cttgggcggg gtcttcttct      60
gaatatagct ctgtgtctca ttttggtgcc gggctagtat tacccggcac ctcggaaccc     120
ggatccacgg aggtctgtag ggagaaaaag tggtatccca ttatggatgc tccgcaccgt     180
gtgagtggat ataccgggca gtggatgatg aagcggcctc gtgttttgat gccgcaggac     240
ggggactgga taactgagtt tttgtggtgc tacgagtgtc ctgaagataa ggacttttat     300
tgtcatccta ttctaggtcc ggagggaaag cccgaaacac aggtggtgtt ttacgataaa     360
caactggacc ccgaccgagt gggaatctat tgtggagtgt ggaggcagta tagcgagata     420
ccttattatc ggcaaagagg ttggaaaaag cggtacccca cacttgcaag ggtacgtgaa     480
tttcaagaac aaaaggcgac tcagctcggt gaagcgctta cccggatttg gtcgggccca     540
tctggagccg gcgagggggga gccacaaaga ggccagcgag tattgcaaga aagaggggga    600
ttacctcgag attggcgaag attcctcttc gggtaccaga tcggatcttc aagcagcagc     660
tcggattctg acggagacgt cgggaaatct gactga                               696
```

<210> SEQ ID NO 8
<211> LENGTH: 231
<212> TYPE: PRT
<213> ORGANISM: Porcine circovirus ORF3

<400> SEQUENCE: 8

```
Ser Ser Ser Gly Ile Ala Pro Ser Val Ala Ser Ser Ser Pro Trp Ala
1               5                   10                  15

Gly Ser Ser Ser Glu Tyr Ser Ser Val Ser His Phe Gly Ala Gly Leu
            20                  25                  30

Val Leu Pro Gly Thr Ser Glu Pro Gly Ser Thr Glu Val Cys Arg Glu
        35                  40                  45

Lys Lys Trp Tyr Pro Ile Met Asp Ala Pro His Arg Val Ser Gly Tyr
    50                  55                  60

Thr Gly Gln Trp Met Met Lys Arg Pro Arg Val Leu Met Pro Gln Asp
65                  70                  75                  80

Gly Asp Trp Ile Thr Glu Phe Leu Trp Cys Tyr Glu Cys Pro Glu Asp
                85                  90                  95

Lys Asp Phe Tyr Cys His Pro Ile Leu Gly Pro Glu Gly Lys Pro Glu
            100                 105                 110

Thr Gln Val Val Phe Tyr Asp Lys Gln Leu Asp Pro Asp Arg Val Gly
        115                 120                 125

Ile Tyr Cys Gly Val Trp Arg Gln Tyr Ser Glu Ile Pro Tyr Tyr Arg
    130                 135                 140

Gln Arg Gly Trp Lys Lys Arg Tyr Pro Thr Leu Ala Arg Val Arg Glu
145                 150                 155                 160

Phe Gln Glu Gln Lys Ala Thr Gln Leu Gly Glu Ala Leu Thr Arg Ile
```

-continued

```
                    165                 170                 175
Trp Ser Gly Pro Ser Gly Ala Gly Glu Gly Glu Pro Gln Arg Gly Gln
            180                 185                 190

Arg Val Leu Gln Glu Arg Gly Gly Leu Pro Arg Asp Trp Arg Arg Phe
        195                 200                 205

Leu Phe Gly Tyr Gln Ile Gly Ser Ser Ser Ser Ser Asp Ser Asp
    210                 215                 220

Gly Asp Val Gly Lys Ser Asp
225                 230

<210> SEQ ID NO 9
<211> LENGTH: 21
<212> TYPE: DNA
<213> ORGANISM: Artificial Sequence
<220> FEATURE:
<223> OTHER INFORMATION: PCV3 replicase primer

<400> SEQUENCE: 9
aggagtggta ttcatcggag a                                              21

<210> SEQ ID NO 10
<211> LENGTH: 22
<212> TYPE: DNA
<213> ORGANISM: Artificial Sequence
<220> FEATURE:
<223> OTHER INFORMATION: PCV3 replicase primer

<400> SEQUENCE: 10
aaacaacctt agtgaacctc ct                                             22

<210> SEQ ID NO 11
<211> LENGTH: 23
<212> TYPE: DNA
<213> ORGANISM: Artificial Sequence
<220> FEATURE:
<223> OTHER INFORMATION: PCV3 5' HEX/ZEN/3' IBFQ replicase probe

<400> SEQUENCE: 11
acaaggcctc caactttcca cga                                            23

<210> SEQ ID NO 12
<211> LENGTH: 19
<212> TYPE: DNA
<213> ORGANISM: Artificial Sequence
<220> FEATURE:
<223> OTHER INFORMATION: PCV3 capsid primer

<400> SEQUENCE: 12
acacagccgt tacttcacc                                                 19

<210> SEQ ID NO 13
<211> LENGTH: 18
<212> TYPE: DNA
<213> ORGANISM: Artificial Sequence
<220> FEATURE:
<223> OTHER INFORMATION: PCV3 capsid primer

<400> SEQUENCE: 13
agtgctcccc attgaacg                                                  18

<210> SEQ ID NO 14
<211> LENGTH: 25
<212> TYPE: DNA
<213> ORGANISM: Artificial Sequence
```

```
<220> FEATURE:
<223> OTHER INFORMATION: PCV3 5' 6-FAM/ZEN/3' IBFQ capsid probe

<400> SEQUENCE: 14
accccatggc tcaacacata tgacc                                          25

<210> SEQ ID NO 15
<211> LENGTH: 9
<212> TYPE: DNA
<213> ORGANISM: Porcine circovirus type 3

<400> SEQUENCE: 15 tagtattac                                                             9

<210> SEQ ID NO 16
<211> LENGTH: 19
<212> TYPE: DNA
<213> ORGANISM: Artificial Sequence
<220> FEATURE:
<223> OTHER INFORMATION: Internal cap gene primer

<400> SEQUENCE: 16
ccacagaagg cgctatgtc                                                 19

<210> SEQ ID NO 17
<211> LENGTH: 19
<212> TYPE: DNA
<213> ORGANISM: Artificial Sequence
<220> FEATURE:
<223> OTHER INFORMATION: Internal cap gene primer

<400> SEQUENCE: 17
ccgcataagg gtcgtcttg                                                 19

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
aaaaaagcta gcgctggaac atactacaca                                     30

<210> SEQ ID NO 19
<211> LENGTH: 33
<212> TYPE: DNA
<213> ORGANISM: Artificial Sequence
<220> FEATURE:
<223> OTHER INFORMATION: Primer

<400> SEQUENCE: 19
aaaaaagaat tcttagagaa cggacttgta acg                                 33

<210> SEQ ID NO 20
<211> LENGTH: 5
<212> TYPE: PRT
<213> ORGANISM: Artificial Sequence
<220> FEATURE:
<223> OTHER INFORMATION: Rolling circle replication motif

<400> SEQUENCE: 20

Phe Thr Leu Asn Asn
1               5
```

```
<210> SEQ ID NO 21
<211> LENGTH: 5
<212> TYPE: PRT
<213> ORGANISM: Artificial Sequence
<220> FEATURE:
<223> OTHER INFORMATION: Rolling circle replication motif

<400> SEQUENCE: 21

Phe Thr Ile Asn Asn
1               5

<210> SEQ ID NO 22
<211> LENGTH: 4
<212> TYPE: PRT
<213> ORGANISM: Artificial Sequence
<220> FEATURE:
<223> OTHER INFORMATION: Rolling circle replication motif

<400> SEQUENCE: 22

His Leu Gln Gly
1

<210> SEQ ID NO 23
<211> LENGTH: 4
<212> TYPE: PRT
<213> ORGANISM: Artificial Sequence
<220> FEATURE:
<223> OTHER INFORMATION: Rolling circle replication motif

<400> SEQUENCE: 23

Tyr Cys Lys Lys
1

<210> SEQ ID NO 24
<211> LENGTH: 5
<212> TYPE: PRT
<213> ORGANISM: Artificial Sequence
<220> FEATURE:
<223> OTHER INFORMATION: Motif of unknown origin

<400> SEQUENCE: 24

Trp Trp Asp Gly Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: Motif of unknown origin

<400> SEQUENCE: 25

Asp Asp Phe Tyr Gly Trp Val Pro
1               5

<210> SEQ ID NO 26
<211> LENGTH: 4
<212> TYPE: PRT
<213> ORGANISM: Artificial Sequence
<220> FEATURE:
<223> OTHER INFORMATION: Motif of unknown origin

<400> SEQUENCE: 26

Asp Arg Tyr Pro
1

<210> SEQ ID NO 27
```

```
<211> LENGTH: 3
<212> TYPE: DNA
<213> ORGANISM: Artificial Sequence
<220> FEATURE:
<223> OTHER INFORMATION: Canonical start codon

<400> SEQUENCE: 27 gtc                                                                      3

<210> SEQ ID NO 28
<211> LENGTH: 3
<212> TYPE: DNA
<213> ORGANISM: Artificial Sequence
<220> FEATURE:
<223> OTHER INFORMATION: start codon

<400> SEQUENCE: 28 atg                                                                      3
```